US009079859B2

(12) United States Patent
Irwin et al.

(10) Patent No.: US 9,079,859 B2
(45) Date of Patent: Jul. 14, 2015

(54) SYNTHETIC LETHAL TARGETING OF GLUCOSE TRANSPORT

(75) Inventors: John Irwin, San Rafael, CA (US); Patrick Sutphin, Boston, MA (US); Denise Chan, San Francisco, CA (US); Sandra Turcotte, Repentigny (CA); Amato Giaccia, Stanford, CA (US); Edwin Lai, Menlo Park, CA (US); Olga Razorenova, Menlo Park, CA (US); Michael Patrick Hay, Auckland (NZ); Muriel Bonnet, Auckland (NZ); Connie Sun, Palo Alto, CA (US); Raymond Tabibiazar, Portola Valley, CA (US)

(73) Assignees: AUCKLAND UNISERVICES LIMITED, Auckland (NZ); THE BOARD OF TRUSTEES OF THE LELAND STANFORD JUNIOR UNIVERSITY, Palo Alto, CA (US); RUGA CORPORATION, Palo Alto, CA (US)

(*) Notice: Subject to any disclaimer, the term of this patent is extended or adjusted under 35 U.S.C. 154(b) by 196 days.

(21) Appl. No.: 13/980,565

(22) PCT Filed: Jan. 20, 2012

(86) PCT No.: PCT/US2012/022113
§ 371 (c)(1),
(2), (4) Date: Jan. 14, 2014

(87) PCT Pub. No.: WO2012/100223
PCT Pub. Date: Jul. 26, 2012

(65) Prior Publication Data
US 2014/0128397 A1 May 8, 2014

Related U.S. Application Data

(60) Provisional application No. 61/435,132, filed on Jan. 21, 2011.

(51) Int. Cl.
| A61K 31/47 | (2006.01) |
| A61K 31/44 | (2006.01) |
| C07D 401/12 | (2006.01) |
| C07D 413/04 | (2006.01) |
| C07D 277/46 | (2006.01) |
| C07D 231/18 | (2006.01) |
| C07D 213/75 | (2006.01) |
| A61K 31/415 | (2006.01) |
| A61K 31/422 | (2006.01) |
| A61K 31/4245 | (2006.01) |
| A61K 31/426 | (2006.01) |
| A61K 31/4402 | (2006.01) |
| A61K 31/4406 | (2006.01) |
| A61K 31/4409 | (2006.01) |
| A61K 31/4412 | (2006.01) |
| A61K 31/443 | (2006.01) |
| A61K 31/4436 | (2006.01) |
| A61K 31/4439 | (2006.01) |
| A61K 31/444 | (2006.01) |
| A61K 31/4545 | (2006.01) |
| A61K 31/496 | (2006.01) |
| A61K 31/4965 | (2006.01) |
| A61K 31/505 | (2006.01) |
| A61K 31/506 | (2006.01) |
| A61K 31/5377 | (2006.01) |
| A61K 31/55 | (2006.01) |
| C07D 215/58 | (2006.01) |
| C07D 231/42 | (2006.01) |
| C07D 277/54 | (2006.01) |
| C07D 413/12 | (2006.01) |
| G01N 33/50 | (2006.01) |

(52) U.S. Cl.
CPC ............ *C07D 213/75* (2013.01); *A61K 31/415* (2013.01); *A61K 31/422* (2013.01); *A61K 31/426* (2013.01); *A61K 31/4245* (2013.01); *A61K 31/44* (2013.01); *A61K 31/4402* (2013.01); *A61K 31/443* (2013.01); *A61K 31/444* (2013.01); *A61K 31/4406* (2013.01); *A61K 31/4409* (2013.01); *A61K 31/4412* (2013.01); *A61K 31/4436* (2013.01); *A61K 31/4439* (2013.01); *A61K 31/4545* (2013.01); *A61K 31/47* (2013.01); *A61K 31/496* (2013.01); *A61K 31/4965* (2013.01); *A61K 31/505* (2013.01); *A61K 31/506* (2013.01); *A61K 31/5377* (2013.01); *A61K 31/55* (2013.01); *C07D 215/58* (2013.01); *C07D 231/42* (2013.01); *C07D 277/54* (2013.01); *C07D 401/12* (2013.01); *C07D 413/12* (2013.01); *G01N 33/5008* (2013.01)

(58) Field of Classification Search
CPC ..... A61K 31/47; A61K 31/44; C07D 401/12; C07D 413/04; C07D 277/46; C07D 231/18
USPC ............. 514/237.2, 313, 318, 340, 352, 371, 514/407; 435/14, 375
See application file for complete search history.

(56) References Cited

U.S. PATENT DOCUMENTS

| 7,312,234 | B2 | 12/2007 | Bridger et al. |
| 7,531,556 | B2 | 5/2009 | Green |
| 7,618,947 | B2 | 11/2009 | Marcusson et al. |
| 2003/0228592 | A1 | 12/2003 | Rogers et al. |
| 2006/0025429 | A1 | 2/2006 | Dervan et al. |
| 2007/0009938 | A1 | 1/2007 | Shin |
| 2009/0098537 | A1 | 4/2009 | Sawyers et al. |
| 2010/0166701 | A1 | 7/2010 | Parker |
| 2010/0210735 | A1 | 8/2010 | Lu |

OTHER PUBLICATIONS

International Search Report issued in Appln No. PCT/US2012/022113 mailed May 10, 2012.

*Primary Examiner* — Raymond Henley, III
(74) *Attorney, Agent, or Firm* — Cooley LLP

(57) ABSTRACT

The present invention provides methods for inhibiting growth and proliferation of HIF pathway proficient cells by administering GLUT1 inhibitors of the invention to HIF pathway proficient cells.

29 Claims, 14 Drawing Sheets

SYNTHETIC LETHAL TARGETING OF GLUCOSE TRANSPORT

CROSS REFERENCE TO RELATED APPLICATION

This application is filed under 35 U.S.C. §371 for PCT Application No. PCT/US2012/022113 filed Jan. 21, 2011, which claims priority from U.S. Provisional Application Ser. No. 61/435,132, filed Jan. 21, 2011, both of which are hereby incorporated by reference in their entireties for all purposes.

BACKGROUND

Hypoxia-inducible factors are heterodimeric transcription factors consisting of an oxygen-sensitive alpha subunit (HIF-α) and a constitutive nuclear beta subunit (HIF-β). The alpha subunit is the regulatory subunit specific to the oxygen response pathway, and can be one of three subunits, HIF1α, 2α or 3α (HIF-1 α, HIF-2 α and HIF-3α, respectively) (Maxwell et al., *Curr. Opin. Genet. Dev.*, 11:293-299 (2001); Safran and Kaelin, *J. Clin. Invest.*, 111:779-783 (2003)).

Hypoxia-inducible factor-1 (HIF1) is a heterodimer composed of a 120 kDa alpha subunit complexed with a 91 to 94 kDa beta subunit, both of which contain a basic helix-loop-helix (Wang and Semenza, *J. Biol. Chem.*, 270:1230-1237 (1995)). The gene encoding hypoxia-inducible factor-1 alpha (HIF1-alpha, also called HIF-1 alpha, HIF-1A, HIF-1A, HIF1-A, and MOP1) was cloned in 1995 (Wang et al., *Proc. Natl. Acad. Sci. U.S.A.*, 92:5510-5514 (1995)).

Hypoxia inducible factors (HIFs), are essential regulators and mediators of the cellular oxygen-signaling pathway and are important for maintaining cellular oxygen homeostasis. (See., e.g., Rankin, et al., *Cell Death and Diff*, 12:678-685 (2008)). Hypoxia induces the expression of genes participating in many cellular and physiological processes, including oxygen transport and iron metabolism, erythropoiesis, angiogenesis, glycolysis, glucose uptake, transcription, metabolism, pH regulation, growth-factor signaling, response to stress and cell adhesion. Hypoxia-induced pathways, in addition to being required for normal cellular processes, can also aid tumor growth by allowing or aiding angiogenesis, immortalization, genetic instability, tissue invasion and metastasis (Harris, *Nat. Rev. Cancer*, 2:38-47 (2002)); Maxwell et al., *Curr. Opin. Genet. Dev.*, 11:293-299 (2001)).

As oxygen homeostasis is essential to both cellular and systemic functions, cellular and systemic oxygen concentrations are tightly regulated via response pathways that affect the activity and expression of a multitude of cellular proteins. This balance is disrupted in a variety of diseases, including heart disease, cancer, cerebrovascular disease, and chronic obstructive pulmonary disease (Semenza et al., *Genes Dev.*, 14: 1983-1991 (2000); Semenza et al., *Trends Mol. Med.*, 7:345-350 (2001)). Cellular changes can include an increase in glycolysis and an increase in production of angiogenic factors. In fact, some tumor cells undergo adaptive mutations that allow them to proliferate even under hypoxic conditions. Hypoxia in tumors can be further associated with resistance to radiotherapies and chemotherapies, and thus can be an indicator of poor survival.

Glucose transporter 1 (GLUT1), also known as solute carrier family 2 (SLCA2) or facilitated glucose transporter member 1 (SLC2A1) is a 492 amino acid protein (NCBI accession numbers NP_006507.2 or P11166.2). GLUT1 is a member of a small family 45-55 kDa hexose transport proteins and is invovled in facilitating the transport of glucose across the plasma membranes of mammalian cells. (See, e.g., Doege et al., *Biochem J.*, 15:(359):443-449 (2001); Mueckler, et al., *Science* 229(4717):941-945(1985); and Olsen et al., *Annual Review of Nutrition*, 16:235-256 (1996)).

An important aspect of personalized medicine is the identification of targeted therapies useful in the treatment of difficult to treat diseases. Such therapies are particularly important in cancer, where the goal is to preferentially inhibit the growth and proliferation of tumor cells while leaving normal cells unaffected. The ability to treat individual patients with specific therapies is becoming increasingly important to those being treated as well as to those administering the treatments. Physicians, patients, and third-party payers all seek therapies tailored to the individual needs of the patient.

SUMMARY OF THE INVENTION

The present invention is based in part on the discovery that inhibiting GLUT1 can lead to preferential cell death or inhibition of cell proliferation with respect to HIF pathway proficient cells. Accordingly the present invention provides methods for inhibiting cell growth or proliferation by targeting GLUT1 in HIF pathway proficient cells.

In one embodiment, the present invention provides methods for inhibiting cell growth or proliferation of a cell that is HIF pathway proficient comprising contacting a cell wherein the cell is HIF pathway proficient with a therapeutic entity, wherein the therapeutic entity inhibits the activity of GLUT1 and wherein the therapeutic entity preferentially inhibits the growth or proliferation of neoplastic cells versus normal cells. The methods of the present invention further provide that inhibiting cellular growth results in cellular death.

The methods of the present invention also provide that the therapeutic entity comprises a compound of Formula I, II, III, or IV:

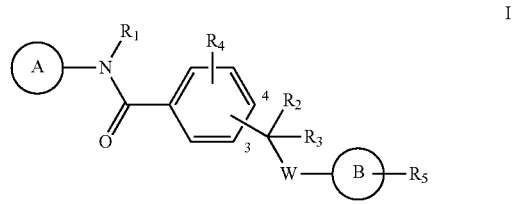

I wherein:

A is a nitrogen-containing heteroaryl ring chosen from pyridinyl, pyrimidinyl, pyrazinyl, quinolinyl, pyrazolyl, imidazolyl, and thiazolyl, each of which is optionally substituted;

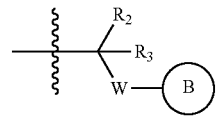

is attached to the phenyl ring at either the 3 or 4 position;
$R_1$, $R_2$, and $R_3$ are each independently chosen from hydrogen, optionally substituted alkyl, and optionally substituted alkenyl;
$R_4$ and $R_5$ are each independently chosen from hydrogen, hydroxy, optionally substituted alkyl, optionally substituted alkenyl, optionally substituted alkoxy, optionally substituted cycloalkyl, optionally substituted aryl, optionally substituted heterocycloalkyl, optionally substituted heteroaryl, halo, carboxy, nitro, sulfonyl, sulfinyl, and optionally substituted amino;

W is chosen from —NRSO₂—, —SO₂NR—, and —NRCO—, wherein each R is independently chosen from hydrogen, alkyl, alkenyl, alkynyl, cycloalkyl, aryl, heterocycloalkyl, and heteroaryl, each of which, except for hydrogen, is optionally substituted; and B is an aryl ring;

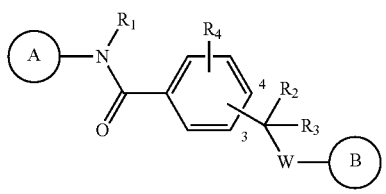

wherein:

A is a nitrogen-containing heteroaryl ring chosen from pyridinyl, pyrimidinyl, pyrazinyl, quinolinyl, pyrazolyl, imidazolyl, and thiazolyl, each of which is optionally substituted;

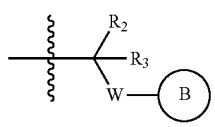

is attached to the phenyl ring at either the 3 or 4 position;

R₁, R₂, and R₃ are each independently chosen from hydrogen, optionally substituted alkyl, and optionally substituted alkenyl;

R₄ is chosen from hydrogen, hydroxy, optionally substituted alkyl, optionally substituted alkenyl, optionally substituted alkoxy, optionally substituted cycloalkyl, optionally substituted aryl, optionally substituted heterocycloalkyl, optionally substituted heteroaryl, halo, carboxy, nitro, sulfonyl, sulfinyl, and optionally substituted amino;

W is chosen from —NRSO₂—, —SO₂NR—, and —NRCO—, wherein each R is independently chosen from hydrogen, alkyl, alkenyl, alkynyl, cycloalkyl, aryl, heterocycloalkyl, and heteroaryl, each of which, except for hydrogen, is optionally substituted; and B is heteroaryl;

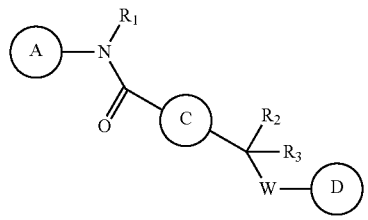

wherein:

A is a nitrogen-containing heteroaryl ring chosen from pyridinyl, pyrimidinyl, pyrazinyl, quinolinyl, pyrazolyl, imidazolyl, and thiazolyl, each of which is optionally substituted;

R₁, R₂, and R₃ are each independently chosen from hydrogen, optionally substituted alkyl, and optionally substituted alkenyl;

W is chosen from —N(R)SO₂R$_X$—, —SO₂N(R)R$_X$—, and —N(R)COR$_X$—, wherein each R is independently chosen from hydrogen, alkyl, alkenyl, alkynyl, cycloalkyl, aryl, heterocycloalkyl, and heteroaryl, each of which, except for hydrogen, is optionally substituted; and R$_X$ is an bivalent C₀-C₆alkylene, bivalent C₃-C₆cycloalkyl, or phenyl, each of which is optionally substituted;

C is selected from C₅-C₆cycloalkyl, and phenyl, wherein C is optionally substituted hydrogen, hydroxy, optionally substituted alkyl, optionally substituted alkenyl, optionally substituted alkoxy, optionally substituted cycloalkyl, optionally substituted aryl, optionally substituted heterocycloalkyl, optionally substituted heteroaryl, halo, carboxy, nitro, sulfonyl, sulfinyl, and optionally substituted amino; and D is an optionally substituted heterocycle;

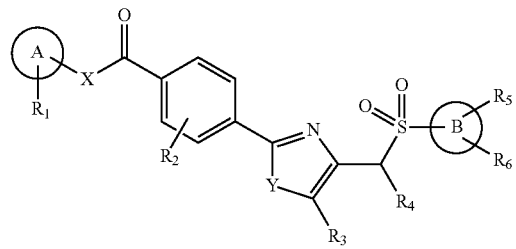

wherein

A is a nitrogen-containing heteroaryl ring chosen from pyridinyl, pyrazinyl, and imidazolyl, each of which is optionally substituted;

X is CH₂CH₂NR, CH₂NR, or NR wherein each R is independently chosen from hydrogen, alkyl, alkenyl, alkynyl, cycloalkyl, aryl, heterocycloalkyl, and heteroaryl, each of which, except for hydrogen, is optionally substituted;

R₁, R₂, R₃, and R₄ are each independently chosen from hydrogen, alkyl, alkenyl, alkynyl, cycloalkyl, aryl, heterocycloalkyl, and heteroaryl, each of which, except for hydrogen, is optionally substituted;

Y is chosen from O, S, NR; wherein each R is independently chosen from hydrogen, alkyl, alkenyl, alkynyl, cycloalkyl, aryl, heterocycloalkyl, and heteroaryl, each of which, except for hydrogen, is optionally substituted; and B is an optionally substituted aryl ring.

In some embodiments, the compounds of Formula I, II, III, or IV are compounds of Formula IA, IIA, IIIA, or IVA:

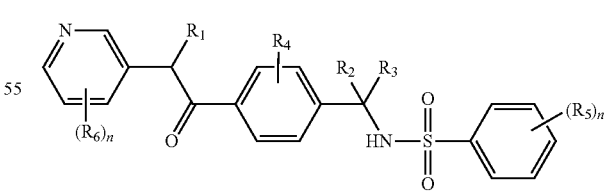

wherein:

R₁, R₂, and R₃ are each independently chosen from hydrogen, optionally substituted alkyl, and optionally substituted alkenyl; and each R₄ and R₅ is independently chosen from hydrogen, hydroxy, optionally substituted alkyl, optionally substituted alkenyl, optionally substituted alkoxy, optionally substituted cycloalkyl, optionally substituted aryl, optionally substituted heterocycloalkyl, optionally substituted heteroaryl, halo, carboxy, nitro, sulfonyl, sulfinyl, and optionally substituted amino; and for each occurrence, $R_6$ is independently chosen from alkyl optionally substituted with one or more halo, alkoxy, halo, nitro, heterocycloalkyl, and amino optionally substituted with $C(O)R_a$, wherein $R_a$ is chosen from alkyl and optionally substituted alkoxy; and each n is 0, 1, or 2;

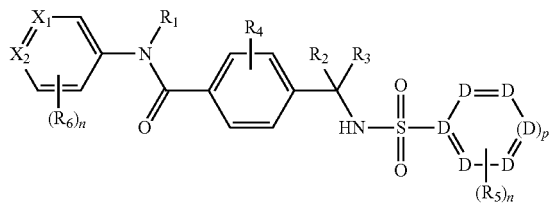

IIA wherein $X_1$ and $X_2$ are each independently chosen from N, NO, and CH, provided that at least one of $X_1$ and $X_2$ is not CH;

each D is individually taken from the group consisting of C, CH, NH, N, S and O, such that the resultant ring is selected from pyridyl, furanyl, imidazolyl, triazolyl, and thienyl;

$R_1$, $R_2$, and $R_3$ are each independently chosen from hydrogen, optionally substituted alkyl, and optionally substituted alkenyl;

$R_4$ and $R_5$ are independently chosen from hydrogen, hydroxy, optionally substituted alkyl, optionally substituted alkenyl, optionally substituted alkoxy, optionally substituted cycloalkyl, optionally substituted aryl, optionally substituted heterocycloalkyl, optionally substituted heteroaryl, halo, carboxy, nitro, sulfonyl, sulfinyl, and optionally substituted amino; and for each occurrence, $R_6$ is independently chosen from alkyl optionally substituted with one or more halo, alkoxy, halo, nitro, heterocycloalkyl, and amino optionally substituted with $C(O)R_a$, wherein $R_a$ is chosen from alkyl and optionally substituted alkoxy;

each n is 0, 1 or 2; and p is 0 or 1;

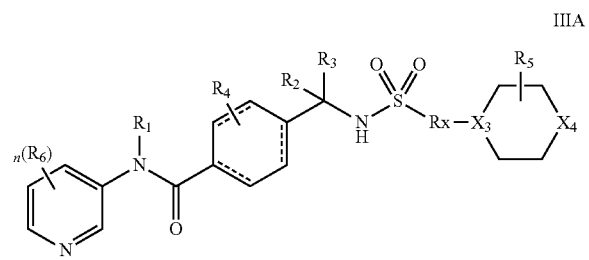

IIIA wherein:

$X_3$ is selected from CH or N;

$X_4$ is selected from O, NH, or $NR_1$;

$R_1$, $R_2$, and $R_3$ are each independently chosen from hydrogen, optionally substituted alkyl, and optionally substituted alkenyl;

$R_4$ and $R_5$ are independently chosen from hydrogen, hydroxy, optionally substituted alkyl, optionally substituted alkenyl, optionally substituted alkoxy, optionally substituted cycloalkyl, optionally substituted aryl, optionally substituted heterocycloalkyl, optionally substituted heteroaryl, halo, carboxy, nitro, sulfonyl, sulfinyl, and optionally substituted amino;

for each occurrence, $R_6$ is independently chosen from alkyl optionally substituted with one or more halo, alkoxy, halo, nitro, heterocycloalkyl, and amino optionally substituted with $C(O)R_a$, wherein $R_a$ is chosen from alkyl and optionally substituted alkoxy;

$R_X$ is an bivalent $C_4$alkylene, bivalent $C_6$cycloalkyl, or phenyl, each of which is optionally substituted; and n is 0, 1, or 2;

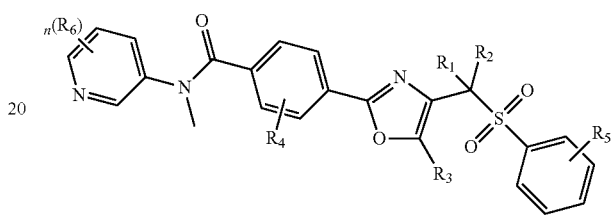

IVA wherein $R_1$, $R_2$, and $R_3$ are each independently chosen from hydrogen, alkyl, alkenyl, alkynyl, cycloalkyl, aryl, heterocycloalkyl, and heteroaryl, each of which, except for hydrogen, is optionally substituted;

$R_4$ and $R_5$ are independently chosen from hydrogen, hydroxy, optionally substituted alkyl, optionally substituted alkenyl, optionally substituted alkoxy, optionally substituted cycloalkyl, optionally substituted aryl, optionally substituted heterocycloalkyl, optionally substituted heteroaryl, halo, carboxy, nitro, sulfonyl, sulfinyl, and optionally substituted amino;

for each occurrence, $R_6$ is independently chosen from alkyl optionally substituted with one or more halo, alkoxy, halo, nitro, heterocycloalkyl, and amino optionally substituted with $C(O)R_a$, wherein $R_a$ is chosen from alkyl and optionally substituted alkoxy; and n is 0, 1, or 2.

The present invention also provides methods for inhibiting cell growth or proliferation comprising contacting a cell with a therapeutic entity, wherein the therapeutic entity inhibits the activity of GLUT1 and affects the activity of a gene in HIF pathway, and wherein the therapeutic entity preferentially inhibits the growth or proliferation of neoplastic cells versus normal cells.

The present invention also provides methods for treatment of neoplasia, such methods comprising administering to a subject determined to be HIF pathway proficient a therapeutic entity, wherein the therapeutic entity inhibits the activity of GLUT1 and wherein the therapeutic entity preferentially inhibits the growth or proliferation of neoplastic cells versus normal cells in the subject.

The present invention further provides methods for treatment of neoplasia comprising determining whether a subject is HIF pathway proficient, and administering to a subject that is determined HIF pathway proficient a therapeutic entity, wherein the therapeutic entity inhibits the activity of GLUT1.

DETAILED DESCRIPTION OF THE INVENTION

Figure 1:
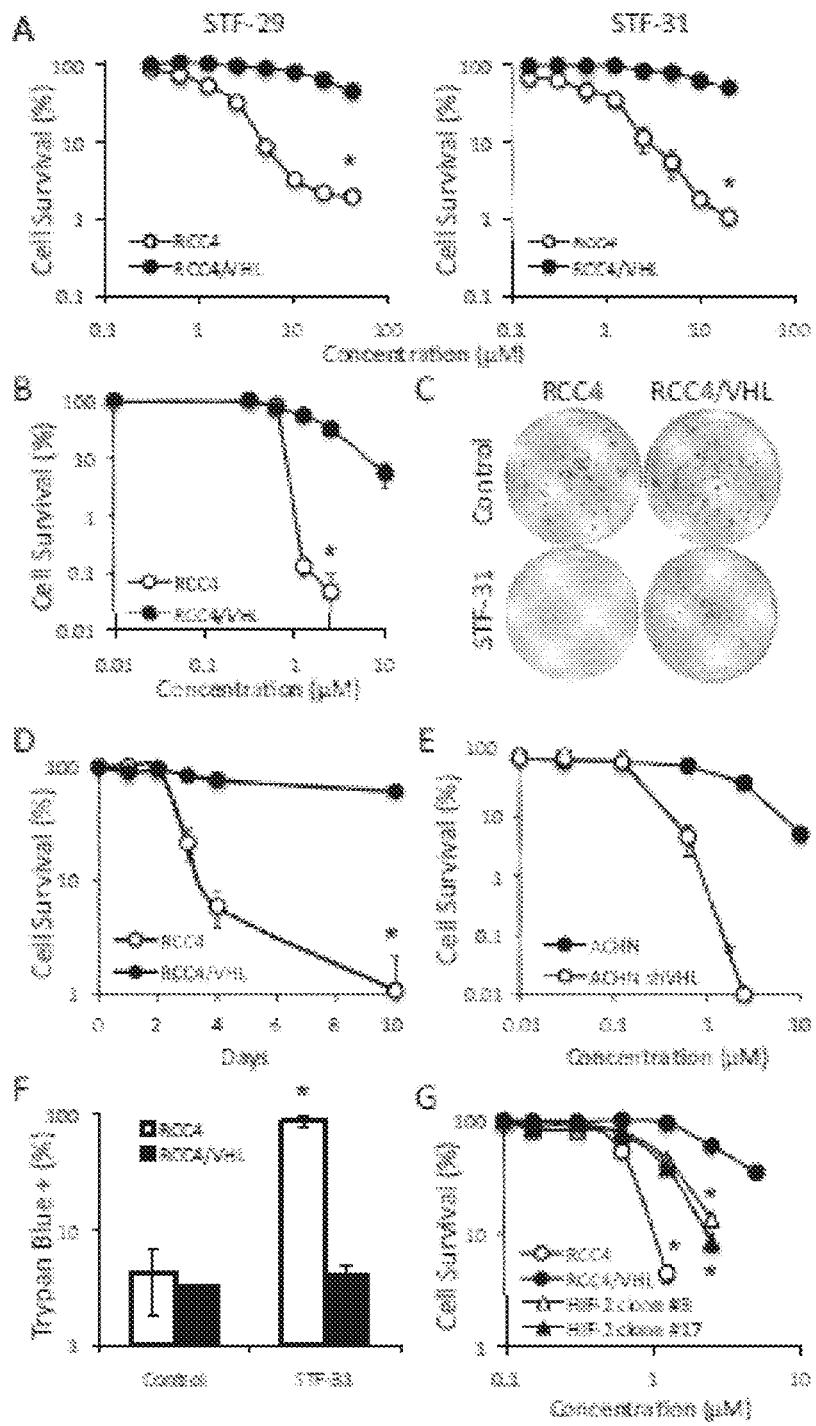
FIG. 1. Chemical synthetic lethal screen identifies compounds that specifically target loss of VHL in renal carcinoma. (A) XTT validation of 4-phenylsulfonamido-N-(pyridin-3-yl)benzamides (PPBs): STF-29 and STF-31 were identified from chemical synthetic lethal screen of renal carcinoma cells that have lost VHL. Cells were treated for 4 days ($*p<0.0005$). (B) Clonogenic survival of RCC4 with and without VHL in response to STF-31. Cells were treated for 10 days ($*p<0.00005$). (C) Representative plates of clonogenic survival in RCC4 and RCC4/VHL cells. Three hundred cells were treated with 5 µM of STF-31 for 10 days. (D) STF-31-induced cell death is irreversible after three days. Cells were treated with STF-31 (5 µM). The media was replaced after the indicated time and cells were allowed to grow for a total of 10 days ($*p<0.0005$). (E) Clonogenic survival of ACHN with and without shRNA to VHL in response to STF-31 ($*p<0.0001$). (F) STF-31 induces a necrotic cell death. RCC4 and RCC4/VHL cells were treated for 3 days with 5 µM of STF-31 and amount of cell death was examined by trypan blue staining ($*p<0.01$). (G) STF-31 toxicity is mediated through HIF. RCC4, RCC4/VHL or RCC4/VHL cell clones overexpressing HIF-2a were treated with STF-31 ($*p<0.005$). All error bars represent the standard error of the mean.

The present invention is based in part on the discovery that inhibiting GLUT1 can lead to preferential cell death or inhibition of cell proliferation with respect to HIF pathway proficient cells. Accordingly the present invention provides methods for inhibiting cell growth or proliferation by targeting GLUT1 in HIF pathway proficient cells.

According to one aspect of the present invention, it provides methods for inhibiting cell growth or proliferation by contacting a cell that is HIF pathway proficient with a therapeutic entity that inhibits the activity of GLUT1. In some embodiments, HIF pathway proficient includes any cellular state where one or more functions associated with HIF pathway is enhanced, increased, or activated.

According to the present invention, the HIF pathway include any gene or gene product that regulate or are regulated by HIF directly or indirectly. In one embodiment, the HIF pathway includes genes whose products participate in either increasing oxygen delivery to hypoxic tissues or activating an alternative metabolic pathway (glycolysis) which does not require oxygen. These genes can include aldolase A (ALDA), angiopoietin 1 (ANG-1), angiopoietin 2 (ANG-2), Akt/PKB, cyclin D1 (CCND-1), connective tissue growth factor (CTGF); C-X-C chemokine receptor type 4 (CXCR4), E-cadherin; erythropoietin (EPO), enolase1 (ENO1), FLK-1, glucose transporter 1 (GLUT1), glucose transporter 3 (GLUT3), glyceraldehyde-3-phosphate dehydrogenase, hexokinase 1 (HK1), hexokinase 2 (HK2), insulin-like growth factor-2 (IGF-2), IGF-factor-binding protein 2 (IGF-BP2), IGF binding protein 1, IGF binding protein 3, lactate dehydrogenase A (LDHA), lysyl oxidase (LOX), MAPK, matrix metalloproteinase-2 (MMP-2), matrix metalloproteinase-9 (MMP-9), max interactor 1 (MXI-1), MYC, plasminogen activator inhibitor-1 (PAI-1), platelet-derived growth factor-B (PDGF-B,), Phosphatidylinositol 3-kinases (PI3K), pyruvate dehydrogenase kinase 1 (PDK1), phosphofructokinase L (PFKL), phosphoglycerate kinase 1 (PGK1), pyruvate kinase M, p21, p35, PTEN, transforming growth factor β3, ceruloplasmin, transferrin, transferrin receptor, alb-adrenergic receptor, adrenomedullin, endothelin-1, heme oxygenase 1, nitric oxide synthase 2, plasminogen activator inhibitor 1, vascular endothelial growth factor (VEGF), VEGF receptor FLT-1, VEGF receptor 2, Ras, Raf, SDF-1, stromal-derived factor 1, transforming growth factor-α (TGF-α), TIE-2, urokinase plasminogen activator receptor (UPAR), Src, ErbB2, PTEN and/or vascular endothelial growth factor (VEGF) (See, e.g., Rankin, et al., *Cell Death and Diff,* 12:678-685 (2008) and Semenza, *Genes Dev.,* 14:1983-1991 (2000)).

In another embodiment, the HIF pathway can include two or more genes or gene products selected from those listed above or others known in the art to regulate or be regulated by HIF. In some embodiments, the HIF pathway includes at least two genes selected from the group consisting of VHL, HIF, PDK1, PDH, GLUT1, MXI1, MYC, Ras, and PTEN.

In some other embodiments, HIF pathway proficient includes any cellular state where it is partially or substantially dependant upon glycolysis or glucose uptake for cellular metabolism. In some embodiments, HIF pathway proficient includes the cellular state wherein the cell is glycolysis dependent.

In some embodiments, HIF pathway proficient can include any cellular state where it has one or more genetic mutations in the HIF pathway. In some embodiments, the cell has a genetic condition including a VHL mutation, a Ras signaling pathway mutation, a SRC mutation, a PTEN mutation, somatic gene amplification of GLUT1, somatic Akt gene amplification or a p53 mutation or a combination thereof. In some other embodiments, the cell has a genetic condition including one or more somatic mutations that lead to HIF1 stabilization, increase levels of HIF1, or increase levels of GLUT1. In yet some other embodiments, the cell has a genetic condition including one or more somatic gene mutations that confer dependency on glycolysis or GLUT1 function.

In some other embodiments, HIF pathway proficient can include a cellular state where it has stabilized HIF. HIF stabilization can include HIF up-regulation, increased HIF expression, increased activation of HIF, aberrant HIF stabilization and reduced HIF degradation. Methods for detecting increased expression, activation, aberrant stabilization and reduced degradation are well known in the art and any standard methods can be employed for detection. Reduced degradation or HIF up-regulation can occur due to, for example, increased translation of the HIF protein. Increased expression of HIF can occur due to mutations in genes or gene products that are involved with regulating HIF expression. Aberrant stabilization and reduced degradation can be due to mutations in the proteins involved in HIF degradation, for example, mutations in the ubiquitin-proteosome degradation pathway proteins. Aberrant stabilization can also result from improper protein folding resulting from, for example, mutations in HIF or mutations in proteins involved in HIF folding.

In yet some other embodiments, HIF pathway proficient can include the cellular state where the cell has decreased or reduced mitochondrial function. Mitochondrial function can be measure by a variety of methods known in the art. A reduction in mitochondrial function can be determined by comparing the level to standard levels known for normal cells. Assay methods for determining mitochondrial function can include the use of Clark-type electrode probes for measuring oxygen consumption, luminescent ATP assays for quantification of total energy metabolism, and MTT or Alamar Blue for determination of metabolic activity.

In yet some other embodiments, HIF pathway proficient can include the cellular state where the cell has aerobic glycolysis. Aerobic glycolysis can be measured by a variety of methods known in the art, including positron emission tomography (PET) imaging of the uptake of $^{18}$F-2-deoxyglucose (FDG), a radioactive modified hexokinase substrate, as well as lactate production and extracellular acidification. In some embodiments the cell has aerobic glycolysis. In additional embodiments, the cell has increased aerobic glycolysis.

In yet some other embodiments, HIF pathway proficient can include the cellular state where the cell has pyruvate dehydrogenase kinase 1 (PDK1) up-regulation. PDK1 up-regulation can include increased PDK1 expression, increased PDK1 activation and increased PDK1 stabilization. Methods for detecting increased expression, stabilization, and activation are well known in the art and any standard methods can be employed fro detection. Increased expression of PDK1 can occur due to mutations in genes or gene products that are involved with regulating PDK1 expression. Increased activation can occur due to, for example, increased phosphorylation of PDK1 or decreased de-phosphorylation of PDK1. Increased stabilization can be due to mutations in the proteins involved in PDK deactivation or degradation. In some embodiments, HIF pathway proficient cells have up-regulated PDK1.

In yet some other embodiments, HIF pathway proficient can include the cellular state where the cell has pyruvate dehydrogenase (PDH) down-regulation. PDH down-regulation can include decreased PDH expression, decreased PDH activation and decreased PDH stabilization. Methods for detecting decreased expression, stabilization, and activation are well known in the art and any standard methods can be employed for detection. Decreased expression of PDH can occur due to mutations in genes or gene products that are involved with regulating PDH expression. Decreased stabilization can be due to mutations in the proteins involved in PDK deactivation or degradation. Decreased activation can occur due to, for example, decreased dephosphorylation of PDH or increased phosphorylation of PDH In yet some other embodiments, HIF pathway proficient can include the cellular state where the cell has MXI1 up-regulation. Max-Interacting protein (MXI1) up-regulation can include increased MXI1 expression, increased MXI1 activation and increased MXI1 stabilization. Methods for detecting increased expression, stabilization and activation are well known in the art and any standard methods can be employed for detection. Increased expression of MXI1 can occur due to mutations in genes or gene products that are involved with regulating MXI1 expression. Increased activation can occur due to, for example, increased phosphorylation of MXI1 or decreased de-phosphorylation of MIX1. Increased stabilization can be due to mutations in the proteins involved in MXI1 deactivation or degradation. In some embodiments, HIF pathway proficient cells have up-regulated MXI1.

In yet some other embodiments, HIF pathway proficient can include the cellular state where the cell has MYC down-regulation. MYC down-regulation can include decreased MYC expression, decreased MYC activation and decreased MYC stabilization. Methods for detecting decreased expression, stabilization and activation are well known in the art and any standard methods can be employed for detection. Decreased expression of PDH can occur due to mutations in genes or gene products that are involved with regulating MYC expression, for example, decreased expression can occur due to increased expression of MIX1 which inhibits MYC expression by repressing the MYC promoter. Decreased stabilization can be due to mutations in the proteins involved in MYC deactivation or degradation. For example, increased degradation can occur due to in dephosphorylation of MYC. In some embodiments the cell has MYC down-regulation.

According to the present invention, therapeutic entities of the present invention, e.g., useful for inhibiting the activity of GLUT1 include any suitable therapeutic entity that decreases, reduces, or inhibits one or more activities of GLUT1. In some embodiments, therapeutic entities of the present invention inhibit the activity of GLUT1 at gene expression level, post-gene expression level, gene translation level, post-gene translation level, protein level, or protein activation level. In some other embodiments, therapeutic entities of the present invention inhibit the activity of GLUT1 by regulating other molecules interacting with GLUT1. In yet some other embodiments, therapeutic entities of the present invention inhibit the activity of GLUT1 by blocking GLUT1 targets downstream of GLUT1 pathway. In still some other embodiments, therapeutic entities of the present invention inhibit the activity of GLUT1 by binding to one or more regions of GLUT1. In still yet some other embodiments, therapeutic entities of the present invention inhibit the activity of GLUT1 including glucose uptake by interacting directly or indirectly with GLUT1.

In some embodiments, the therapeutic entity of the present invention inhibits the activity of GLUT1 via binding to a synthetic targeting region of GLUT1. According to the present invention, the synthetic targeting region of GLUT1 includes any region within GLUT1, the binding of which works in combination with another condition in the system, e.g., cellular state of HIF proficient. In some embodiments, the synthetic targeting region of GLUT1 includes one or more transmembrane regions of GLUT1. In some other embodiments, the synthetic targeting region of GLUT1 includes at least 1, 2, 3, 4, 5, or 6 transmembrane regions of GLUT1. In yet some other embodiments, the synthetic targeting region of GLUT1 includes one or more transmembrane regions of TMS2 (aa64-86), TMS4 (aa120-141), TMS5 (aa157-178), TMS7 (aa267-291), TMS8 (aa305-325) and TMS11(aa401-421).

In yet some other embodiments, the synthetic targeting region can include a region about 19 angstroms in length along the axis perpendicular to a cell membrane or a region marked by GLY286C of GLUT1 at a first end and THR137C of GLUT1 at a second end. In yet some other embodiments, the synthetic targeting region can include a region defined by one or more amino acid residues of ILE168, GLN72, THR310, ILE311, GLY314, SER313, GLY282, GLY286, ILE287 and GLU380 of GLUT1. In yet some other embodiments, the synthetic targeting region can include one or more amino acid residues of GLN282, GLN283, ILE287, PHE416, TRP412, ILE164, ILE168, ASN34, GLY31, THR30, and GLY27 of GLUT1, or at least PHE416, TRP412, ILE168 and ILE287 of GLUT1, or at least GLN283 and ASN34 of GLUT1. In yet some other embodiments, the synthetic targeting region can include a region defined by one or more amino acid residues of TRP412, THR30, CYS133, SER73, GLY76 and GLY134 of GLUT1. The synthetic targeting region can alternatively include a region defined by one or more amino acid residues of ASN23, TRP388, HIS160, THR136, THR137, LEU159, LEU162, GLY163, SER23, ILE164, and TRP412 of GLUT1.

In some embodiments, the therapeutic entity of the present invention includes compounds of Formula I, e.g., compounds of Formula I that bind to GLUT1 to inhibit GLUT1 activity. Compounds of Formula I include

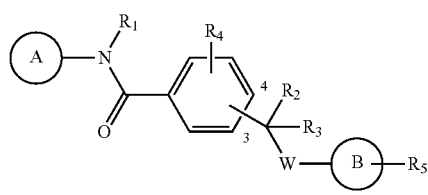

wherein:
A is a nitrogen-containing heteroaryl ring chosen from pyridinyl, pyrimidinyl, pyrazinyl, quinolinyl, pyrazolyl, imidazolyl, and thiazolyl, each of which is optionally substituted;

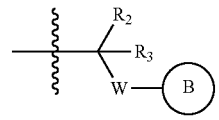

is attached to the phenyl ring at either the 3 or 4 position;
$R_1$, $R_2$, and $R_3$ are each independently chosen from hydrogen, optionally substituted alkyl, and optionally substituted alkenyl;
$R_4$ and $R_5$ are each independently chosen from hydrogen, hydroxy, optionally substituted alkyl, optionally substituted alkenyl, optionally substituted alkoxy, optionally substituted cycloalkyl, optionally substituted aryl, optionally substituted heterocycloalkyl, optionally substituted heteroaryl, halo, carboxy, nitro, sulfonyl, sulfinyl, and optionally substituted amino;
W is chosen from —NRSO$_2$—, —SO$_2$NR—, and —NRCO—, wherein each R is independently chosen from hydrogen, alkyl, alkenyl, alkynyl, cycloalkyl, aryl, heterocycloalkyl, and heteroaryl, each of which, except for hydrogen, is optionally substituted; and
B is an aryl ring.

In some embodiments, therapeutic compounds of the present invention are compounds of Formula I which are of the Formula IA:

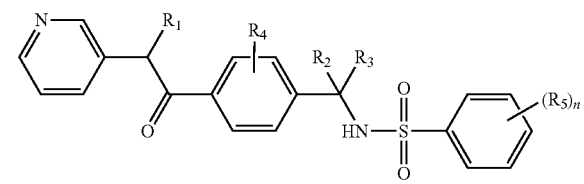

wherein:
$R_1$, $R_2$, and $R_3$ are each independently chosen from hydrogen, optionally substituted alkyl, and optionally substituted alkenyl; and
$R_4$ and $R_5$ are each independently chosen from hydrogen, hydroxy, optionally substituted alkyl, optionally substituted alkenyl, optionally substituted alkoxy, optionally substituted cycloalkyl, optionally substituted aryl, optionally substituted heterocycloalkyl, optionally substituted heteroaryl, halo, carboxy, nitro, sulfonyl, sulfinyl, and optionally substituted amino.

Illustrative examples of compounds of Formula I and IA are described below:
4-(Phenylsulfonamidomethyl)-N-(pyridin-2-yl)benzamide;
4-(Phenylsulfonamidomethyl)-N-(pyridin-3-yl)benzamide;
4-(Phenylsulfonamidomethyl)-N-(pyridin-4-yl)benzamide;
4-(Phenylsulfonamidomethyl)-N-(thiazol-2-yl)benzamide;
4-(Phenylsulfonamidomethyl)-N-(1H-pyrazol-3-yl)benzamide;
4-(Phenylsulfonamidomethyl)-N-(quinolin-3-yl)benzamide;
4-(Phenylsulfonamidomethyl)-N-(quinolin-5-yl)benzamide;
4-(Phenylsulfonamidomethyl)-N-(pyrazin-2-yl)benzamide;

4-(Phenylsulfonamidomethyl)-N-(pyrimidin-2-yl)benzamide;
4-((2-Methylphenylsulfonamido)methyl)-N-(pyridin-3-yl)benzamide;
4-((2-Fluorophenylsulfonamido)methyl)-N-(pyridin-3-yl)benzamide;
4-((2-Chlorophenylsulfonamido)methyl)-N-(pyridin-3-yl)benzamide;
4-((2-Bromophenylsulfonamido)methyl)-N-(pyridin-3-yl)benzamide;
Methyl 2-(N-(4-(Pyridin-3-ylcarbamoyl)benzyl)sulfamoyl)benzoate;
N-(Pyridin-3-yl)-4-((2-(trifluoromethyl)phenylsulfonamido)methyl)benzamide;
4-((2-Cyanophenylsulfonamido)methyl)-N-(pyridin-3-yl)benzamide;
4-((3-Aminophenylsulfonamido)methyl)-N-(pyridin-3-yl)benzamide;
4-((3-Methylphenylsulfonamido)methyl)-N-(pyridin-3-yl)benzamide;
4-((3-Fluorophenylsulfonamido)methyl)-N-(pyridin-3-yl)benzamide;
4-((3-Bromophenylsulfonamido)methyl)-N-(pyridin-3-yl)benzamide;
4-((3-Cyanophenylsulfonamido)methyl)-N-(pyridin-3-yl)benzamide;
4-((3-Nitrophenylsulfonamido)methyl)-N-(pyridin-3-yl)benzamide;
4-{[([1,1'-Biphenyl]-3-ylsulfonyl)amino]methyl}-N-(3-pyridinyl)benzamide;
4-[({[3-(2-Pyrimidinyl)phenyl]sulfonyl}amino)methyl]-N-(3-pyridinyl)benzamide;
4-[({[3-(1-Methyl-1H-pyrazol-3-yl)phenyl]sulfonyl}amino)methyl]-N-(3-pyridinyl)benzamide;
4-[({[3-(5-Methyl-1,3,4-oxadiazol-2-yl)phenyl]sulfonyl}amino)methyl]-N-(3-pyridinyl)benzamide;
4-[({[3-(5-Methyl-1,2,4-oxadiazol-3-yl)phenyl]sulfonyl}amino)methyl]-N-(3-pyridinyl)benzamide;
4-[({[3-(2-Methyl-1,3-thiazol-4-yl)phenyl]sulfonyl}amino)methyl]-N-(3-pyridinyl)benzamide;
4-((4-Aminophenylsulfonamido)methyl)-N-(pyridin-3-yl)benzamide;
4-((4-Butoxyphenylsulfonamido)methyl)-N-(pyridin-3-yl)benzamide;
4-((4-Phenoxyphenylsulfonamido)methyl)-N-(pyridin-3-yl)benzamide;
4-((4-Methylphenylsulfonamido)methyl)-N-(pyridin-3-yl)benzamide;
4-((4-Propylphenylsulfonamido)methyl)-N-(pyridin-3-yl)benzamide;
4-[({[4-(1-Adamantyl)phenyl]sulfonyl}amino)methyl]-N-(3-pyridinyl)benzamide;
4-[({[4-(3-Chloro-1-adamantyl)phenyl]sulfonyl}amino)methyl]-N-(3-pyridinyl)benzamide;
Methyl 3-{4-[({4-[(3Pyridinylamino)carbonyl]benzyl}amino)sulfonyl]phenyl}propanoate;
4-((4-Acetamidophenylsulfonamido)methyl)-N-(pyridin-3-yl)benzamide;
4-((4-Chlorophenylsulfonamido)methyl)-N-(pyridin-3-yl)benzamide;
4-((4-Bromophenylsulfonamido)methyl)-N-(pyridin-3-yl)benzamide;
N-(Pyridin-3-yl)-4-((4-(trifluoromethoxy)phenylsulfonamido)methyl)benzamide;
Methyl 4-(N-(4-(Pyridin-3-ylcarbamoyl)benzyl)sulfamoyl)benzoate;
N-(Pyridin-3-yl)-4-((4-(trifluoromethyl)phenylsulfonamido)methyl)benzamide;
4-((4-Cyanophenylsulfonamido)methyl)-N-(pyridin-3-yl)benzamide;
4-((4-Nitrophenylsulfonamido)methyl)-N-(pyridin-3-yl)benzamide;
4-((Biphenyl-4-ylsulfonamido)methyl)-N-(pyridin-3-yl)benzamide;
4-({[(4'-Methoxy[1,1'-biphenyl]-4-yl)sulfonyl]amino}methyl)-N-(3-pyridinyl)benzamide;
4-({[(4'-Methyl[1,1'-biphenyl]-4-yl)sulfonyl]amino}methyl)-N-(3-pyridinyl)benzamide;
4-({[(4'-Fluoro[1,1'-biphenyl]-4-yl)sulfonyl]amino}methyl)-N-(3-pyridinyl)benzamide;
4-({[(4'-Chloro[1,1'-biphenyl]-4-yl)sulfonyl]amino}methyl)-N-(3-pyridinyl)benzamide;
4-[({[4-(2-Pyrimidinyl)phenyl]sulfonyl}amino)methyl]-N-(3-pyridinyl)-benzamide;
4-[({[4-(1H-Pyrazol-1-yl)phenyl]sulfonyl}amino)methyl]-N-(3-pyridinyl)benzamide;
4-[({[4-(2-Methyl-1,3-thiazol-4-yl)phenyl]sulfonyl}amino)methyl]-N-(3-pyridinyl)benzamide;
[({[4-(1,3-Oxazol-5-yl)phenyl]sulfonyl}amino)methyl]-N-(3-pyridinyl)benzamide;
4-((3,4-Dimethoxyphenylsulfonamido)methyl)-N-(pyridin-3-yl)benzamide;
4-((3-tert-Butyl-4-methoxyphenylsulfonamido)methyl)-N-(pyridin-3-yl)benzamide;
4-((2,3,4,5,6-Pentamethylphenylsulfonamido)methyl)-N-(pyridin-3-yl)benzamide;
4-((2,4-Dimethylphenylsulfonamido)methyl)-N-(pyridin-3-yl)benzamide;
4-((3,4-Dimethylphenylsulfonamido)methyl)-N-(pyridin-3-yl)benzamide;
4-((3,5-Dimethylphenylsulfonamido)methyl)-N-(pyridin-3-yl)benzamide;
4-((3-Fluoro-4-methylphenylsulfonamido)methyl)-N-(pyridin-3-yl)benzamide;
4-((3-Chloro-2-methylphenylsulfonamido)methyl)-N-(pyridin-3-yl)benzamide;
4-((3-Chloro-4-methylphenylsulfonamido)methyl)-N-(pyridin-3-yl)benzamide;
4-((3,4-Dichlorophenylsulfonamido)methyl)-N-(pyridin-3-yl)benzamide;
4-((3-Cyano-4-fluorophenylsulfonamido)methyl)-N-(pyridin-3-yl)benzamide;
4-((Naphthalene-2-sulfonamido)methyl)-N-(pyridin-3-yl)benzamide;
4-((5-(Dimethylamino)naphthalene-1-sulfonamido)methyl)-N-(pyridin-3-yl)benzamide;
4-((2,3-Dihydro-1H-indene-5-sulfonamido)methyl)-N-(pyridin-3-yl)benzamide;
4-((2-(Dimethylamino)-2,3-dihydro-1H-indene-5-sulfonamido)methyl)-N-(pyridin-3-yl)benzamide;
4-((4-(4-Methylpiperazin-1-yl)phenylsulfonamido)methyl)-N-(pyridin-3-yl)benzamide;
4-[({4-[(Dimethylamino)methyl]phenyl}sulfonyl)amino]methyl-N-(3-pyridinyl)benzamide;
4-{[({4-[(Diethylamino)methyl]phenyl}sulfonyl)amino]methyl}-N-(3-pyridinyl)benzamide,
4-{[({4-[(Dipropylamino)methyl]phenyl}sulfonyl)amino]methyl}-N-(3-pyridinyl)benzamide;
4-[({[4-(1-Pyrrolidinylmethyl)phenyl]sulfonyl}amino)methyl]-N-(3-pyridinyl)-benzamide;
4-[({[4-(1-Piperidinylmethyl)phenyl]sulfonyl}amino)methyl]-N-(3-pyridinyl)benzamide;

4-[({[4-(1-Azepanylmethyl)phenyl]sulfonyl}amino)methyl]-N-(3-pyridinyl)benzamide;
4-[({[4-(4-Morpholinylmethyl)phenyl]sulfonyl}amino)methyl]-N-(3-pyridinyl)benzamide;
4-{[({4-[(4-Methoxy-1-piperidinyl)methyl]phenyl}sulfonyl)amino]methyl}-N-(3-pyridinyl)benzamide;
4-{[({4-[(4-Methyl-1-piperazinyl)methyl]phenyl}sulfonyl)amino]methyl}-N-(3-pyridinyl)benzamide;
4-tert-Butyl-N-(4-(pyridin-3-ylcarbamoyl)benzyl)benzamide;
4-((4-tert-Butylphenylsulfonamido)methyl)-N-methyl-N-(pyridin-3-yl)benzamide;
N-Methyl-4-(phenylsulfonamidomethyl)-N-(pyridin-3-yl)benzamide;
3-((4-tert-Butylphenylsulfonamido)methyl)-N-(pyridin-3-yl)benzamide;
3-(Phenylsulfonamidomethyl)-N-(pyridin-3-yl)benzamide;
3-(4-(Phenylsulfonamidomethyl)benzamido)pyridine 1-oxide;
4-((4-Iodophenylsulfonamido)methyl)-N-(pyridin-3-yl)benzamide;
4-((4-Ethynylphenylsulfonamido)methyl)-N-(pyridin-3-yl)benzamide;
4-((4-Bromophenylsulfonamido)methyl)-N-(pyridin-3-yl)benzamide;
4-((4-Fluorophenylsulfonamido)methyl)-N-(pyridin-3-yl)benzamide;
3,5-Dimethyl-N-(4-(pyridin-3-ylcarbamoyl)benzyl)benzamide;
3,4-Dimethoxy-N-(4-(pyridin-3-ylcarbamoyl)benzyl)benzamide;
4-{[({4-[3-(Methyloxy)-1-propynyl]phenyl}sulfonyl)amino]methyl}-N-(3-pyridinyl)benzamide;
4-[(4-Iodophenylsulfonamido)methyl]-N-methyl-N-(4-pyridinyl)benzamide;
4-[({[4-(21-Amino-4,7,10,13,16,19-hexaoxahenicos-1-yn-1-yl)phenyl]sulfonyl}amino)methyl]-N-(3-pyridinyl)benzamide;
4-[({[4-(3-Methoxypropyl)phenyl]sulfonyl}amino)methyl]-N-(3-pyridinyl)benzamide;
4-[({[4-(1-benzyl-1H-1,2,3-triazol-4-yl)phenyl]sulfonyl}amino)methyl]-N-(3-pyridinyl)benzamide;
4-[({[4-(3-Hydroxy-1-propynyl)phenyl]sulfonyl}amino)methyl]-N-(3-pyridinyl)benzamide;
4-[({[4-(3-Hydroxypropyl)phenyl]sulfonyl}amino)methyl]-N-(3-pyridinyl)benzamide;
4-[({[4-(21-Amino-4,7,10,13,16,19-hexaoxahenicos-1-yn-1-yl)phenyl]sulfonyl}amino)methyl]-N-(4-pyridinyl)benzamide;
4-((4-tert-Butylphenylsulfonamido)methyl)-N-(pyridin-4-yl)benzamide;
4-({[(4-tert-Butylphenyl)sulfonyl]amino}methyl)-N-(5-methyl-3-pyridinyl)benzamide;
4-({[(4-tert-Butylphenyl)sulfonyl]amino}methyl)-N-(2-methyl-3-pyridinyl)benzamide;
4-({[(4-tert-Butylphenyl)sulfonyl]amino}methyl)-N-(6-methyl-3-pyridinyl)benzamide;
4-({[(4-tert-Butylphenyl)sulfonyl]amino}methyl)-N-(6-methoxy-3-pyridinyl)benzamide;
4-({[(4-tert-Butylphenyl)sulfonyl]amino}methyl)-N-(6-chloro-3-pyridinyl)benzamide;
4-({[(4-tert-Butylphenyl)sulfonyl]amino}methyl)-N-(4-chloro-3-pyridinyl)benzamide;
4-({[(4-tert-Butylphenyl)sulfonyl]amino}methyl)-N-(2-chloro-3-pyridinyl)benzamide;
4-({[(4-tert-Butylphenyl)sulfonyl]amino}methyl)-N-(4-methyl-3-pyridinyl)benzamide;
4-({[(4-tert-Butylphenyl)sulfonyl]amino}methyl)-N-(5-chloro-3-pyridinyl)benzamide;
4-({[(4-tert-Butylphenyl)sulfonyl]amino}methyl)-N-(2-nitro-3-pyridinyl)benzamide;
4-({[(4-tert-Butylphenyl)sulfonyl]amino}methyl)-N-[6-(4-morpholinyl)-3-pyridinyl]benzamide;
4-({[(4-tert-Butylphenyl)sulfonyl]amino}methyl)-N-[6-(trifluoromethyl)-3-pyridinyl]benzamide;
N-[6-(Acetylamino)-3-pyridinyl]-4-({[(4-tert-butylphenyl)sulfonyl]amino}methyl)benzamide;
4-({[(4-tert-Butylphenyl)sulfonyl]amino}methyl)-N-(6-fluoro-3-pyridinyl)benzamide;
4-({[(4-tert-Butylphenyl)sulfonyl]amino}methyl)-N-(5-fluoro-3-pyridinyl)benzamide;
4-({[(4-tert-Butylphenyl)sulfonyl]amino}methyl)-N-[4-(trifluoromethyl)-3-pyridinyl]benzamide;
4-({[(4-tert-Butylphenyl)sulfonyl]amino}methyl)-N-(2-fluoro-3-pyridinyl)benzamide;
4-({[(4-tert-Butylphenyl)sulfonyl]amino}methyl)-N-(4-methoxy-3-pyridinyl)benzamide;
N-(6-Bromo-3-pyridinyl)-4-({[(4-tert-butylphenyl)sulfonyl]amino}methyl)benzamide;
4-[({[3-(4-Morpholinyl)phenyl]sulfonyl}amino)methyl]-N-(3-pyridinyl)benzamide;
4-[({[4-(4-Morpholinyl)phenyl]sulfonyl}amino)methyl]-N-(3-pyridinyl)benzamide;
4-[({[4-(1-Pipendinyl)phenyl]sulfonyl}amino)methyl]-N-(3-pyridinyl)benzamide;
4-[({[4-(1-Pipendinyl)phenyl]sulfonyl}amino)methyl]-N-(3-pyridinyl)benzamide;
4-[({[4-(21-Amino-4,7,10,13,16,19-hexaoxahenicos-1-yl)phenyl]sulfonyl}amino) methyl]-N-(3-pyridinyl)benzamide;
4-({[(4-{[3-(4-Morpholinyl)propyl]amino}phenyl)sulfonyl]amino}methyl)-N-(3-pyridinyl)benzamide;
4-[({[3-(4-Methyl-1-piperazinyl)phenyl]sulfonyl}amino)methyl]-N-(3-pyridinyl)benzamide;
4-({[(4-{[2-(Dimethylamino)ethyl]amino}phenyl)sulfonyl]amino}methyl)-N-(3-pyridinyl)benzamide;
N-(3-Pyridinyl)-4-[({[3'-(trifluoromethyl)[1,1'-biphenyl]-4-yl]sulfonyl}amino)methyl]benzamide;
4-({[(4-Benzylphenyl)sulfonyl]amino}methyl)-N-(3-pyridinyl)benzamide;
4-{[({4-[3-(4-Morpholinyl)-1-propynyl]phenyl}sulfonyl)amino]methyl}-N-(3-pyridinyl)benzamide;
4-{[({4-[3-(Dimethylamino)-1-propynyl]phenyl}sulfonyl)amino]methyl}-N-(3-pyridinyl)benzamide;
4-{[[(4-tert-Butylphenyl)sulfonyl](methyl)amino]methyl}-N-(3-pyridinyl)benzamide;
4-{[[(4-tert-Butylphenyl)sulfonyl](ethyl)amino]methyl}-N-(3-pyridinyl)benzamide;
4-{[[(4-tert-Butylphenyl)sulfonyl](propyl)amino]methyl}-N-(3-pyridinyl)benzamide;
4-{[({4-[3-(4-Morpholinyl)propyl]phenyl}sulfonyl)amino]methyl}-N-(3-pyridinyl)benzamide;
4-{[({4-[3-(Dimethylamino)propyl]phenyl}sulfonyl)amino]methyl}-N-(3-pyridinyl)benzamide;
4-[({[3-(Propionylamino)phenyl]sulfonyl}amino)methyl]-N-(3-pyridinyl)benzamide;
4-[({[3-(Acryloylamino)phenyl]sulfonyl}amino)methyl]-N-(3-pyridinyl)benzamide;
4-({[(4-tert-Butylphenyl)sulfonyl]amino}methyl)-2-methyl-N-(3-pyridinyl)benzamide;
4-({[(4-tert-Butylphenyl)sulfonyl]amino}methyl)-2-fluoro-N-(3-pyridinyl)benzamide;

4-({[(4-tert-Butylphenyl)sulfonyl]amino}methyl)-3-methyl-N-(3-pyridinyl)benzamide;
4-({[(4-tert-Butylphenyl)sulfonyl]amino}methyl)-3-fluoro-N-(3-pyridinyl)benzamide;
4-(1-{[(4-tert-Butylphenyl)sulfonyl]amino}ethyl)-N-(3-pyridinyl)benzamide;
4-[(anilinosulfonyl)methyl]-N-(3-pyridinyl)benzamide;
4-{[(4-tert-butylanilino)sulfonyl]methyl}-N-(3-pyridinyl)benzamide;
4-{[(4-fluoroanilino)sulfonyl]methyl}-N-(3-pyridinyl)benzamide; and
4-({[4-(4-methyl-1-piperazinyl)anilino]sulfonyl}methyl)-N-(3-pyridinyl)benzamide;
4-((4-(tert-butyl)phenylsulfonamido)methyl)-2-methyl-N-(pyridin-3-yl)benzamide;
4-((4-(tert-butyl)phenylsulfonamido)methyl)-3-methyl-N-(pyridin-3-yl)benzamide;
4-((4-(tert-butyl)phenylsulfonamido)methyl)-2-fluoro-N-(pyridin-3-yl)benzamide;
4-((4-(tert-butyl)phenylsulfonamido)methyl)-3-fluoro-N-(pyridin-3-yl)benzamide;
4-((4-(tert-butyl)phenylsulfonamido)methyl)-3-nitro-N-(pyridin-3-yl)benzamide;
4-(1-(4-(tert-butyl)phenylsulfonamido)ethyl)-N-(pyridin-3-yl)benzamide,
4-(N-phenylsulfamoylmethyl)-N-(pyridin-3-yl)benzamide;
4-((N-(4-fluorophenyl)sulfamoyl)methyl)-N-(pyridin-3-yl)benzamide;
4-((N-(4-tert-butylphenyl)sulfamoyl)methyl)-N-(pyridin-3-yl)benzamide;
4-((N-(4-(4-methylpiperazin-1-yl)phenyl)sulfamoyl)methyl)-N-(pyridin-3-yl)benzamide;
4-((3-Methoxyphenylsulfonamido)methyl)-N-(pyridin-3-yl)benzamide;
4-((3,4-dimethylphenylsulfonamido)methyl)-N-(pyridin-3-yl)benzamide;
3-((3,4-dimethylphenylsulfonamido)methyl)-N-(pyridin-3-yl)benzamide;
N-(pyridin-3-yl)-3-((2,3,4-trifluorophenylsulfonamido)methyl)benzamide;
N-(pyridin-3-yl)-4-((2,3,4-trifluorophenylsulfonamido)methyl)benzamide;
N-(pyridin-3-yl)-3-((2,3,5,6-tetramethylphenylsulfonamido)methyl)benzamide;
N-(pyridin-3-yl)-4-((2,3,5,6-tetramethylphenylsulfonamido)methyl)benzamide;
3-((2,5-dimethylphenylsulfonamido)methyl)-N-(pyridin-3-yl)benzamide;
4-((2,5-dimethylphenylsulfonamido)methyl)-N-(pyridin-3-yl)benzamide;
4-((3-Chlorophenylsulfonamido)methyl)-N-(pyridin-3-yl)benzamide;
N-(Pyridin-3-yl)-4-((3-(trifluoromethyl)phenylsulfonamido)methyl)benzamide;
4-((4-Methoxyphenylsulfonamido)methyl)-N-(pyridin-3-yl)benzamide;
3-((4-tert-Butylphenylsulfonamido)methyl)-N-(pyridin-3-yl)benzamide;
4-((4-Fluorophenylsulfonamido)methyl)-N-(pyridin-3-yl)benzamide; and
4-((4-Acetylphenylsulfonamido)methyl)-N-(pyridin-3-yl)benzamide.

In some other embodiments, therapeutic compounds of the present invention include compounds of Formula II and IIA, e.g., compounds of Formula II and IIA which bind to GLUT1:

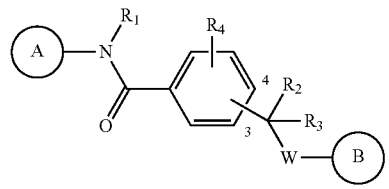

II wherein:
A is a nitrogen-containing heteroaryl ring chosen from pyridinyl, pyrimidinyl, pyrazinyl, quinolinyl, pyrazolyl, imidazolyl, and thiazolyl, each of which is optionally substituted;

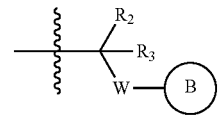

is attached to the phenyl ring at either the 3 or 4 position;
$R_1$, $R_2$, and $R_3$ are each independently chosen from hydrogen, optionally substituted alkyl, and optionally substituted alkenyl;
$R_4$ is chosen from hydrogen, hydroxy, optionally substituted alkyl, optionally substituted alkenyl, optionally substituted alkoxy, optionally substituted cycloalkyl, optionally substituted aryl, optionally substituted heterocycloalkyl, optionally substituted heteroaryl, halo, carboxy, nitro, sulfonyl, sulfinyl, and optionally substituted amino;
W is chosen from —NRSO$_2$—, —SO$_2$NR—, and —NRCO—, wherein each R is independently chosen from hydrogen, alkyl, alkenyl, alkynyl, cycloalkyl, aryl, heterocycloalkyl, and heteroaryl, each of which, except for hydrogen, is optionally substituted; and
B is heteroaryl.

Also provided herein are compounds of Formula IIA which bind to GLUT1:

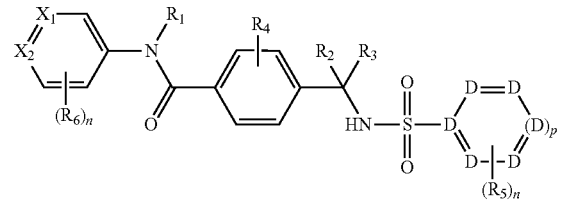

IIA wherein
$X_1$ and $X_2$ are each independently chosen from N, NO, and CH, provided that at least one of $X_1$ and $X_2$ is not CH;
each D is individually taken from the group consisting of C, CH, NH, N, S and O, such that the resultant ring is selected from pyridyl, furanyl, imidazolyl, triazolyl, and thienyl;
$R_1$, $R_2$, and $R_3$ are each independently chosen from hydrogen, optionally substituted alkyl, and optionally substituted alkenyl;
$R_4$ and $R_5$ are independently chosen from hydrogen, hydroxy, optionally substituted alkyl, optionally substituted alkenyl, optionally substituted alkoxy, optionally substituted cycloalkyl, optionally substituted aryl, optionally substituted heterocycloalkyl, optionally substituted heteroaryl, halo, carboxy, nitro, sulfonyl, sulfinyl, and optionally substituted amino; and for each occurrence, $R_6$ is independently chosen from alkyl optionally substituted with one or more halo, alkoxy, halo, nitro, heterocycloalkyl, and amino optionally substituted with $C(O)R_a$, wherein $R_a$ is chosen from alkyl and optionally substituted alkoxy;

each n is 0, 1 or 2; and p is 0 or 1.

Illustrative examples of compounds of Formula II and IIA are described below:

N-(3-Pyridinyl)-4-{[(3-pyridylsulfonyl)amino]methyl}benzamide;

4-({[(6-Chloro-3-pyridinyl)sulfonyl]amino}methyl)-N-(3-pyridinyl)benzamide;

4-({[(6-Phenoxy-3-pyridinyl)sulfonyl]amino}methyl)-N-(3-pyridinyl)benzamide;

N-(3-Pyridinyl)-4-{[(2-thienylsulfonyl)amino]methyl}benzamide;

N-(3-Pyridinyl)-4-{[(3-thienylsulfonyl)amino]methyl}benzamide;

4-({[(1,2-Dimethyl-1H-imidazol-5-yl)sulfonyl]amino}methyl)-N-(3-pyridinyl)benzamide;

N-(3-pyridinyl)-4-{[(4H-1,2,4-triazol-3-ylsulfonyl)amino]methyl}benzamide; and

N-(3-Pyridinyl)-4-{[(2-furanylsulfonyl)amino]methyl}benzamide.

Also described are compounds of Formula III which bind to GLUT1:

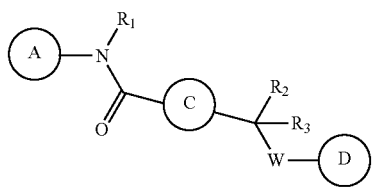

III wherein:

A is a nitrogen-containing heteroaryl ring chosen from pyridinyl, pyrimidinyl, pyrazinyl, quinolinyl, pyrazolyl, imidazolyl, and thiazolyl, each of which is optionally substituted;

$R_1$, $R_2$, and $R_3$ are each independently chosen from hydrogen, optionally substituted alkyl, and optionally substituted alkenyl;

W is chosen from —N(R)SO$_2$R$_X$—, —SO$_2$N(R)R$_X$—, and —N(R)COR$_X$—, wherein each R is independently chosen from hydrogen, alkyl, alkenyl, alkynyl, cycloalkyl, aryl, heterocycloalkyl, and heteroaryl, each of which, except for hydrogen, is optionally substituted; and R$_X$ is an bivalent $C_0$-$C_6$alkylene, bivalent $C_3$-$C_6$cycloalkyl, or phenyl, each of which is optionally substituted;

C is selected from $C_5$-$C_6$cycloalkyl, and phenyl, wherein B is optionally substituted hydrogen, hydroxy, optionally substituted alkyl, optionally substituted alkenyl, optionally substituted alkoxy, optionally substituted cycloalkyl, optionally substituted aryl, optionally substituted heterocycloalkyl, optionally substituted heteroaryl, halo, carboxy, nitro, sulfonyl, sulfinyl, and optionally substituted amino; and D is an optionally substituted heterocycle.

Also provided herein are compounds of Formula IIIA which bind to GLUT1:

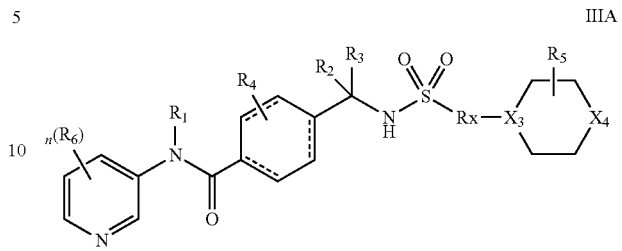

IIIA wherein:

$X_3$ is selected from CH or N;

$X_4$ is selected from O, NH, or NR$_1$;

$R_1$, $R_2$, and $R_3$ are each independently chosen from hydrogen, optionally substituted alkyl, and optionally substituted alkenyl;

$R_4$ and $R_5$ are independently chosen from hydrogen, hydroxy, optionally substituted alkyl, optionally substituted alkenyl, optionally substituted alkoxy, optionally substituted cycloalkyl, optionally substituted aryl, optionally substituted heterocycloalkyl, optionally substituted heteroaryl, halo, carboxy, nitro, sulfonyl, sulfinyl, and optionally substituted amino; for each occurrence, $R_6$ is independently chosen from alkyl optionally substituted with one or more halo, alkoxy, halo, nitro, heterocycloalkyl, and amino optionally substituted with $C(O)R_a$, wherein $R_a$ is chosen from alkyl and optionally substituted alkoxy;

$R_X$ is an bivalent $C_4$alkylene, bivalent $C_6$cycloalkyl, or phenyl, each of which is optionally substituted; and n is 0, 1, or 2.

An illustrative example of compounds of Formula III and IIIA is set forth below:

4-((4-(4-methylpiperazin-1-yl)cyclohexanesulfonamido)methyl)-N-(pyridin-3-yl)benzamide.

Also provided herein are compounds of Formula IV which bind to GLUT1:

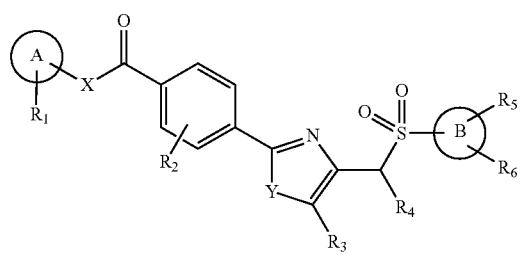

IV wherein

A is a nitrogen-containing heteroaryl ring chosen from pyridinyl, pyrazinyl, and imidazolyl, each of which is optionally substituted;

X is CH$_2$CH$_2$NR, CH$_2$NR, or NR wherein each R is independently chosen from hydrogen, alkyl, alkenyl, alkynyl, cycloalkyl, aryl, heterocycloalkyl, and heteroaryl, each of which, except for hydrogen, is optionally substituted;

$R_1$, $R_2$, $R_3$, and $R_4$ are each independently chosen from hydrogen, alkyl, alkenyl, alkynyl, cycloalkyl, aryl, heterocycloalkyl, and heteroaryl, each of which, except for hydrogen, is optionally substituted;

Y is chosen from O, S, NR; wherein each R is independently chosen from hydrogen, alkyl, alkenyl, alkynyl, cycloalkyl, aryl, heterocycloalkyl, and heteroaryl, each of which, except for hydrogen, is optionally substituted; and B is an optionally substituted aryl ring.

Also provided herein are compounds of Formula IVA which bind to GLUT1:

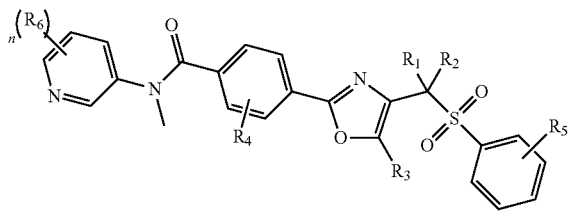

IVA wherein $R_1$, $R_2$, and $R_3$ are each independently chosen from hydrogen, alkyl, alkenyl, alkynyl, cycloalkyl, aryl, heterocycloalkyl, and heteroaryl, each of which, except for hydrogen, is optionally substituted;

$R_4$ and $R_5$ are independently chosen from hydrogen, hydroxy, optionally substituted alkyl, optionally substituted alkenyl, optionally substituted alkoxy, optionally substituted cycloalkyl, optionally substituted aryl, optionally substituted heterocycloalkyl, optionally substituted heteroaryl, halo, carboxy, nitro, sulfonyl, sulfinyl, and optionally substituted amino;

for each occurrence, $R_6$ is independently chosen from alkyl optionally substituted with one or more halo, alkoxy, halo, nitro, heterocycloalkyl, and amino optionally substituted with $C(O)R_a$, wherein $R_a$ is chosen from alkyl and optionally substituted alkoxy; and n is 0, 1, or 2.

Illustrative examples of compounds of Formula IV are set forth below:

4-(5-Methyl-4-{[(4-methylphenyl)sulfonyl]methyl}-1,3-oxazol-2-yl)-N-(3-pyridinyl)benzamide;
4-(5-Methyl-4-{[(4-methylphenyl)sulfonyl]methyl}-1,3-oxazol-2-yl)-N-(4-pyridinyl)benzamide;
N-Methyl-4-(5-methyl-4-{[(4-methylphenyl)sulfonyl]methyl}-1,3-oxazol-2-yl)-N-(3-pyridinyl)benzamide;
4-(5-Methyl-4-{[(4-methylphenyl)sulfonyl]methyl}-1,3-oxazol-2-yl)-N-(2-pyridinylmethyl)benzamide;
4-(5-Methyl-4-{[(4-methylphenyl)sulfonyl]methyl}-1,3-oxazol-2-yl)-N-(3-pyridinylmethyl)benzamide;
4-(5-Methyl-4-{[(4-methylphenyl)sulfonyl]methyl}-1,3-oxazol-2-yl)-N-(4-pyridinylmethyl)benzamide;
N-Methyl-4-(5-methyl-4-{[(4-methylphenyl)sulfonyl]methyl}-1,3-oxazol-2-yl)-N-(3-pyridinylmethyl)benzamide;
4-(5-Methyl-4-{[(4-methylphenyl)sulfonyl]methyl}-1,3-oxazol-2-yl)-N-[2-(3-pyridinyl)ethyl]benzamide;
4-(5-Methyl-4-{[(4-methylphenyl)sulfonyl]methyl}-1,3-oxazol-2-yl)-N-(2-pyrazinylmethyl)benzamide;
N-[(1-Methyl-1H-imidazol-2-yl)methyl]-4-(5-methyl-4-{[(4-methylphenyl)sulfonyl]methyl}-1,3-oxazol-2-yl)benzamide;
N-[(1-Methyl-1H-imidazol-5-yl)methyl]-4-(5-methyl-4-{[(4-methylphenyl)sulfonyl]methyl}-1,3-oxazol-2-yl)benzamide;
4-{5-Methyl-4-[(phenylsulfonyl)methyl]-1,3-oxazol-2-yl}-N-(3-pyridinylmethyl)benzamide;
4-(4-{[(4-Chlorophenyl)sulfonyl]methyl}-5-methyl-1,3-oxazol-2-yl)-N-(3-pyridinylmethyl)benzamide;
4-(4-{[(4-tert-Butylphenyl)sulfonyl]methyl}-5-methyl-1,3-oxazol-2-yl)-N-(3-pyridinylmethyl)benzamide;
4-(4-{[(3,5-Dimethylphenyl)sulfonyl]methyl}-5-methyl-1,3-oxazol-2-yl)-N-(3-pyridinylmethyl)benzamide;
4-(4-{[(4-Bromophenyl)sulfonyl]methyl}-5-methyl-1,3-oxazol-2-yl)-N-(3-pyridinylmethyl)benzamide;
4-(5-Methyl-4-{[(3-methylphenyl)sulfonyl]methyl}-1,3-oxazol-2-yl)-N-(3-pyridinylmethyl)benzamide;
4-(4-{[(4-Methoxyphenyl)sulfonyl]methyl}-5-methyl-1,3-oxazol-2-yl)-N-(3-pyridinylmethyl)benzamide;
4-(5-Methyl-4-{[(3-methoxyphenyl)sulfonyl]methyl}-1,3-oxazol-2-yl)-N-(3-pyridinylmethyl)benzamide;
4-(4-{[(3,4-Dimethoxyphenyl)sulfonyl]methyl}-5-methyl-1,3-oxazol-2-yl)-N-(3-pyridinylmethyl)benzamide;
4-(5-Methyl-4-{[(2,4-dimethylphenyl)sulfonyl]methyl}-1,3-oxazol-2-yl)-N-(3-pyridinylmethyl)benzamide;
4-(4-{[(4-Fluorophenyl)sulfonyl]methyl}-5-methyl-1,3-oxazol-2-yl)-N-(3-pyridinylmethyl)benzamide;
4-[5-Methyl-4-({[4-(4-methyl-1-piperazinyl)phenyl]sulfonyl}methyl)-1,3-oxazol-2-yl]-N-(3-pyridinylmethyl)benzamide;
4-[5-Methyl-4-({[4-(4-morpholinyl)phenyl]sulfonyl}methyl)-1,3-oxazol-2-yl]-N-(3-pyridinylmethyl)benzamide;
4-(4-{[(4-Methylphenyl)sulfonyl]methyl}-1,3-thiazol-2-yl)-N-(3-pyridinylmethyl)benzamide;
4-(5-methyl-4-(phenylsulfonylmethyl)oxazol-2-yl)-N-(pyridin-3-ylmethyl)benzamide; and
4-(5-methyl-4-(tosylmethyl)oxazol-2-yl)-N-(pyridin-3-ylmethyl)benzamide.

Compounds described herein, as well as additional compounds, all useful for the present invention are described in U.S. Application Ser. No. 61/391,958 filed Oct. 11, 2010, U.S. Application Ser. No. 61/277,213, filed Jul. 21, 2009, U.S. Application Ser. No. 61/323,681, filed Apr. 13, 2010, International Application No. PCT/US2010/042742, filed Jul. 21, 2010, and U.S. Application Ser. No. 61/434,976, filed Jan. 21, 2011, all of which are incorporated herein in their entirety by reference for all uses.

In some instances the HIF pathway proficient cell is a neoplastic cell. In some embodiments the neoplastic cell is a cell from a cancer or tumor. Cancers and tumors contemplated for the present invention include hemaetologic cancers, reproductive cancers, brain, spinal and nerve cancers, liver cancer, lung cancers, skin cancer, urogenital cancers, excretory cancers, endocrine cancers and epithelial cancers.

In some embodiments, the cancer or tumor is selected from hematologic cancers, reproductive cancers, brain, spinal and nerve cancers, liver cancer, lung cancers, skin cancer, urogenital cancers, excretory cancers, endocrine cancers and epithelial cancers or a combination thereof.

Hemaetologic cancers can include leukemia and lymphoma. In some embodiments, the hemaetologic tumor is selected from Acute Lymphoblastic Leukemia (ALL), acute myeloid leukemia (AML), chronic myeloid leukemia, chronic lymphocytic leukemia (CLL), Non-Hodgkin's Lymphoma. Acute Lymphoblastic Leukemia (ALL) can include for example CCRF-CEM and MOLT-4 cell types. Acute myeloid leukemia (AML) can include for example the HL-60 (TB) cell type. Chronic myeloid leukemia can include for example the K-562 cell type. Non Hodgkin's Lymphoma can include for example SR cell type.

Reproductive cancers can include breast cancers and carcinomas. Breast carcinoma can include for example T-47D, BT-549, HS 578T, MDA-MB-468, BT-549, HS 578T and MDA-MB-435 cell types.

Brain, spinal and nerve cancers can include glioma and glioblastoma. Glioma can include for example SF-268, SF-539, SNB-19, SNB-75, U251 and SF-295 cell types.

Liver cancer can include hepatocellular cancer and hepatocellular carcinoma. Hepatocellular cancer can include for example the HEPG2 cell type.

Lung cancer can include lung adenocarcinoma, lung brochoalveolar carcinoma, Lung carcinoma, Lung large cell carcinoma and lung squamous cell carcinoma. Lung adenocarcinoma can include for example HOP-62, NCl—H23, NCl—H522 and EKVX cell types. Lung brochoalveolar carcinoma can include for example NCl—H322M cell type. Lung carcinoma can include for example A549 cell type. Lung large cell carcinoma can include for example the HOP-92 cell type. Lung squamous cell carcinoma can include for example the NCl—H226 cell type.

Skin cancer can include melanoma and myeloma. Melanoma can include for example M14, SK-MEL-5, LOX IMV1, MALME-3M, UACC-257, UACC-62 and MDA-MB-435 cell types. Myeloma can include for example the RPMI-8226 cell type.

Urogenital cancers can include ovarian, uterine and bladder cancers and carcinomas. Ovarian carcinoma can include for example A2780, OVCAR-3, OVCAR-4, OVCAR-8, SK-OV-3, CP70, HEYA8, IGR-OV1, OVCAR-5 and SKOV3ip1 cell types.

Excretory cancers can include kidney, renal and colorectal cancers and carcinomas. Colorectal cancers can include colorectal adenocarcinoma and colorectal carcinoma. Colorectal adenocarcinoma can include for example COLO 205, HCC-2998, SW480, SW-620, RKO, COLO 205, HCC-2998, SW480, SW-620, HCT-116, HCT-15 and DLD1 cell types. Colorectal carcinoma can include for example HT29 and KM12 cell types. Renal cell cancer can include for example SN12C, RXF 393, SN12, TK-10 and UO-31 cell types. Renal cell carcinoma can include for example CAKI-1, 786-0, 786T2R, RCC4, 786-0, 786T2R and A498 cell types.

Endocrine cancers can include pancreatic, thyroid, parathyroid, pituitary and parathyroid cancers and carcinomas. Pancreatic carcinoma can include for example MiaPaCa and panc1 cell types.

Epithelial cancers can include squamous carcinomas of the head and neck. Squamous head and neck carcinoma can include for example HSC4 and SCC1 cell types.

Table 1 lists specific cell types and suitabilty for treatments using methods of the present invention.

| CANCER TYPE | CELL TYPE | SENSITIVITY TO GLUT1 INHIBITORS |
|---|---|---|
| Acute Lymphoblastic Leukemia | CCRF-CEM | sensitive |
| Acute Lymphoblastic Leukemia | MOLT-4 | sensitive |
| acute myeloid leukemia | HL-60(TB) | sensitive |
| Breast carcinoma | T-47D | sensitive |
| Breast carcinoma | BT-549 | intermediate |
| Breast carcinoma | HS 578T | intermediate |
| Breast carcinoma | MDA-MB-468 | intermediate |
| chronic myeloid leukemia | K-562 | sensitive |
| Colorectal adenocarcinoma | COLO 205 | sensitive |
| Colorectal adenocarcinoma | HCC-2998 | sensitive |
| Colorectal adenocarcinoma | SW480 | sensitive |
| Colorectal adenocarcinoma | SW-620 | sensitive |
| Colorectal adenocarcinoma | RKO | sensitive |
| Colorectal adenocarcinoma | HCT-116 | intermediate |
| Colorectal adenocarcinoma | HCT-15 | intermediate |
| Colorectal adenocarcinoma | DLD1 | intermediate |
| colorectal carcinoma | HT29 | intermediate |
| colorectal carcinoma | KM12 | intermediate |
| Glioma | SF-268 | sensitive |
| Glioma | SF-539 | sensitive |
| Glioma | SNB-19 | sensitive |
| Glioma | SNB-75 | sensitive |
| Glioma | U251 | sensitive |
| Glioma | SF-295 | intermediate |
| Hepatocellular Cancer | HEPG2 | intermediate |
| Lung adenocarcinoma | HOP-62 | sensitive |
| Lung adenocarcinoma | NCI-H23 | sensitive |
| Lung adenocarcinoma | NCI-H522 | sensitive |
| Lung adenocarcinoma | EKVX | intermediate |
| Lung brochoalveolar carcinoma | NCI-H322M | sensitive |
| Lung Carcinoma | A549 | intermediate |
| Lung large cell carcinoma | HOP-92 | intermediate |
| Lung Squamous cell carcinoma | NCI-H226 | intermediate |
| Melanoma | M14 | sensitive |
| Melanoma | SK-MEL-5 | sensitive |
| Melanoma | LOX IMV1 | intermediate |
| Melanoma | MALME-3M | intermediate |
| Melanoma | UACC-257 | intermediate |
| Melanoma | UACC-62 | intermediate |
| Melanoma or Breast | MDA-MB-435 | intermediate |
| Myeloma | RPMI-8226 | sensitive |
| Non Hodgkin's Lymphoma | SR | intermediate |
| Ovarian carcinoma | A2780 | sensitive |
| Ovarian carcinoma | OVCAR-3 | sensitive |
| Ovarian carcinoma | OVCAR-4 | sensitive |
| Ovarian carcinoma | OVCAR-8 | sensitive |
| Ovarian carcinoma | SK-OV-3 | sensitive |
| Ovarian carcinoma | CP70 | intermediate |
| Ovarian carcinoma | HEYA8 | intermediate |
| ovarian carcinoma | IGR-OV1 | intermediate |
| Ovarian carcinoma | OVCAR-5 | intermediate |
| Ovarian carcinoma | SKOV3ip1 | intermediate |
| Pancreatic carcinoma | MiaPaCa | sensitive |
| Pancreatic carcinoma (epithelial) | panc1 | intermediate |
| Prostate carcinoma | DU-145 | intermediate |
| Renal Cell Cancer | SN12C | sensitive |
| Renal Cell Cancer | RXF 393 | intermediate |
| Renal Cell Cancer | SN12 | intermediate |
| Renal Cell Cancer | TK-10 | intermediate |
| Renal Cell Cancer | UO-31 | intermediate |
| Renal cell carcinoma | CAKI-1 | intermediate |
| Renal cell Carcinoma (clear cell, VHL | 786-0 | sensitive |
| Renal cell Carcinoma (clear cell, VHL | 786T2R | sensitive |
| Renal cell Carcinoma (clear cell, VHL | RCC4 | sensitive |
| Renal cell Carcinoma (clear cell) | A498 | intermediate |
| Squamous carcinomal Head and | HSC4 | sensitive |

According to the present invention, Inhibiting cell growth or proliferation can include decreasing the rate of growth of cells, decreasing the number of cells, decreasing the rate of cellular division, as well as causing cell death. Inhibiting cellular growth can be observed as decreased tumor size, decreased tumor number, decreased metastasis size and/or decreased metastasis number. A decrease in tumor size can occur due to a decrease in the number of cells in the tumor, a decrease in the volume of the tumor or a decrease in the growth rate of the cells within the tumor. A decrease in the tumor size can also occur due to an increase in the rate of death of cells within the tumor. In some embodiments, the inhibition of cell growth can include cellular death by apoptosis or necrosis.

According to another aspect of the present invention, it provides methods for treating neoplasia via administering to a subject with HIF pathway proficient with the therapeutic entities of the present invention, e.g., therapeutic entities that inhibit one or more activities of GLUT1. According to the present invention, neoplasia includes any abnormal growth or cell proliferation, e.g., uncoordinated with the proliferation of the tissues (normal) around it. In one embodiment, neoplasia includes any cancer or tumor growth in a subject. In another embodiment, neoplasia includes any pre-cancerous or pre-tumor growth in a subject. In yet another embodiment, neoplasia includes any solid or circulating cancer or tumor growth in a subject. In still another embodiment, neoplasia includes any abnormal growth that is capable of metastasizing or spreading to other locations of the subject. Examples of neoplasia include, but are not limited to carcinoma, sarcoma, blastoma, lymphoma, leukemia, and germ cell tumors. In some embodiments, neoplasia includes head and neck, skin, colon, oral, glioblastoma, glioma, breast, laryngeal, esophageal, endothelial, endometrial, ovarian, lung, urogenital, rectal, prostate, kidney, melanoma and renal.

The methods of the present invention also contemplate the use of the therapeutic entity as a treatment, for example for the treatment of neoplasia in a subject. Such methods comprise administering the therapeutic entity to a subject known or determined to be HIF pathway proficient. The therapeutic entity or a pharmaceutically acceptable salt thereof can be formulated by a variety of methods for administration to a subject, including as a pharmaceutically acceptable salt. Administration can be by a variety of methods including oral adminsitration, intraperitoneal injection, intramuscular injection, intradermal injection, parenteral, topical, intravenous, intratumoral, oral, subcutaneous, intraarterial, intracranial or intranasal, as well as others known in the art. Further, the compound can be administered at a variety of concentrations and methods for determining such routes, dosages and methods for administration could be readily determined by one skilled in the medical arts. In some embodiments, the present invention provides methods for treating neoplasia comprising administering to a subject determined to be HIF pathway proficient a therapeutic entity, wherein the therapeutic entity inhibits the activity of GLUT1 and wherein the therapeutic entity preferentially inhibits the growth or proliferation of neoplastic cells versus normal cells in the subject.

The methods of the present invention also provide methods for the treatment of neoplasia wherein the therapeutic entity inihibits GLUT1 and inhibits growth or proliferation of neoplastic versus normal cells. Such methods include knowing or determining whether a subject is HIF pathway proficient prior to or during treatment. According to the present invention, determining whether a subject is HIF pathway proficient can be carried out by any suitable means known in the art, e.g., by clinician asking another entity and/or person to test whether the cells from a subject are HIF pathway proficient or by a clinician studying the test results provided by another entity or person regarding HIF pathway proficiency. For example, such methods for determining HIF pathway proficiency can include but are not limited to determining that the cell is glycolysis dependant, the cell has a genetic condition including a mutation in the HIF pathway, increased HIF stabilization, reduced mitochondrial function, aerobic glycolysis, PDK1 up-regulation, PDH down-regulation, MXI1 up-regulation or MYC down-regulation, as described herein. In some embodiments, the methods of the present invention provide methods for treating neoplasia comprising determining whether a subject is HIF pathway proficient, and administering to a subject that is determined to be HIF pathway proficient a therapeutic entity, wherein the therapeutic entity inhibits the activity of GLUT1.

The methods of the present invention further contemplate the use of one or more therapeutic entities to target both GLUT1 and HIF pathway, e.g., one or more genes or proteins associated with HIF pathway including those listed herein as well as others known to be involved in the HIF pathway. Such methods include the use of the therapeutic entity to inhibit growth or proliferation of a cell by inhibiting the activity of GLUT1 and affecting the activity of HIF pathway, e.g., to cause HIF pathway proficient, so that the therapeutic entity preferentially inhibits the growth or proliferation of neoplastic versus normal cells. Affecting the activity can include increasing or decreasing the activity, expression, stabilization or degradation of genes and gene products within the HIF pathway, e.g., cause HIF pathway proficient. In some embodiments, the methods of the present invention include methods for inhibiting cell growth or proliferation comprising contacting a cell with a therapeutic entity, wherein the therapeutic entity inhibits the activity of GLUT1 and the activity of a gene in HIF pathway, e.g., to cause HIF proficient, and wherein the therapeutic entity preferentially inhibits the growth or proliferation of neoplastic cells versus normal cells.

The methods of the present invention additionally provide methods for monitoring the effectiveness of treatment of a subject with a therapeutic entity where the subject is HIF pathway proficient. Such methods for monitoring effectiveness include monitoring the utilization of glucose in order to determine that the therapy is active in a subject, for example by PET scan staging of tumor state, or by lactography (See, e.g., Larson, S. M., and Schoder, H. *Curr Opin Urol.*, 18:65-70 (2008) and Korf et al., *International Journal of Biochemistry*, Vol. 22(12): 1371-1378 (1990)) or by examining GLUT1 activity. PET scanning can be employed to detemine whether glucose uptake is inihbited, wherein such inihibition is indicative of effectiveness of treatment with the therapeutic entity. Methods for monitoring the effectiveness of treatment of a subject with a therapeutic entity can further include determining HIF pathway proficiency in a subject. Treatments can then be approriately modified, for example by increasing or decreasing adminsitration dosage, administration timing, and/or adminsitration frequency, as deteremined by one skilled in the medical arts. Methods for determining HIF pathway proficiency can include but are not limited to determining that the cell is glycolysis dependant, has a genetic condition such as a mutation in the HIF pathway, has increased HIF stabilization, has reduced mitochondrial function, has aerobic glycolysis, has PDK1 up-regulation, has PDH down-regulation, has MXI1 up-regulation and/or has MYC down-regulation, as described herein. In some embodiments, the methods of the present invention include methods for monitoring the effectiveness of a treatment comprising monitoring the utilization of glucose by neoplastic cells versus normal cells upon administering a therapeutic entity to a subject determined to be HIF pathway proficient, wherein the therapeutic entity inhibits the activity of GLUT1.

EXAMPLES

Example 1

Synthetic Lethal Targeting of Glucose Transport in Renal Carcinoma: Inhibition of Glucose Transport in Mutant VHL Cells

SUMMARY

Identifying new molecular targeted therapies that specifically kill tumor cells while sparing normal tissue is the next major challenge of cancer research. Using a high-throughput chemical synthetic lethal screen, we identified a small molecule compound, STF-31, that exploits the loss of von Hippel-Lindau (VHL) tumor suppressor gene, which occurs in approximately 80% of renal carcinomas. STF-31 selectively kills cells with mutant VHL but not cells with wild-type VHL by specifically targeting glucose uptake via GLUT1 in VHL-deficient tumors, which are dependent on glycolysis for ATP production. Treatment with STF-31 inhibits the growth of VHL-deficient tumors by binding GLUT1 directly and impeding glucose uptake in vivo without toxicity to normal tissue. Activity of STF-31 in these experimental renal cell tumors can be monitored by [$^{18}$F]-fluorodeoxyglucose (FDG) uptake by microPET imaging and therefore may be readily translated clinically to human tumors. STF-31 is a particularly attractive targeted therapy for the treatment of renal carcinoma due to its unique mechanism of inhibiting glucose uptake and the ability to measure tumor response by FDG-PET.

Furthermore, synthetic lethality is a therapeutically advantageous approach to drug discovery and is particularly suited to developing therapeutics to treat cancers. It describes a genetic interaction whereby the combination of mutation and/or inhibition of two genes leads to tumor cell death. If only one of these two genes is altered, there are no deleterious effects. In the vast majority of renal carcinomas, the VHL tumor suppressor gene is inactivated, driving growth and expansion. We exploit a characteristic of VHL-deficient cells, namely reliance on GLUT1 and aerobic glycolysis. In this example, a small molecule is described that impairs glucose transport in VHL-deficient cells, but not in cells with wild-type VHL, resulting in specific killing of renal carcinoma cells. The potential to target glucose uptake in VHL-deficient tumors therapeutically with the use of small molecules provides a new way to treat metastatic renal carcinoma.

Introduction

Conventional chemotherapeutic agents were identified only by their ability to kill rapidly proliferating cells and therefore cannot distinguish between normal, healthy dividing cells and tumor cells. For this reason, standard agents have low therapeutic indices and are often limited by their severe toxicity to normal tissue. While many solid tumors respond to different combinations of cytotoxic chemotherapies, kidney cancer is a particularly intractable disease. Renal cell carcinoma (RCC), the most common type of kidney cancer, has proven to be particularly challenging, resistant to both radiation therapy and standard systemic chemotherapies (Atkins, et al., *Clin Cancer Res.*, 10:6277S-6281S. (2004); Motzer, R. J., and Russo, P., *J Urol.*, 163:408-417 (2000)). To date, immunotherapy using interferon or interleukin-2 has had mild success with responses in less than 10% of patients with metastatic RCC (Rosenberg, et al., *Ann Surg.*, 228:307-319 (1998)). The recent development of anti-angiogenic therapies sunitinib (Sutent) and sorafenib (Nexavar) is encouraging although these agents are not curative (Ahmad, T., and Eisen, T., *Clin Cancer Res.*, 10:6388S-6392S (2004); Motzer, et al., *J Clin Oncol.*, 24:16-24 (2006)). The targeting of receptor tyrosine kinases, which is not specific to the development of RCC, has become the standard of care for advanced RCC (Rathmell, et al., *Curr Opin Oncol.*, 19:234-240 (2007)). One key distinguishing feature in RCC is the loss of function of the VHL tumor suppressor gene, an essential and frequent mutation in the development of RCC. In order to specifically target RCC cells without toxicity to normal cells, we have employed a synthetic lethal approach, seeking to identify compounds that exhibit selective cytotoxicity to cells that have lost functional VHL.

The concept of synthetic lethality, or conditional genetics, describes the genetic interaction of two genes, both involved in a cellular process. When either gene is mutated alone, the cell remains viable. However, the combination of mutations in these two genes results in cell death (Hartwell, et al., Science, 278:1064-1068 (1997)). In the case of chemical synthetic lethality, the first mutation is essential to the development of cancer, while a second gene is inhibited by a small molecule, resulting in cytotoxic cell death (Kaelin, W. G., Jr., *Nat Rev Cancer*, 5:689-698 (2005); Sutphin, et al., *Cancer Res.*, 67:5896-5905 (2007)). This approach is particularly attractive because it should not affect normal, non-cancerous tissue.

Results

Chemical Synthetic Lethal that Targets Loss of VHL in Renal Carcinoma

Figure 5:
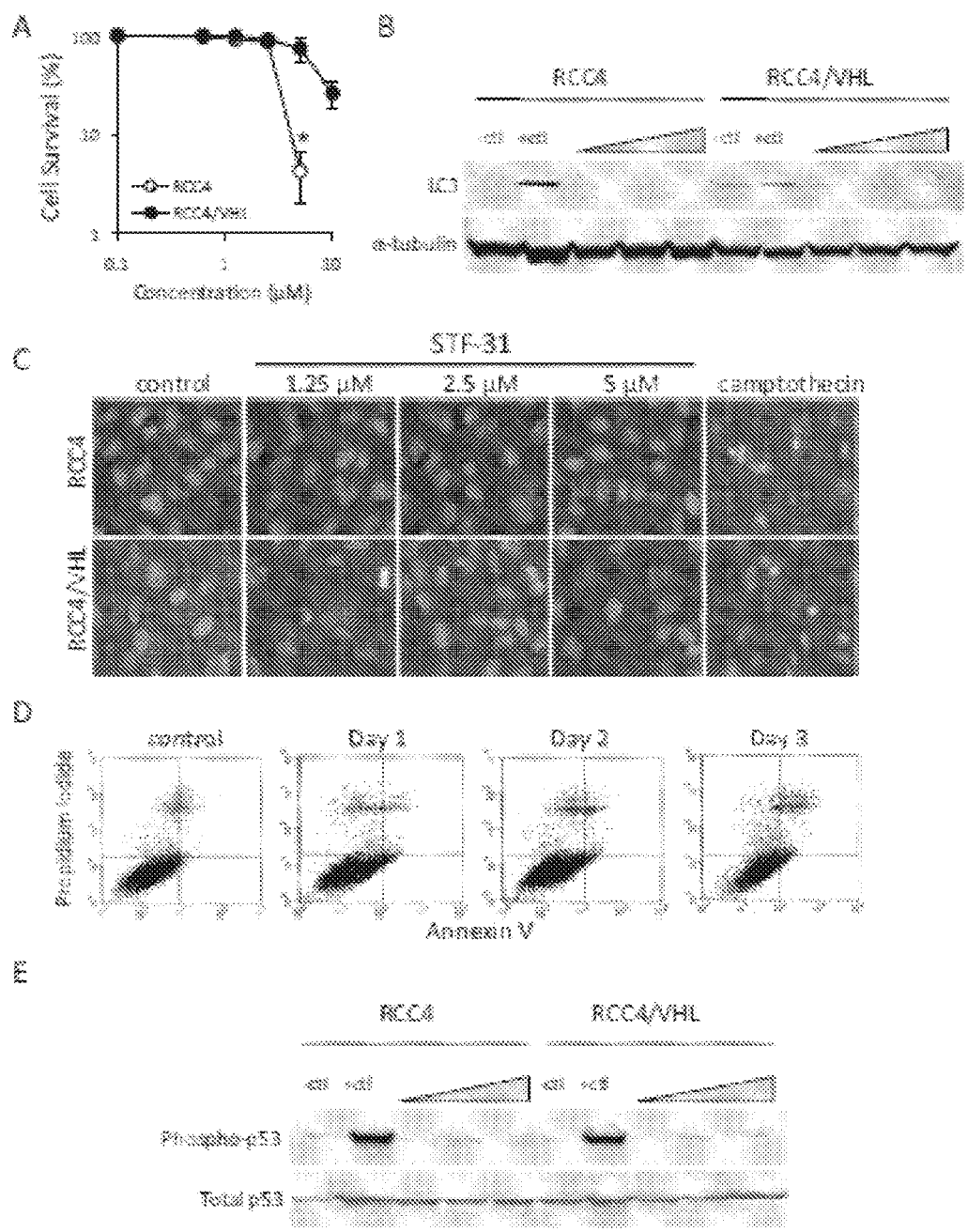
FIG. 5. STF-31 does not induce autophagy, apoptosis, or DNA damage. (A) Clonogenic survival of RCC4 and RCC4/VHL treated with STF-29497 (5 µM)($*p<0.05$). All error bars represent the standard error of the mean. (B) STF-31 does not induce autophagy. RCC4 and RCC4/VHL cells were treated with increasing concentrations of STF-31 (1.25, 2.5 and 5 µM), a negative control (DMSO) and a positive control (STF-62247). Cells were lysed and probed for LC3, a marker of autophagy, or a-tubulin (loading control). (C) STF-31 does not induce apoptosis. RCC4 and RCC4/VHL cells were treated with vehicle, increasing concentrations of STF-31, and camptothecin. Cells were stained with DAPI and nuclear condensation was examined by fluorescence microscopy. (D) RCC4 cells were treated with STF-31 (5 µM) for the indicated time and stained with Annexin V and propidium iodide and subjected to FACS analysis. (E) STF-31 does not induce DNA damage. RCC4 and RCC4/VHL cells were subjected to increasing concentrations of STF-31 (1.25, 2.5, and 5 µM), a negative control (DMSO), and a positive control (doxorubicin). Cells were lysed and subjected to Western blot with the indicated antibodies.
Figure 6:
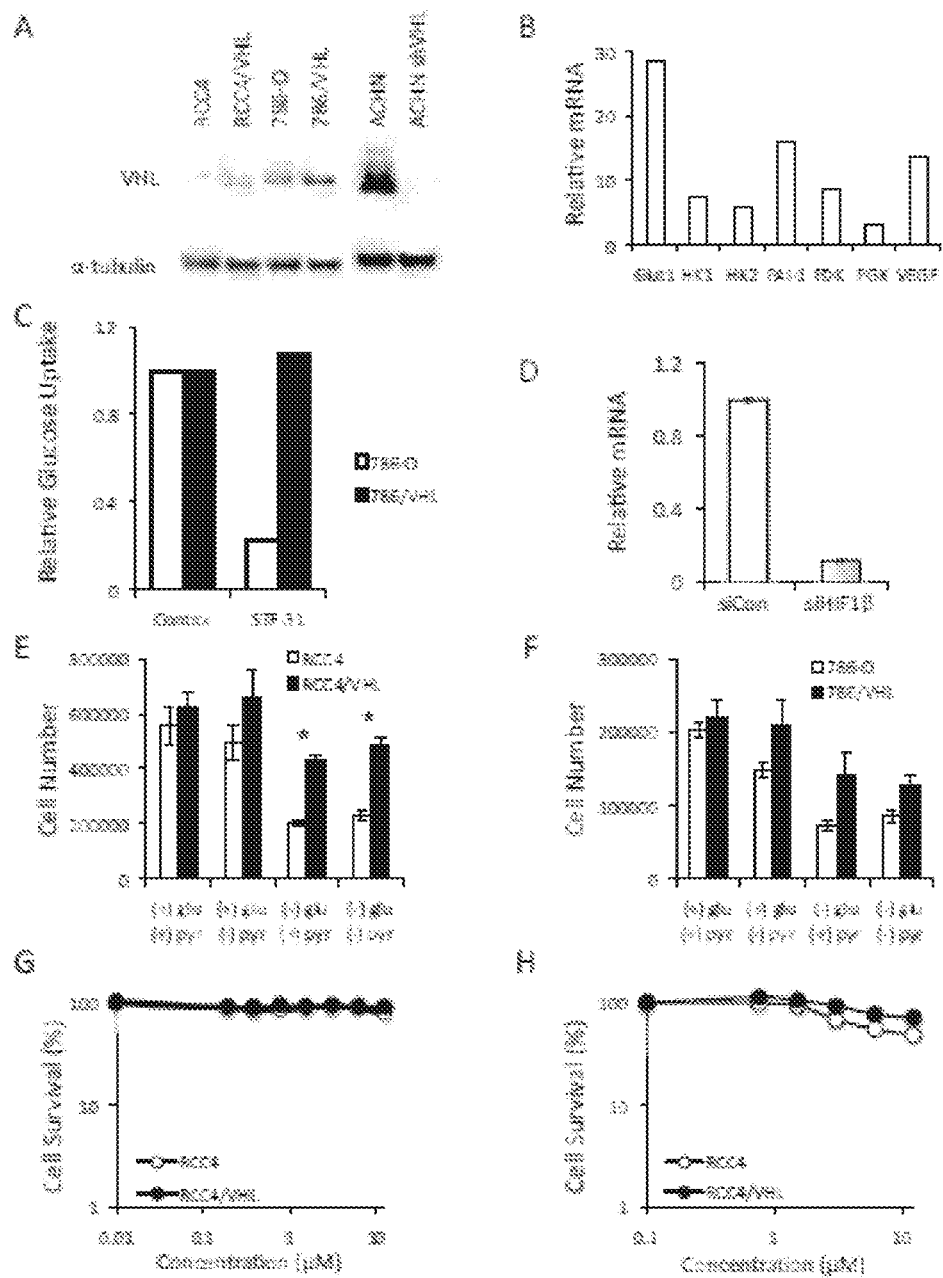
FIG. 6. VHL-deficient renal carcinomas are more sensitive to glucose deprivation compared to RCCs with wild-type VHL. (A) Western blot of VHL confirming overexpression in RCC4/VHL and 786/VHL cells and knockdown of VHL in ACHN shVHL. α-tubulin is used as a loading control. (B) Relative mRNA expression levels for different genes involved in glucose metabolism in RCC4 cells relative to RCC4/VHL cells. (C) Glucose uptake is impaired by STF-31 (5 µM) in 786-O cells, which are deficient in VHL, but not 786/VHL, which have wild-type VHL restored. (D) Quantitative RT-PCR confirming knockdown of HIF-1 R in RCC4 cells, following transfection with indicated siRNA. (E) VHL mutant RCC4 cells are more sensitive to glucose deprivation than RCC4/VHL. Cells were grown in media lacking glucose and/or pyruvate for 6 days (*p<0.005). (F) VHL mutant 786-O cells are more sensitive to glucose deprivation than 786/VHL cells (*p<0.05). (G) XTT assay of RCC4 and RCC4/VHL cells grown in the presence of 2-deoxyglucose. (H) Clonogenic survival assay of RCC4 and RCC4/VHL cells grown in the presence of 2-deoxyglucose.

In order to discover classes of drugs that would selectively target RCC, we screened approximately 64,000 compounds to identify small molecules that function in a synthetic lethal manner to the loss of VHL. We employed multiple RCC cell lines with naturally occurring VHL mutations and, as a negative control, their genetically matched counterparts with reintroduced wild-type VHL. These matched cell lines, engineered to stably express enhanced yellow fluorescent protein, were treated with a small molecule library at a concentration of 10-20 µM for four days. Fluorescence was measured on day four as a surrogate marker for viability and growth. From this fluorescent-based cell assay, two classes of drugs exhibited toxicity to cells that had lost VHL, but were relatively non-toxic to cells with functional VHL. The first class, typified by STF-62247, belongs to the family of pyridyl anilino thiazoles (PATs) that induce autophagy in VHL-deficient RCCs, leading to cell death (Hay, et al., *J Med Chem* (2009); Turcotte, et al., *Cancer Cell* 14:90-102 (2008)). Here we characterize the selective cytotoxicity of a second class, which includes STF-29 and STF-31, members of a family of 4-(phenylsulfonamido)-N-(pyridin-3-yl)benzamides (PPBs). Both short-term cell viability and long-term survival assays were used to validate the primary screen (FIGS. 1A and 1B). Cell viability was measured by metabolism of 2,3-bis[2-methoxy-4-nitro-5-sulfophenyl]-2H-tetrazolim-5-carboxanilide (XTT) after four days of treatment with STF-29 and STF-31. We observed a significant decrease in the number of RCC4 cells that had lost VHL compared to their wild-type counterparts (RCC4/VHL) in a concentration-dependent manner (FIGS. 1A and 6A). Clonogenic survival confirmed that these PPBs were specifically toxic to RCC4 cells while the RCC4/VHL cells were relatively unaffected (FIGS. 1B, 1C, and 5A). Approximately 80% of RCC4 cells treated with STF-31 were killed following treatment whereas RCC4/VHL cells treated under the same conditions were largely able to recover (FIG. 1D). To corroborate the VHL-dependence of PPB resistance, we examined a cell line, ACHN, which normally maintains functional VHL (FIG. 6A). We found that only the ACHN renal carcinoma cells where VHL expression was silenced by shRNA were sensitive to STF-31 (FIG. 1E). Thus, our chemical synthetic screening using a fluorescent, cell-based assay has identified compounds that are specifically cytotoxic to cells that have impaired VHL function.

STF-31 does not Induce Autophagy, Apoptosis, or DNA Damage

Having previously demonstrated a selective sensitivity of VHL-deficient cells to autophagic cell death, we next sought to determine whether STF-31 acts by the same mechanism or whether this small molecule targets a different pathway. Treatment with STF-31 did not induce any morphologic or biochemical features of autophagy, such as intracellular accumulation of vacuoles or LC3 processing (lipidated LC3-II) (FIG. 5B). Incubation of VHL-deficient and isogenic matched wild-type VHL RCCs with STF-31 showed no nuclear condensation in either cell line (FIG. 5C), nor an increase in either propidium iodide or annexin V staining (FIG. 5D), suggesting that STF-31 is not killing these cells by apoptosis. STF-31 did not increase total p53 or phospho-p53 levels, also indicating that STF-31 does not induce a DNA damage response in treated cells (FIG. 5E). However, RCC cells without VHL undergo a necrotic cell death in response to STF-31 as measured by the ability of the cells to exclude trypan blue, an indicator of cell membrane integrity. Treatment with STF-31 resulted in greater than 80% of RCC4 cells exhibiting necrotic cell death, while RCC4/VHL cells were relatively insensitive (FIG. 1F). Taken together, these results indicate that STF-31 is synthetic lethal to the loss of VHL by causing a necrotic cell death. These results also demonstrate that STF-31 acts in a manner distinct from the autophagic cell death pathway we previously described for STF-62247 (Turcotte, et al., *Cancer Cell*, 14:90-102 (2008)).

Toxicity of STF-31 is Dependent on HIF

The hypoxia-inducible factor (HIF) family of transcription factors are VHL targets and we next examined whether toxicity was HIF-dependent (Iliopoulos et al., *Nat Med.*, 1: 822-826 (1995); Maxwell et al., *Nature*, 399:271-275 (1999); Zimmer et al., *Mol Cancer Res.*, 2:89-95 (2004)). A non-degradable, constitutively active HIF was overexpressed in RCC4/VHL cells. Two individual HIF-overexpressing clones were tested for their sensitivity to STF-31 (Sutphin et al., Cancer Res 67:5896-5905 (2007)). Ectopic expression of HIF in cells with wild-type VHL sensitized these cells to STF-31 treatment, indicating that deregulated HIF expression in VHL-deficient cells is responsible for their selective cytotoxicty to STF-31 (FIG. 1G). These data indicate that STF-31 represents a new class of drugs that function in a synthetic lethal manner to VHL mutation, preferentially targeting VHL-deficient cells. Furthermore, the sensitivity of RCCs that lack functional VHL to STF-31 is directly linked to the aberrant up-regulation of HIF.

Synthetic Lethal Interaction Between Glucose Metabolism and VHL-Deficiency

Figure 2:
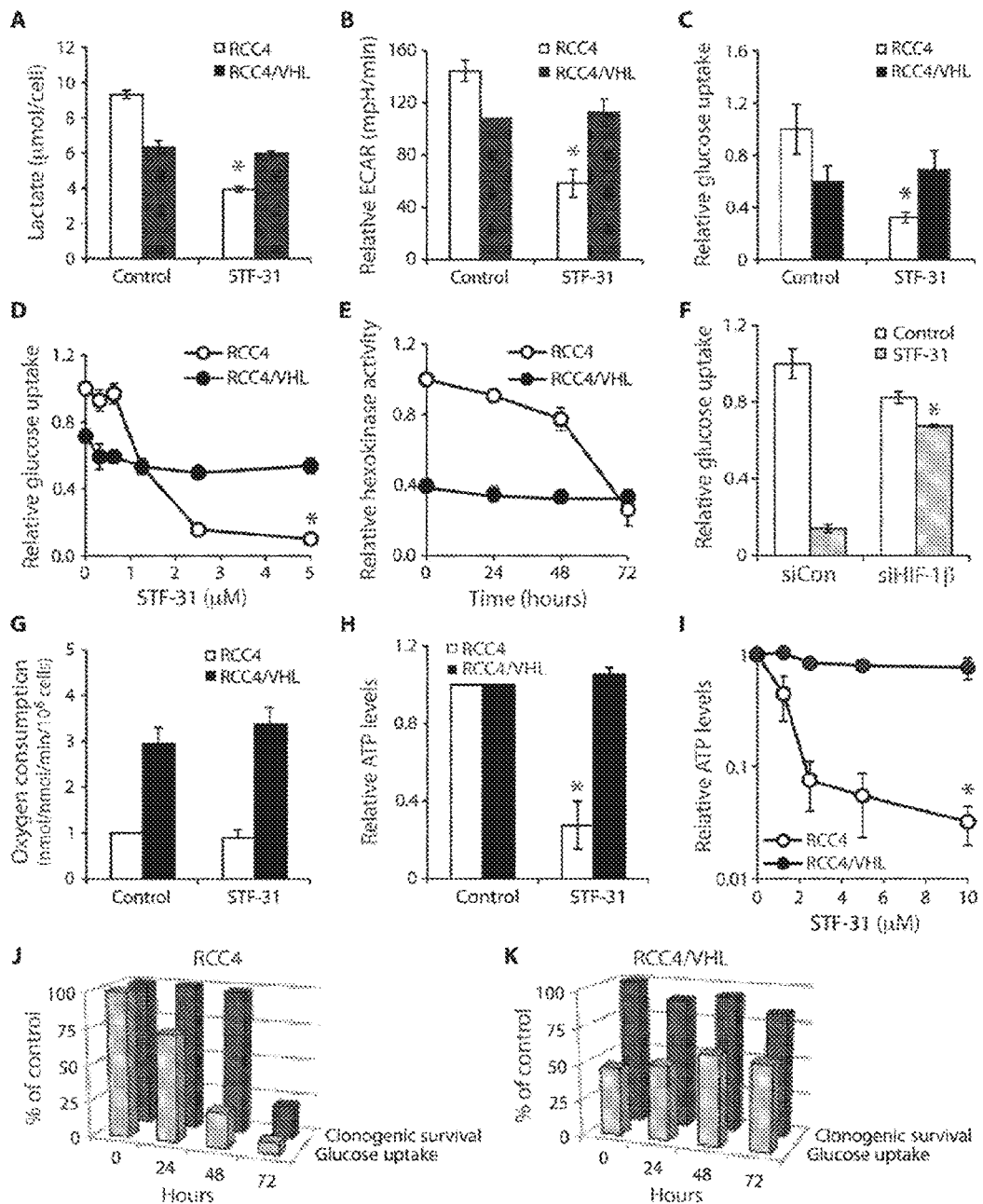
FIG. 2. STF-31 inhibits glucose metabolism in VHL-deficient cells. (A) Lactate (mmol/cell), which is converted from pyruvate, the end product of glycolysis, in RCC4 and RCC4/VHL cells treated with either vehicle or STF-31 (5 mM) ($*P<0.01$). (B) Relative extracellular acidification rate (ECAR) (mpH/min) of VHL-deficient cells and cells with wild-type VHL in response to STF-31 (5 mM) for 48 hours. Cells were stained with crystal violet and absorbance was measured for normalization ($*P<0.0005$). (C) Relative glucose uptake after treatment with STF-31 (5 mM). Counts are normalized to cell number ($*P<0.000005$). (D) Effect of STF-31 concentration on glucose uptake ($*P<0.00005$). (E) Effect of STF-31 on hexokinase activity in whole-cell lysates after STF-31 treatment (5 mM). (F) Effect of STF-31 (5 mM) on glucose uptake in RCC4 cells transfected with small interfering RNA (siRNA) to HIF-1b ($*P<0.05$). (G) Effect of STF-31 (5 mM) on oxygen consumption (nmol/min/106 cells). (H) Effect of STF-31 (5 mM) on relative ATP levels in cells with and without VHL ($*P<0.005$). (I) Effect of STF-31 on ATP levels in cells with and without VHL ($*P<0.01$). (J) Effect of STF-31 (5 mM) on glucose uptake and clonogenic cell survival in cells without VHL up to 72 hours. (K) Effect of STF-31 (5 mM) on glucose uptake and clonogenic cell survival in cells with VHL up to 72 hours. All error bars represent the SEM (n=3).

HIF is important to adapting to low oxygen conditions through the transcription of many genes, including those involved in glucose metabolism. It was hypothesized that STF-31 might inhibit metabolic pathways, leading to necrotic cell death. To examine whether this compound alters glycolysis, intracellular lactate, which is rapidly converted from the glycolysis end product pyruvate, and extracellular acidification were measured. Baseline levels of glycolysis were lower in wild-type VHL cells compared to VHL-deficient cells (FIGS. 2, A and B), likely a result of the constitutive expression of HIF and subsequent overexpression of glucose transporters and glycolytic enzymes in the latter. Treatment with STF-31 significantly inhibited lactate production and extracellular acidification in VHLdeficient cells by about 60% compared to control-treated cells (FIGS. 2, A and B). Treatment with STF-31 did not alter glycolysis in cells with wild-type VHL cells (FIGS. 2, A and B). These results suggest that the selective toxicity of STF-31 is a consequence of the dependence of RCCs on glycolysis and/or a preferential targeting of pathways needed for glycolysis.

STF-31 Inhibits Glucose Uptake

Figure 7:
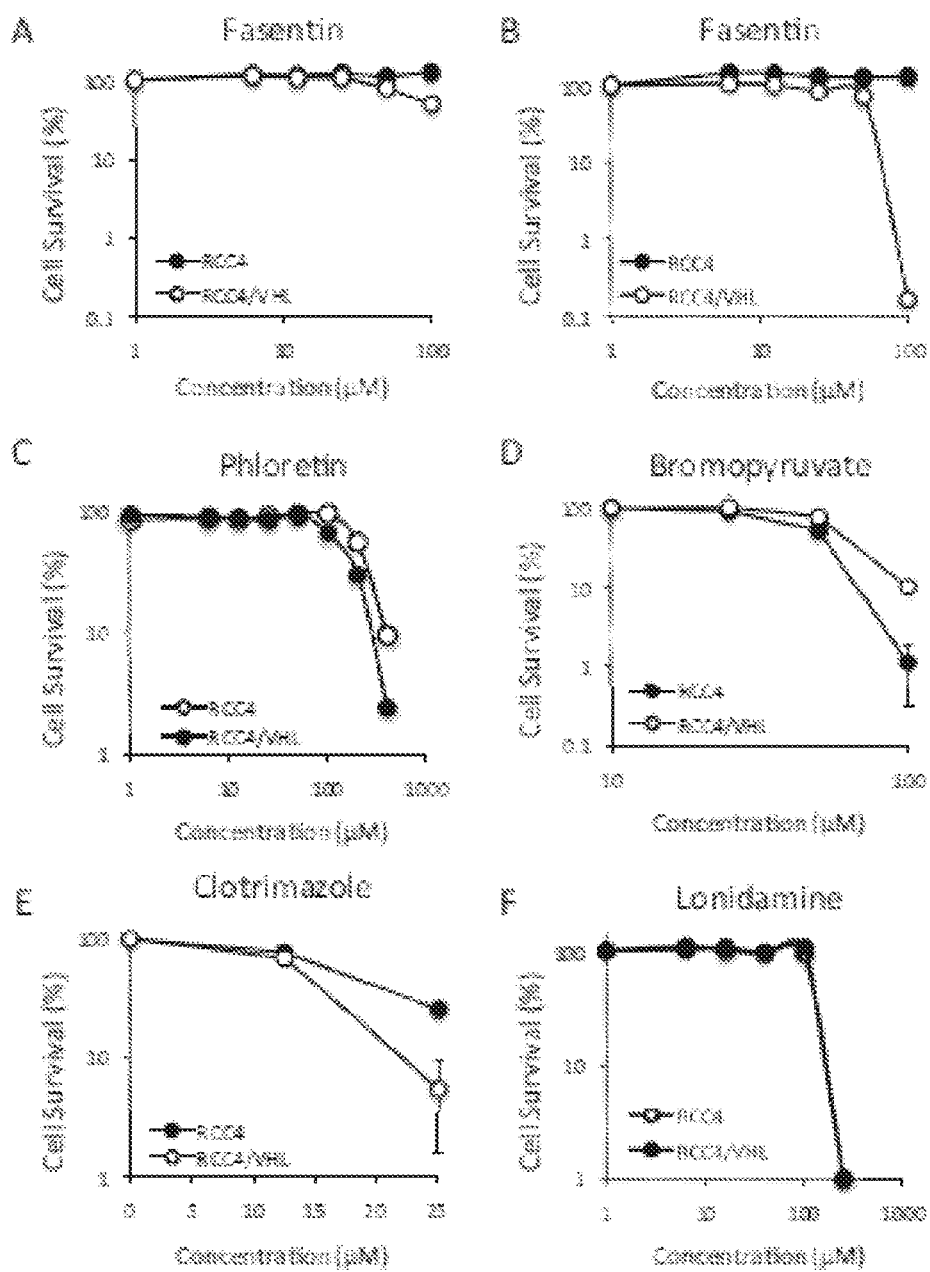
FIG. 7. Other hexokinase and glucose transporter inhibitors do not affect cell survival. (A) XTT assay of RCC4 and RCC4/VHL cells grown in the presence of fasentin. (B) Clonogenic survival of RCC4 and RCC4/VHL cells grown in the presence of fasentin. (C) XTT assay of RCC4 and RCC4/VHL cells grown in the presence of phloretin. (D) Clonogenic survival of RCC4 and RCC4/VHL cells grown in the presence of bromopyruvate. (E) Clonogenic survival of RCC4 and RCC4/VHL cells grown in the presence of clotrimazole. (F) Clonogenic survival of RCC4 and RCC4/VHL cells grown in the presence of lonidamine.

We then examined whether this decrease in glycolysis in response to STF-31 was due to a decrease in glucose uptake or whether STF-31 inhibited a particular glycolytic enzyme. To test this, we measured glucose uptake using 2-deoxy-D-[$^3$H] glucose, a non-hydrolyzable, radioactive glucose analog. STF-31 impaired glucose uptake in RCC4 and 786-O cells but not in the matched isogenic cells expressing wild-type VHL (FIGS. 2B, 6A, and 6C). RCC4/VHL cells had lower baseline levels of glucose uptake compared to RCC4 cells and were unaffected by treatment with STF-31. Furthermore, STF-31 inhibited glucose uptake in RCC4 cells in a dose-dependent manner, but glucose uptake in RCC4/VHL cells were relatively stable with increasing concentrations of STF-31 (FIG. 2C). Because the phosphorylation of glucose to glucose-6-phosphate is important for preventing glucose efflux from the cell, we asked whether STF-31 might function by inhibiting the phosphorylation of glucose by hexokinase. Hexokinase activity was inhibited by STF-31 only after three days of treatment in VHL-deficient RCC4 cells but hexokinase activity of RCC4/VHL cells with wild-type VHL was unchanged by STF-31 (FIG. 2D). The baseline activity of hexokinase is higher in RCC4 cells, consistent with VHL-deficient RCCs having higher rates of glycolysis and that the hexokinase gene is a HIF target (FIGS. 2A, 2D and 6B) (Iyer et al., *Genes Dev*, 12:149-162 (1998)). The decrease in hexokinase activity occurred subsequent to changes in glucose uptake, indicating that inhibition of hexokinase is not directly responsible for the differential cytotoxicity of STF-31356 in cells with and without VHL. Furthermore, inhibitors of glycolysis, non-specific glucose transport inhibitors, or hexokinase did not result in selective cytotoxicity to VHL-deficient cells (FIG. 7). These data indicate that STF-31 decreases glycolysis by decreasing glucose transport.

To further investigate the relationship between HIF and STF-31 toxicity, we silenced HIF-1β in RCC4 cells and assessed its affect on glucose uptake (FIG. 6D). Transiently inhibiting HIF-1β, the constitutively expressed binding partner of HIF-1α and HIF-2α reduces HIF activity in RCC4 cells to the levels found in wild-type VHL cells. Glucose uptake was insensitive to treatment with STF-31 when the HIF-1β was silenced in RCC4 cells, further supporting the concept that the HIF-dependent glucose uptake was responsible for the differential toxicity of STF-31 to VHL-deficient renal carcinomas (FIG. 2E).

Inhibiting Glucose Uptake Inhibits Both Glycolysis and Production of ATP

We next investigated how a decrease in glycolysis could lead to selective necrotic cell death. One possibility is that the reduction in glycolysis lowers the availability of pyruvate, the essential precursor for the generation of acetyl-CoA. Previous studies have indicated that RCCs have decreased oxygen consumption because of constitutive HIF expression and the subsequent induction of genes, such as PDK1 and MXI1, that inhibit the conversion of pyruvate to acetyl-CoA (Fukuda et al., (2007). *Cell*, 129:111-122 (2007); Kim et al., *Cell Metab*, 3:177-185 (2006); Papandreou et al., *Cell Metab*, 3:187-197 (2006).; Zhang et al., *Cancer Cell* 11:407-420 (2007)), we examined whether STF-31 inhibited oxidative phosphorylation and the use of pyruvate. We therefore examined oxygen consumption as a marker of oxidative phosphorylation and ATP production in treated and untreated cells. While there was a difference in oxygen consumption between VHL-deficient and wild-type VHL cells, there was no difference in oxygen consumption between cells treated with STF-31 and those that were not treated (FIG. 2F). This finding demonstrates that the mitochondria and the oxidative pathway remain unaffected by STF-31. However, the decrease in glucose uptake in response to treatment with STF-31 in VHL-deficient cells results in a 75% decrease in ATP levels (FIG. 2G). Furthermore, inhibition of ATP production in response to STF-31 treatment is dose-dependent (FIG. 2H). These data indicate that loss of VHL is associated with reduced oxidative phosphorylation and greater dependence on glycolysis for ATP production. By disrupting glycolysis, STF-31 functions in a synthetic lethal manner to VHL mutation, ultimately killing VHL-deficient cells by inhibiting their primary mechanism of energy production.

Figure 11:
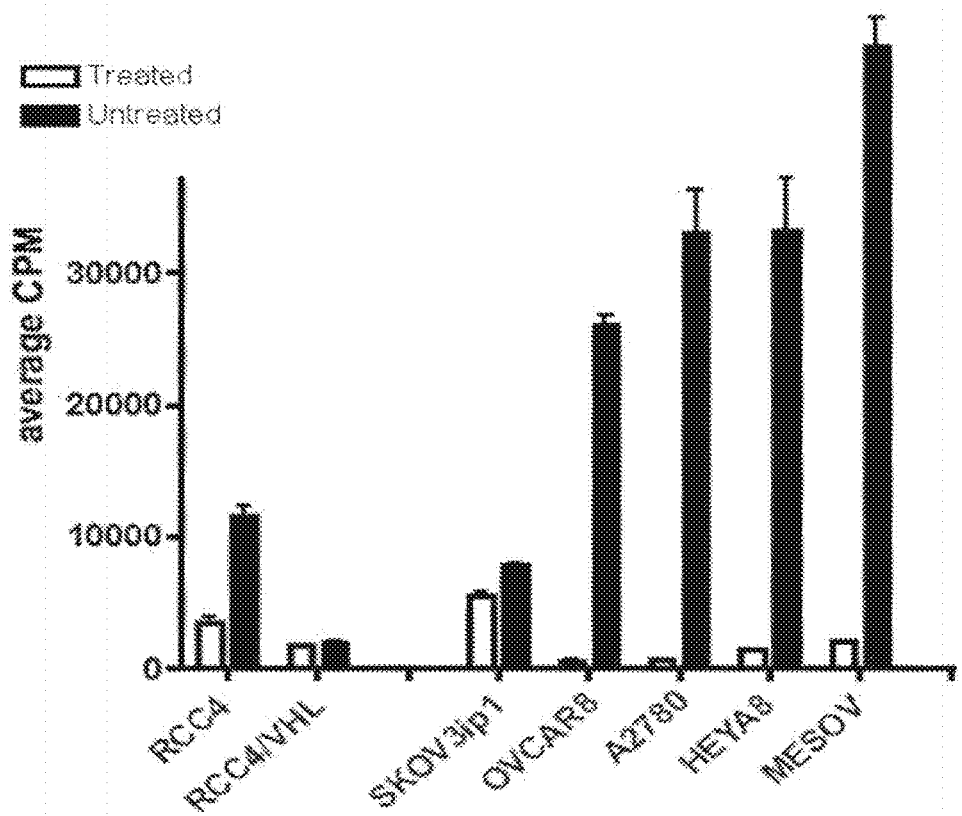
FIG. 11. Glucose Uptake inhibition correlates with cytotoxicity in variety of tumor types. Treatment was 5 uM for 48 hr. Inhibition of glucose uptake correlates with sensitivity to GLUT1 inhibitor, and increased average CPM may correlate with increased sensitivity. Trypan blue exclusion correlated well with these results.
Figure 12:
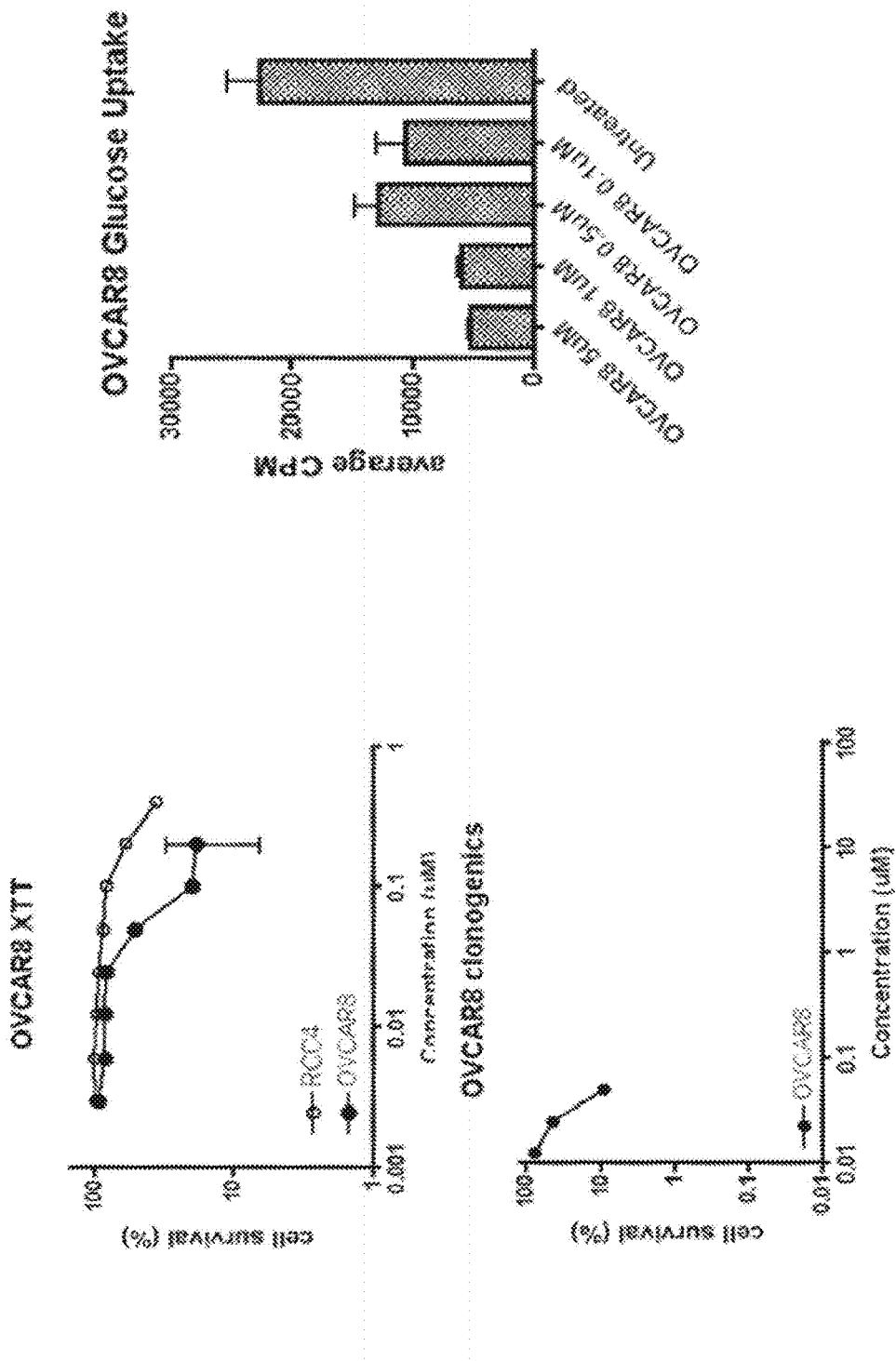
FIG. 12. Glucose uptake inhibition correlation with cytotoxicity is dose dependent.
Figure 13:
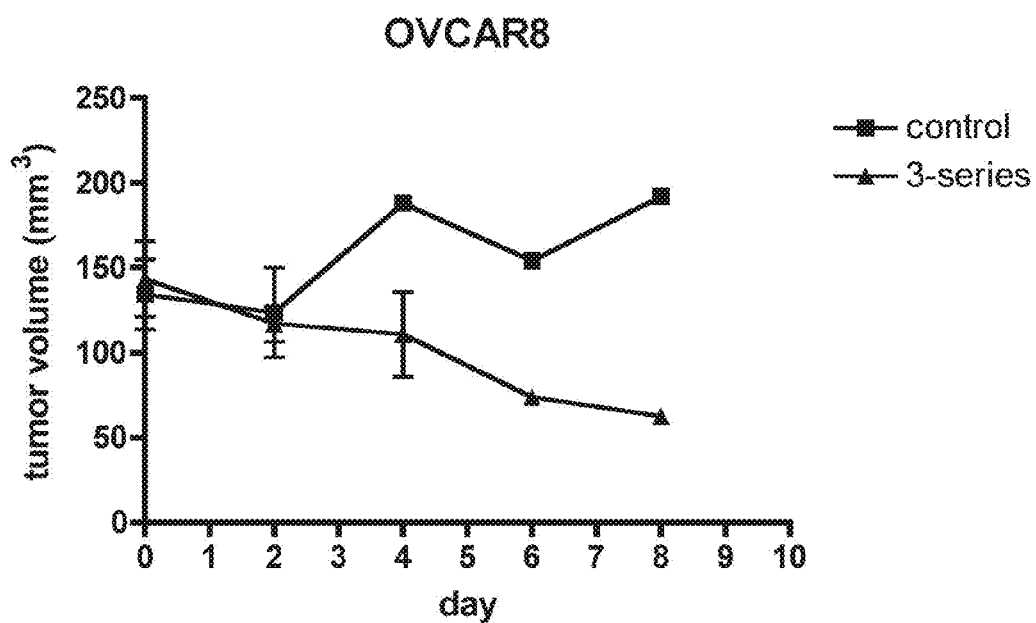
FIG. 13. GLUT1 inhibitors show significant anti-tumor activity in multiple human tumor xenograft models.
Figure 14:
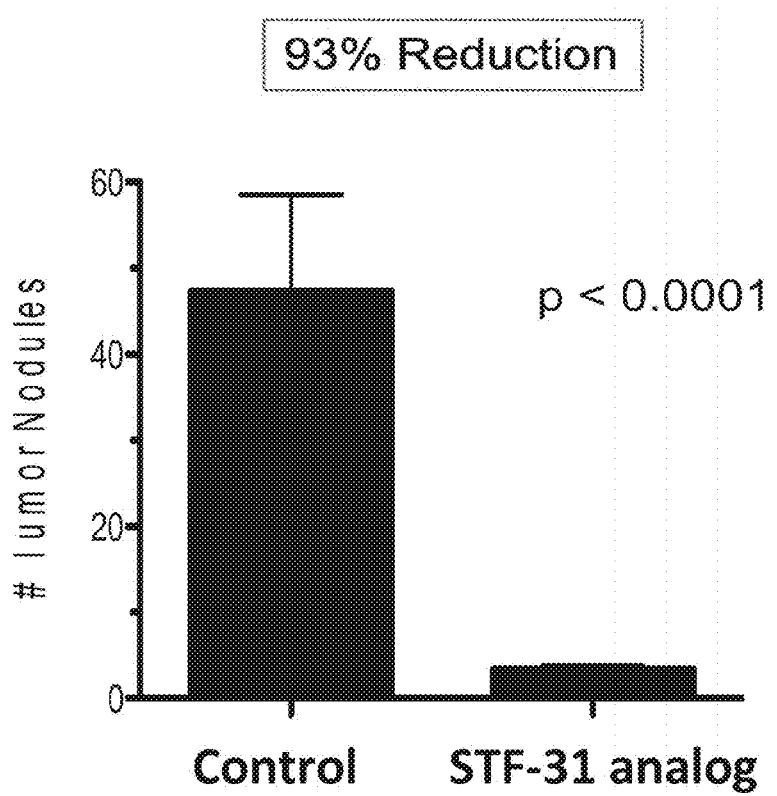
FIG. 14. GLUT1 inhibitors Are Efficacious in the Human Ovarian Metastasis Model as measured by number of metastatic nodules and tumor weight (tumor burden).

Glucose uptake inhibition correlates with cytotoxicity in variety of tumor types. Treatment was 5 uM for 48 hr. Inhibition of glucose uptake correlates with sensitivity to GLUT1 inhibitor, and increased average CPM may correlate with increased sensitivity. Trypan blue exclusion correlated well with these results (FIG. 11). Glucose uptake inhibition also correlates with cytotoxicity in a dose dependent manner (FIG. 12). GLUT1 inhibitors show significant anti-tumor activity in multiple human tumor xenograft models, including OVCAR8 (FIG. 13). GLUT1 inhibitors are efficacious in the human ovarian metastasis model as measured by number of metastatic nodules and tumor weight (tumor burden) (FIG. 14). GLUT1 inhibitors lead to a 93 percent reduction in tumor burden (FIG. 14).

VHL-Deficient Cells are Dependent on Glycolysis

These data support an emerging model that renal cells with defective VHL, like a range of other cancers, are highly dependent on aerobic glycolysis for energy production (Gatenby, R. A., and Gillies, R. J., *Nat Rev Cancer,* 4:891-899 (2004); Warburg, O., *Science,* 124:269-270 (1956); Warburg, O., *Science,* 123, 309-314 (1956); Yang et al., *Cancer Genet Cytogenet,* 196:45-55 (2010)). We further examined this conditional genetic interaction of glucose dependency and VHL interaction by depriving the cells of glucose in a growth curve assay. RCC4 cells and 786-O cells lacking functional VHL were sensitive to changes in glucose levels, while the isogenically matched cells with wild-type VHL continued to grow despite the absence of glucose (FIGS. 6E and 6F). Conversely, when cells were deprived of pyruvate, cells with and without VHL were relatively unaffected. These results suggest that VHL-deficient cells are more sensitive than cells with VHL to changes in glucose. The addition of pyruvate was unable to overcome deprivation of glucose and the inhibition of glycolysis because of the increased expression of PDK and MXI1 that inhibit the conversion of pyruvate to acetyl-CoA. Together, these data demonstrate that VHL-deficient cells are unable to utilize oxidative phosphorylation to overcome their dependence on glycolysis for energy production.

GLUT1 is Overexpressed in Renal Carcinomas

Figure 3:
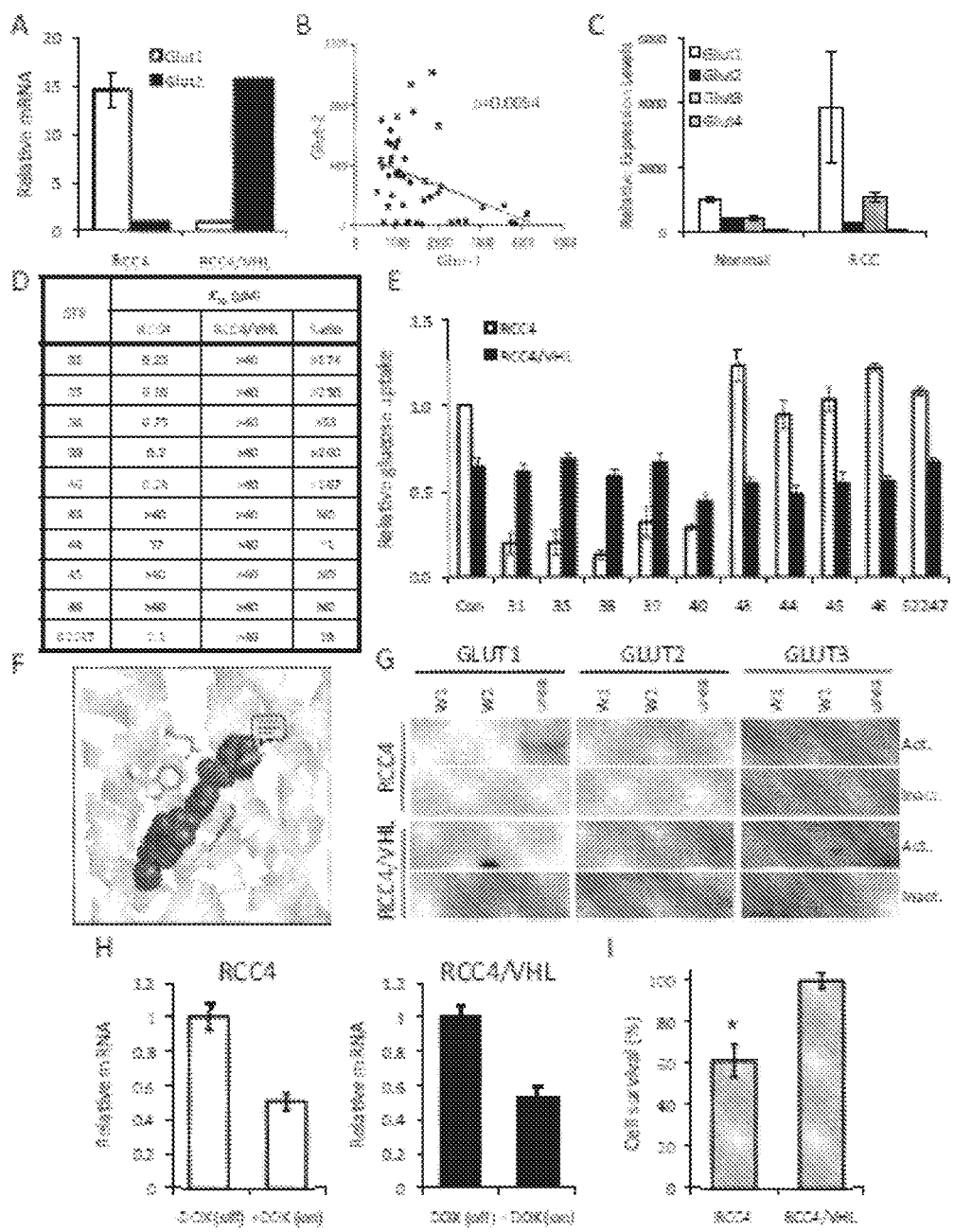
FIG. 3. Inhibition of GLUT1 leads to cell death in VHL-deficient cells. (A) Relative mRNA expression of GLUT1 and GLUT2 in RCC4 and RCC4/VHL as determined by quantitative real-time PCR and normalized to TBP. All error bars represent the standard error of the mean. (B) Expression of GLUT1 is inversely correlated with GLUT2. Relative expression from a renal cancer dataset. (C) Expression of GLUT1, GLUT2, GLUT3, and GLUT4 in a renal cancer dataset containing normal tissue and renal clear cell carcinomas. (D) Table of STF-31 analogs. $IC_{50}$ was evaluated by XTT assay in RCC4 and RCC4/VHL cells. Ratio=IC50(RCC4/VHL)/$IC_{50}$(RCC4). (E) Glucose uptake was measured for active (STF-35, -38, -39, -40) and inactive (STF-43, -44, -45, -46) STF-31 analogs. Only active analogs affected glucose uptake in VHL-defective cells. (F) Docking of STF-31 active analogs (red) into the solute channel of GLUT1. Fasentin is shown in yellow. (G) STF-31 analog, STF-42, binds to GLUT1. STF-41, an inactive analog of STF-31 does not bind GLUT1. Cell lysates of RCC4 and RCC4/VHL were incubated with Affigel immobilized STF-41 (inactive) or STF-42 (active), following washes, were eluted with urea buffer. Elutions were probed for GLUT1, GLUT2, or GLUT3. (H) Relative mRNA levels of GLUT1 from RCC4 and RCC4/VHL cells with a stable, inducible shRNAmir to GLUT1. Cells were treated with 500 ng/ml of DOX for 5 days. (I) Cell viability by XTT assay of RCC4 and RCC4/VHL expressing an inducible shRNAmir to GLUT1. Cells were treated with 250 ng/ml of DOX for 4 days ($*p<0.005$). All error bars represent the standard error of the mean.
Figure 8:
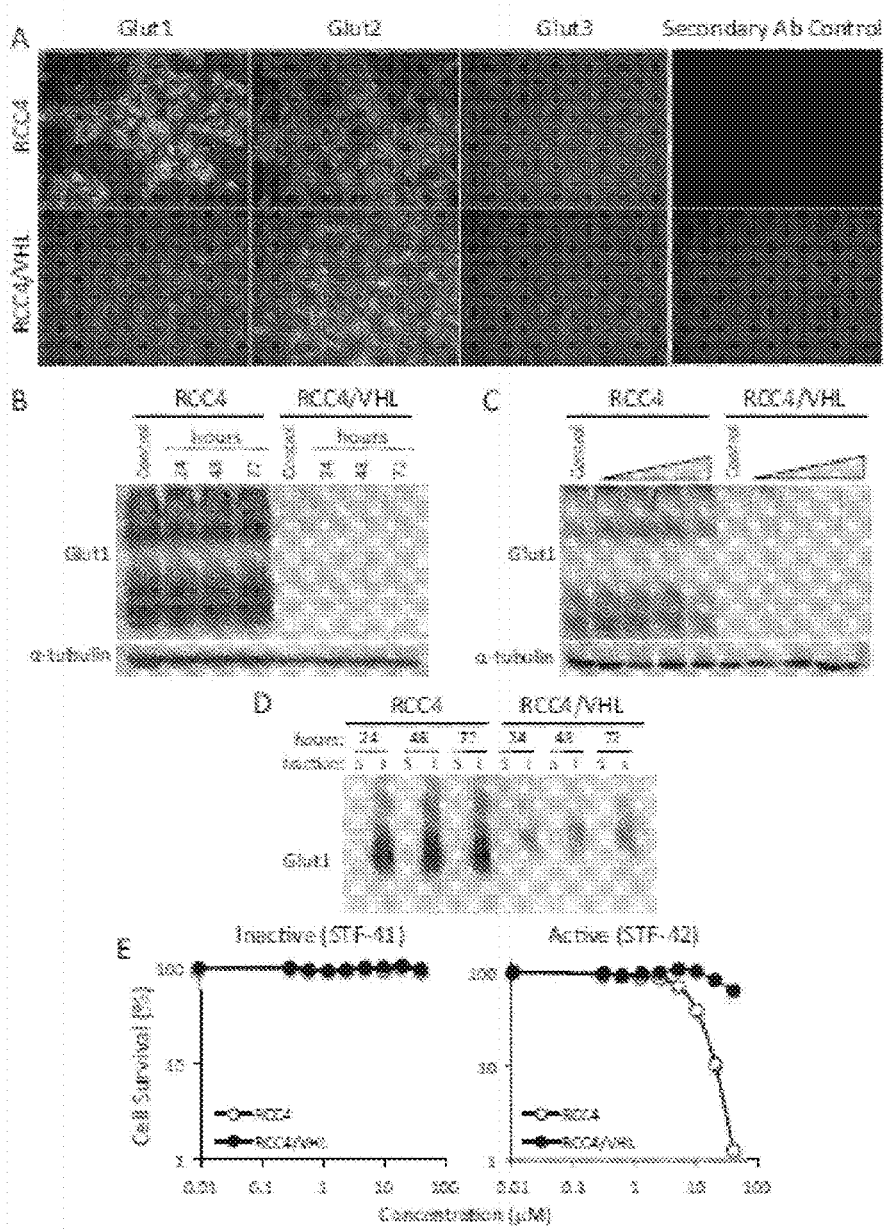
FIG. 8. GLUT1 levels are unaffected by STF-31. (A) Immunofluorescence staining of GLUT1, GLUT2, or GLUT3 in RCC4 or RCC4/VHL cells, demonstrating high levels of GLUT1 in RCC4, high levels of GLUT2 in RCC4/VHL cells, and low expression of GLUT3 in both RCC4 and RCC4/VHL cells. (B) GLUT1 protein levels are unaffected by STF-31 (5 µM) for the indicated time. (C) GLUT1 protein levels are unaffected by increasing concentrations (1.25, 2.5, 5 or 10 µM) of STF-31. Cells were treated for 3 days. (D) RCC4 and RCC4/VHL cells were fractionated into soluble and insoluble fractions, following treatment with STF-31 for the indicated times. Fractions were then probed for GLUT1 protein. (E) Cell viability assay (XTT metabolism) of RCC4 or RCC4/VHL in response to four day treatment with the inactive STF-41 or the active STF-42 analogs.

We next examined the differential glucose uptake between RCCs with and without VHL treated with STF-31 that subsequently lead to the selective death of VHL-deficient cells. We first examined the message levels of the two main glucose transporters, GLUT1 and GLUT2 by quantitative real-time PCR and immunofluorescence (FIGS. 3A, and 8A). GLUT1 is an inducible, high-affinity glucose transporter, while GLUT2 is the glucose transporter responsible for basal glucose uptake (Pajor et al., *J Pharmacol Exp Ther,* 324:985-991 (2008)). Other family members, such as GLUT3 and GLUT4, are not expressed in renal cells. GLUT1 was highly expressed in cells lacking VHL, while cells with VHL had very low levels of GLUT1 (FIGS. 3A and 8A). In contrast, GLUT2 was highly expressed in cells with wild-type VHL. Cells deficient in VHL had very low levels of GLUT2 that could barely be detected (FIG. 3A). The relative expression levels of GLUT1 and GLUT2 were compared in clear cell renal cell carcinoma tumors, which demonstrated a significant inverse correlation between the two genes (Jones et al., *Clin Cancer Res,* 11:5730-5739 (2005)). GLUT1 levels were high in the renal carcinoma, while GLUT2 levels were high in normal renal cells (FIG. 3B). Although GLUT3 levels were induced in renal carcinoma compared to normal renal cells, the absolute level of GLUT3 was still relatively low compared to GLUT1 levels (FIG. 3C). Furthermore, GLUT4 levels were barely detectable (FIG. 3C). The expression of GLUT1 and GLUT2 glucose transporters indicates that STF-31 kills cells with mutant VHL by inhibiting the higher affinity GLUT1 glucose transporter, depriving VHL-deficient cells of glucose and consequently, energy needed to sustain the cells.

TABLE 2

VHL status, HIF-1, HIF-2, GLUT1, and GLUT2 expression, and sensitivity to STF-31 in a panel of RCC cell lines.

| | VHL | HIF-1 | HIF-2 | GLUT1 | GLUT2 | GLUT3 | GLUT4 | 3-series sensitivity |
|---|---|---|---|---|---|---|---|---|
| ACHN | Wild-type | Yes | Yes | ++ | +++ | + | + | No |
| ACHN shVHL | Silenced | Yes | Yes | ++ | Not detected | +++ | +++ | Yes |
| Caki-1 | Wild-type | Yes | Yes | ++ | Not detected | +++ | + | Yes |
| RCC4 | Mutant | Yes | Yes | +++ | + | +++ | Not detected | Yes |
| RCC4/VHL | Wild-type | Yes | Yes | + | +++ | + | Not detected | No |
| SN12C | Wild-type | Yes | Yes | ++ | + | +++ | +++ | Yes |
| SN12C shVHL | Silenced | Yes | Yes | + | Not detected | + | +++ | Yes |
| UMRC6 | Mutant | No | Yes | ++ | + | + | Not detected | No |
| UMRC6/VHL | Wild-type | No | Yes | + | + | + | Not detected | No |
| 786-0 | Mutant | No | Yes | +++ | Not detected | ++ | +++ | Yes |
| 786/VHL | Wild-type | No | Yes | +++ | Not detected | + | +++ | Yes |

To further correlate cytotoxic activity of STF-31 with inhibition of glucose uptake, analogs of STF-31 were synthesized and tested in a 4-day viability assay using paired RCC lines with and without VHL (FIG. 3D). All analogs of STF-31 that selectively killed VHL-deficient RCCs inhibited glucose uptake, whereas all inactive analogs that did not kill VHL-deficient cells did not inhibit glucose uptake (FIG. 3E). To determine whether this assay reflected a specific inhibition of glucose uptake rather than broad toxicity, we also investigated cytotoxins that are known to act by a different mechanism. The PAT class of compounds (e.g. STF-62247), which induced VHL-dependent, HIF-independent autophagic cell death, did not decrease glucose uptake in this assay, indicating that STF-31 cytotoxicity is dependent on glucose metabolism (FIGS. 3D and 3E)(Turcotte et al., Cancer Cell, 14:90-102 (2008); Weihua et al., Cancer Cell, 13:385-393 (2008)). These data suggest that STF-31 is specifically cytotoxic to cells that have elevated HIF levels due to their increased rate and dependence on glucose uptake and glycolysis.

STF-31 Specifically Binds GLUT1

We next investigated whether STF-31 specifically inhibits GLUT1. Treatment with STF-31 did not affect GLUT1 protein levels in a time- or concentration-dependent manner (FIGS. 8B and 8C). Moreover, the levels of soluble GLUT1 protein were also unaffected by STF-31 (FIG. 8D). To examine interactions between STF-31 and GLUT1, a range of active and inactive STF-31 analogs as well as fasentin were structurally modeled with GLUT1 (FIG. 3F). Inactive analogs, which did not kill VHL-deficient cells or inhibit glucose uptake, did not dock with GLUT1. Active analogs, which selectively kill VHL-deficient cells through glucose uptake, docked within the central channel of GLUT1 (FIG. 3F). Interestingly, fasentin, a fas-dependent glucose transport inhibitor (Wood et al., Mol Cancer Ther, 7:3546-3555 (2008)), which was not toxic to either VHL-deficient or cells with wild-type VHL, docked towards the extracellular end of channel and not deep in the central pocket like the active analogs (FIGS. 7A, 7B, and 3F). Thus, in a structural model of GLUT1, STF-31 and other active analogs are predicted to interact within the central pocket of the solute carrier.

To further confirm specificity of STF-31 for GLUT1, binding assays were preformed to determine the interaction of STF-31 with GLUT1 and to determine whether STF-31 bound additional glucose transporters, such as GLUT2 or GLUT3. Two different analogs of STF-31, STF-41 (inactive) and STF-42 (active) were synthesized and linked to an immobilized linker (Affi-gel-10)(FIG. 8E). Total cell extracts from both RCC4 and RCC4/VHL were incubated with either immobilized STF-41 or STF-42. Following washing of these resins, the affinity columns were then eluted with urea and subjected to immunoblotting for GLUT1. GLUT1 from RCC4 cells bound to the active STF-42 but not to the inactive STF-41 (FIG. 3G). Lysates from RCC4/VHL cells did not bind to either STF-42 or STF-41, likely due to low expression of GLUT1 in these cells. More importantly, the active STF-42 did not bind GLUT2 or GLUT3 from RCC4 or RCC4/VHL extracts, demonstrating that STF-42, an active STF-31 analog, can bind specifically to the high affinity glucose transporter, GLUT1 and does not bind to additional glucose transporters.

Inhibition of GLUT1 Leads to Cell Death

Simply inhibiting glycolysis with 2-deoxy-D-glucose, a non-degradable analog of glucose, is not sufficient to confer differential toxicity between RCC cells with and without VHL. 2-DG treatment was not cytotoxic to either RCC4 and RCC4/VHL in either short-term or long-term survival assays (FIGS. 6G and 6H). Inhibition of glucose transporters with fasentin, (Wood et al. (2008). Mol Cancer Ther 7, 3546-3555) a FAS-dependent inhibitor, was relatively non-toxic (FIGS. 7A and 7B). Another non-specific glucose transporter inhibitor, phloretin (Pajor et al., J Pharmacol Exp Ther, 324:985-991 (2008)), and the hexokinase inhibitors, bromopyruvate (Ko et al., Cancer Lett, 173:83-91 (2001)), clotrimazole (Penso et al., Eur J Pharmacol, 342:113-117 (1998)), and lonidamine (Floridi et al., J Natl Cancer Inst, 66:497-499 (1981)) were all toxic to both RCC4 and RCC4/VHL cells (FIGS. 7C-7F). We also examined whether the small molecule STF-31 functioned as a kinase inhibitor. In vitro testing of a broad range of 50 different kinases demonstrated no significant decrease in any of the kinases examined (Table 2). We also examined whether specific inhibition of GLUT1 would mimic STF-31 cytotoxicity. Using an inducible shRNAmir, we achieved approximately 50% reduction in GLUT1 levels in both RCC4 and RCC4/VHL cells (FIG. 3H). This 50% reduction in GLUT1 levels directly translated to a loss of viability of VHL-deficient cells (FIG. 3I). Despite a 50% reduction of GLUT1 levels in cells with wild-type VHL, there was not a concomitant reduction in viability of these cells (FIG. 3I). Thus, specific inhibition of GLUT1, either pharmacologically with STF-31 or genetically with RNA interference, leads to death in cell lacking VHL.

TABLE 3

STF-31 does not inhibit a broad range of kinases. Kinase response to STF-31 (10 µM). STF-31536 does not inhibit a broad range of kinases.

| | | | |
|---|---|---|---|
| Abl | 108 | IRAK1 | 105 |
| AMPK | 92 | JAK2 | 113 |
| ASK1 | 129 | JNK1α1 | 101 |
| Aurora-A | 108 | MAPKAP-K2 | 87 |
| Axl | 87 | MEK1 | 99 |
| CaMKI | 87 | Met | 105 |
| CDK1/cyclinB | 96 | MKK4 | 128 |
| CDK6/cyclinD3 | 105 | MLK1 | 97 |
| CHK1 | 114 | MSK1 | 107 |
| CK1γ1 | 85 | mTOR | 101 |
| cKit(D816H) | 99 | NEK2 | 103 |
| CSK | 99 | PAK2 | 97 |
| c-RAF | 103 | PDK1 | 105 |
| cSRC | 104 | PI3K | 97 |
| DAPK1 | 92 | Pim-2 | 112 |
| DYRK2 | 94 | PKA | 96 |
| EphA1 | 102 | PKBα | 99 |
| FGFR1 | 107 | PKCδ | 116 |
| Flt3 | 111 | Plk3 | 104 |
| Fyn | 91 | ROCK-I | 74 |
| GSK3α | 134 | Rsk1 | 120 |
| Hck | 84 | SAPK2a | 127 |
| IGF-1R | 108 | Syk | 94 |
| IKKα | 102 | Tie2 | 111 |
| IR | 121 | TrkA | 124 |

In Vivo Monitoring and Efficacy of STF-31

Figure 4:
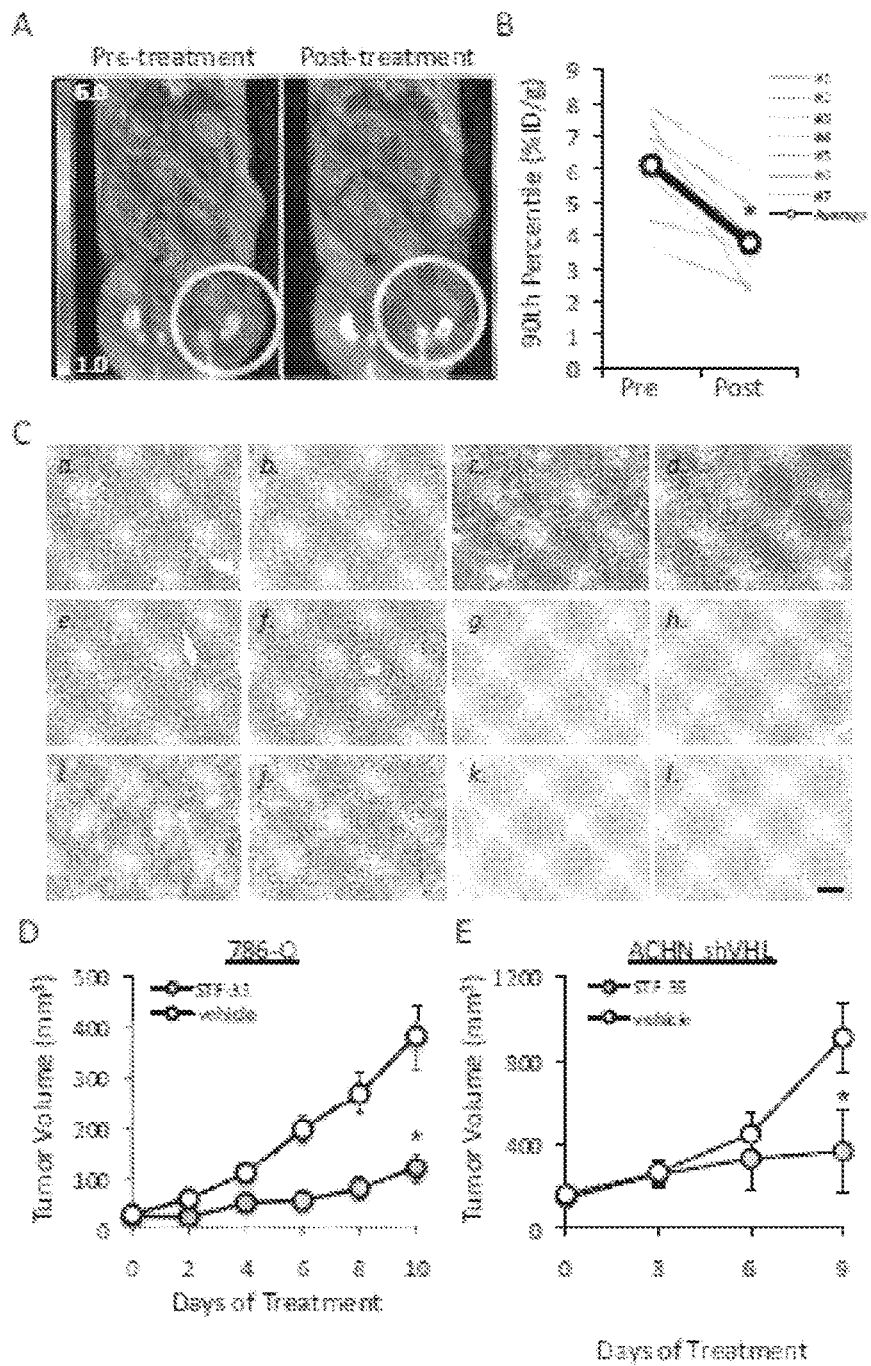
FIG. 4. In vivo monitoring and efficacy of STF-35. (A) FDG-PET imaging demonstrates an in vivo decrease in glucose uptake in a renal clear cell carcinoma xenograft in response to STF-35, a more soluble, active analog of STF-31. 786-O, a renal clear cell carcinoma with a naturally occurring VHL mutation, were implanted subcutaneously into the flanks of CD-1 nude mice. Representative axial cross section of a mouse prior to treatment (left) and following three daily i.p. injections with STF-35 (11.6 mg/kg)(right), overlaid with CT scan. (B) Quantitatively, STF-35 inhibits FDG-PET in mouse xenografts. Quantification of FDG-PET inhibition by STF-35 as determined by the $90^{th}$ percentile ROI for percent injected dose per gram (% ID/g)($*p<0.01$). (C) STF-35 is not toxic to normal tissues. (a, b) Kidney of vehicle- and STF-35-treated animals. (c, d) Spleen of vehicle- and STF-35-treated animals. (e, f) Liver of vehicle- and STF-35-treated animals. (g, h) Heart of vehicle- and STF-35-treated animals. (i, j) Salivary gland of vehicle- and STF-35-treated animals. (k, l) Brain of vehicle- and STF-35-treated animals. Animals were treated for 10 days with vehicle or STF-35 (11.6 mg/kg for the first 3 days, followed by 7.8 mg/kg for the next week). Scale bar represents 100 microns. (D) STF-35 delays tumor growth. 786-0 tumor-bearing mice were treated daily with vehicle or STF-35 (11.6 mg/kg for the first 3 days, followed by 7.8 mg/kg for the next week)($*p<0.005$). (E) STF-35 delays tumor growth in cells that have lost VHL. ACHN cells expressing a short hairpin RNA to VHL were implanted subcutaneously into the flanks of immunocompromised mice. Once tumors reached an average of >150 $mm^3$, mice were treated daily with STF-35 or vehicle ($*p<0.05$). All error bars represent the standard error of the mean.

The high utilization of glucose by cancer cells compared to normal cells is the basis of fluoro-deoxyglucose positron emission tomography (FDG-PET) in the diagnosis of cancer. To determine whether STF-31 was functioning by inhibiting glucose uptake, we monitored the effects of STF-31 by FDG-PET (Larson et al., Curr Opin Urol, 18:65-70 (2008); Mankoff et al., Clin Cancer Res, 13:3460-3469 (2007); Thomas et al., Nat Med, 12:122-127 (2006)). Pre-treatment scans of animals inoculated with subcutaneous VHL-deficient human renal cell carcinomas revealed a high glucose uptake within the tumors (FIG. 4A). Following three daily doses of STF-35, a more soluble analog of STF-31, subsequent scanning revealed a striking decrease in glucose uptake within the tumors (FIGS. 4A and 4B). Despite a variation in initial tumor FDG uptake, treatment with STF-35 consistently decreased FDG uptake (FIG. 4B). Control animals that were given either vehicle or STF-62247 did not have a decrease in glucose uptake (data not shown). These results demonstrate that the effectiveness of STF-31 and its analog STF-35 can be directly monitored clinically by FDG-PET.

Figure 9:
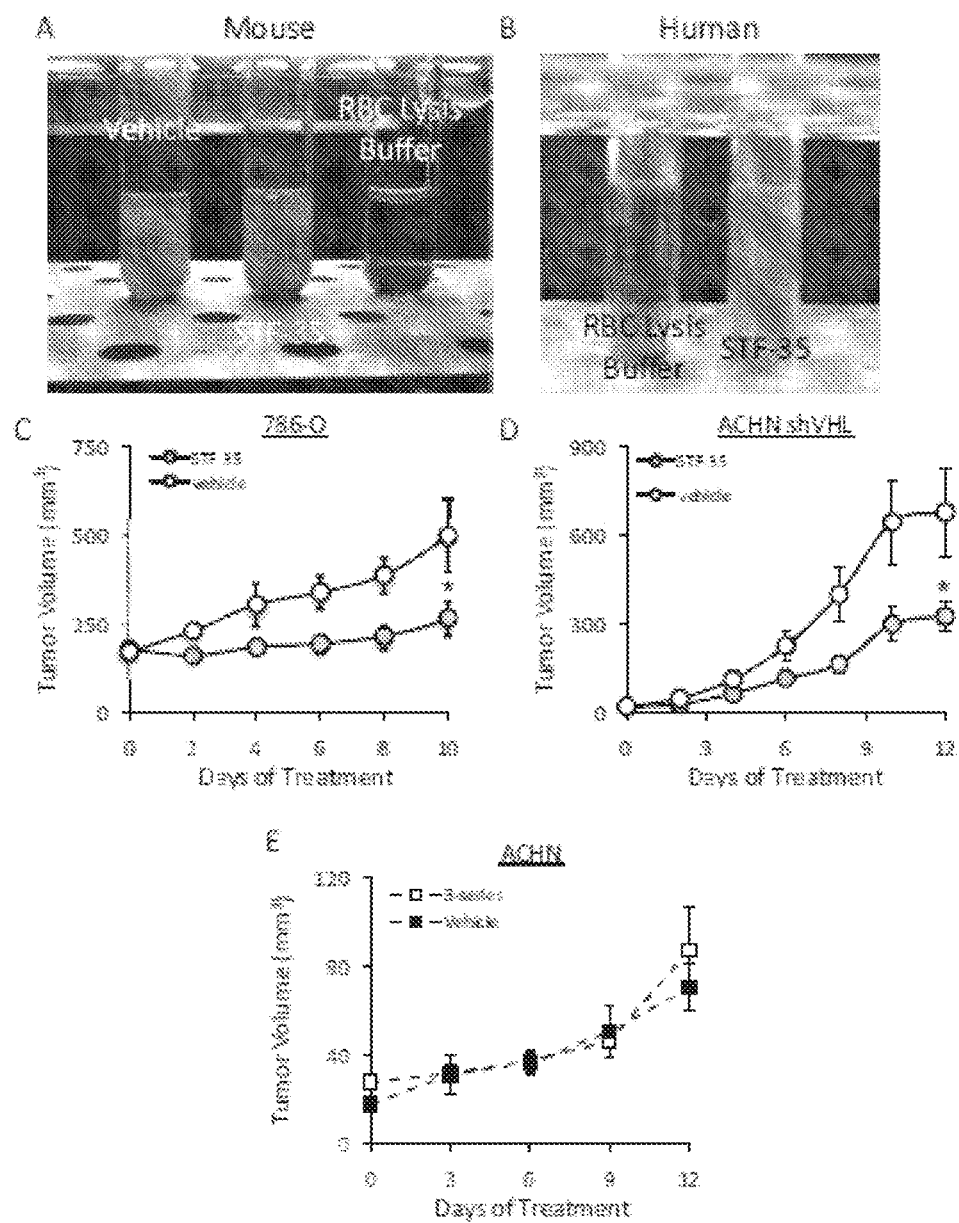
FIG. 9. Red blood cells do not undergo hemolysis in response to STF-31536. (A) Representative photos of mouse red blood cells were treated with vehicle, STF-35 (2.5 µM or 5 µM), or red blood cell lysis buffer. No hemolysis was observed after 7 days. (B) Representative photos of human red blood cells treated with either red blood cell lysis buffer or STF-35 (5 µM). No hemolysis was observed after 7 days. (C) 786-O tumors are sensitive to STF-35 treatment. 786-O cells were implanted subcutaneously into the flanks of immunocompromised mice. Once tumors reached 150 mm$^3$, mice were treated twice daily with STF-35 (7.8 mg/kg) or vehicle (*p<0.05). (D) ACHN shVHL tumors are sensitive to STF-35 treatment. ACHN shVHL cells were implanted subcutaneously into the flanks of immunocompromised mice. Once tumors reached an average of ~20 mm$^3$, mice were treated daily with STF-35 (7.8 mg/kg) or vehicle (*p<0.05). (E) ACHN tumors with wild-type VHL are insensitive to STF-35 treatment. ACHN cells were implanted subcutaneously into the flanks of immunocompromised mice. Once tumors reached an average of >20 mm3, mice were treated daily with STF-35 (7.8 mg/kg) or vehicle. All error bars represent the standard error of the mean.

Animals treated with STF-35 for 14 days exhibited no normal tissue toxicity (FIG. 4C), immunosuppression (Table 3), or apparent seizures. Treated mice had normal levels of red blood cells, hemoglobin, and hematocrit (Table 3). Isolated adult mouse erythrocytes, which primarily express GLUT4 (Montel-Hagen et al., Cell 132:1039-1048 (2008)), did not undergo hemolysis in response to STF-35 (FIG. 9A). Moreover, treatment of human red blood cells with STF-35 did not cause hemolysis (FIG. 9B), suggesting that STF-35 might have a high therapeutic index.

TABLE 4

Complete blood count panel from control mice and mice treated with STF-35. CBC panel from control mice and mice treated with STF-35 for 10 days.

|  | Vehicle | 3-series |
| --- | --- | --- |
| WBC | 3.8 ± 1.8 | 5.5 ± 0.6 |
| RBC | 8.2 ± 1.1 | 8.1 ± 0.7 |
| Hemoglobin | 12.3 ± 1.5 | 12.1 ± 1.1 |
| Hematocrit | 39.6 ± 4.7 | 38.4 ± 3.7 |
| MCV | 49.6 ± 1.0 | 47.6 ± 2.1 |
| MCH | 15.4 ± 0.1 | 15.1 ± 0.7 |
| MCHC | 31.0 ± 0.7 | 31.6 ± 0.2 |
| Neutrophils | 36.8 ± 14.3 | 66.2 ± 14.3 |
| Lymphocytes | 57.8 ± 16.8 | 26.2 ± 14.5 |
| Monocytes | 5.2 ± 3.4 | 6.0 ± 3.1 |
| Absolute Neutrophils | 1372.0 ± 902.5 | 3599.8 ± 702.8 |
| Absolute Lymphocytes | 2241.8 ± 1169.1 | 1475.6 ± 871.9 |
| Absolute Monocytes | 174.2 ± 105.6 | 322.0 ± 147.2 |

We next examined whether the PPBs are effective at treating tumors in a xenograft model of RCC. Daily systemic treatment of mice with VHL-deficient xenografts with STF-35 for ten to fourteen days markedly delayed tumor growth in two renal cell carcinoma model systems: 786-O with a naturally occurring VHL mutation and ACHN expressing short hairpin RNA to VHL (FIGS. 4D, 4E, 9C, and 9D). In both of these models, treatment with STF-35 delayed tumor growth compared to tumors treated with vehicle alone. Importantly, ACHN tumors with wild-type VHL grew at similar rates as those treated with STF-35 or treated with vehicle control (FIG. 9E), indicating that STF-35 is differentially cytotoxic to tumors that have lost VHL function, a common and frequent event in renal cell carcinoma. Taken together, we have identified an agent that is selectively toxic to a particular genotype found in the vast majority of kidney cancers. Furthermore, through its mechanism of action of inhibiting glucose metabolism, we are able to follow its effectiveness with FDG-PET, a clinically utilized imaging modality.

Discussion

Figure 10:
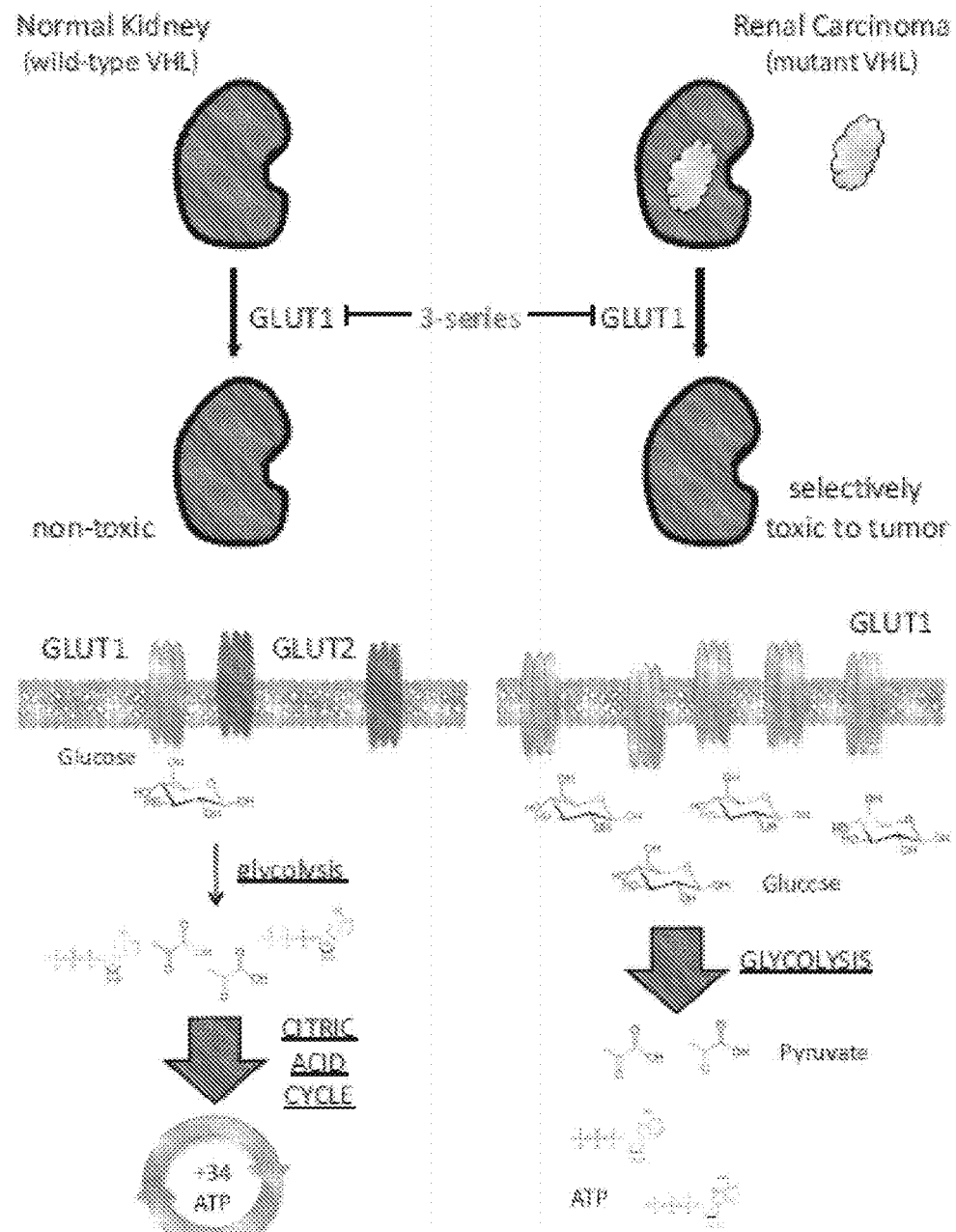
FIG. 10. Model of ST-31 mechanism of synthetic lethality. In greater than 90% of renal carcinoma, VHL is mutated. Inhibition of GLUT1 in renal carcinoma results in toxicity. Mutation of VHL leads to increased GLUT1 expression, increased glucose uptake, and a high dependence on glycolysis for energy production. In normal kidney tissue, VHL is wild-type and depends on GLUT2 for glucose uptake and the citric acid cycle for generation of ATP.

STF-31 represents the second class of small molecules that we have identified that selectively kill RCCs lacking functional VHL (Turcotte et al., Cancer Cell, 14:90-102 (2008)). However, STF-31 is distinct from the previous class in its mechanism of killing RCC. Whereas PATs selectively induce autophagy, STF-31 and other PPBs act by disrupting glucose uptake and utilization. The selective cytotoxicity of this effect provides direct evidence to support an emerging model of dependence on glycolysis in many cancer cell types, including the majority of RCCs (Kroemer, G., and Pouyssegur, J., Cancer Cell, 13, 472-482 (2008)). The disruption of VHL or other regulators of HIF leads to active inhibition of mitochondrial activity through the HIF-mediated induction of PDK1, a kinase that blocks the activity of pyruvate dehydrogenase and the production of acetyl-CoA. Thus, VHL-deficient RCCs are selectively sensitive to STF-31 because aberrant HIF stabilization results in diminished mitochondrial activity, causing these cells to become highly dependent on glucose uptake for glycolysis and ATP production. By inhibiting glucose uptake and retention, STF-31 specifically targets the Achilles' heel of RCCs. Cells with an intact VHL pathway are not strictly dependent on glycolysis for viability and are therefore insensitive to STF-31 toxicity (FIG. 10). Our findings indicate that the differential metabolism of cancer cells can be exploited for the preferential targeting of these cells by small molecules.

Our results have a number of implications for the development of new cancer therapeutics. Firstly, our method of screening for compounds that are synthetically lethal to the loss of VHL should be adaptable to other tumor types with distinct genotypes, such as the loss-of-function of a particular tumor suppressor gene or gain-of-function of a specific oncogene (Weihua et al., (2008). Cancer Cell 13, 385-393). Secondly, the selective cytotoxicity of STF-31 are not be restricted only to VHL-deficient tumors alone. It is likely that a number of other cancer types possess genetic or epigenetic alterations that make them highly dependent on aerobic glycolysis for energy production and therefore sensitive to PPBs. This is currently an active area of research. Similarly, cells with wild-type VHL could be sensitized to STF-31 by inactivating VHL. It should also be noted that targeting GLUT1 in human renal cell cancers is feasible as GLUT1 heterozygous knockout mice are viable and recapitulate the human GLUT1 deficiency syndrome, which is effectively treated by a ketogenic diet (Klepper, J., and Leiendecker, B., *Dev Med Child Neurol,* 49:707-716 (2007); Wang et al., *Hum Mol Genet,* 15:1169-1179 (2006)). It is important to reiterate here that we did not observe any normal tissue toxicity, including brain, in these studies. Finally, our data show that the effectiveness of STF-31 can be monitored by in vivo imaging. This property offers the potential advantages for dosage optimization and identification of which kidney cancers will respond best to STF-31 treatment in Phase I clinical trials. Diagnosing and predicting response of RCC by FDG-PET imaging will be greatly aided by simultaneous CT. Furthermore, FDG-PET imaging of RCC will likely benefit patients with high grade tumors or tumors that have metastasized beyond the kidney. Being able to track the response of a particular tumor is both cost-effective and lends itself to personalized medicine, which are two of the primary objectives of future cancer therapy.

Experimental Procedures

Cell Culture and Reagents. All cells were grown in DMEM+10% FCS. ACHN and ACHN shVHL were a kind gift from George V. Thomas (UCLA). HIF overexpressing clones were described previously (Sutphin et al., Cancer Res, 67:5896-5905 (2007)). Transfection of RNA oligos were performed with DnarmaFECT Reagent 1 (Dharmcon), according to manufacturer's directions. ON-TARGETplus SMART pools against HIF-1 R/ARNT were purchased from Dharmacon. Inducible shRNAmir to GLUT1 was purchased from Open Biosystems. GLUT1 was detected with anti-GLUT1 antibody from NeoMarkers/LabVision/Fisher. For immunofluorescent studies, GLUT1, GLUT2, and GLUT3 antibodies were purchased from R&D. Pyruvate/lactate levels and hexokinase activity were both measured by fluorometric assay (BioVision and Sigma-Aldrich, respectively). ATP levels were measured by bioluminescence assay (ATP Determination Kit from Molecular Probes/Invitrogen). In vitro kinase activities were performed by Millipore Kinase Profiler.

Cell Viability Assays. For 2,3-bis[2-methoxy-4-nitro-5-sulfophenyl]-2H-tetrazolium-5-carboxanilide (XTT) assays, five thousand cells were plated in 96-well plates. The next day, vehicle (DMSO) or drug was added by serial dilution. Four days later, media were aspirated, XTT solution (0.3 mg/ml of XTT (Sigma), 2.65 mg/ml N-methyl dibenxopyrazine methyl sulfate (Sigma) in phenol red-free media) was added, and the plates were incubated at 37° C. for 1-2 hours. Metabolism of XTT was quantified by measuring the absorbance at 450 nm. IC50s were calculated using linear interpolation. For clonogenic survival assays, three hundred cells were plated per 60 mm tissue culture dish. The cells were allowed to attach overnight and then treated with vehicle or drug for 14 days. Colonies were fixed and stained with crystal violet (0.1% crystal violet in 95% ethanol). All conditions were measured in triplicate and each experiment was done in duplicate or triplicate. To determine necrosis, cells were treated with drug for a given time point. Media and cells were collected, centrifuged, and resuspended in 0.4% trypan blue (Invitrogen). Live and dead cells were counted on a hematocytometer.

Glucose Uptake. One hundred thousand cells were plated per well in a six-well plate. The next day, cells were treated with the indicated concentration of drug and incubated for the indicated time. Cells were then washed twice with phosphate-buffered saline, incubated in low-glucose medium for 30 minutes, and 3H-2-deoxyglucose (0.5 µCi) was added in 1 ml of glucose-free media for an additional hour. Cells were washed twice in PBS and lysed (0.2 N NaOH and 0.2% sodium dodecyl sulfate). Glucose uptake was quantified with a scintillation counter.

Oxygen Consumption. Following treatment with vehicle or drug, cells were trypsinized, suspended at 5 million cells per ml in DMEM+10% FCS, and oxygen consumption was measured in 0.5 ml volume using an Oxytherm electrode unit (Hansatech).

Quantitative Real-Time RT-PCR. Total RNA was extracted from cells (TRIzol, Invitrogen) as per manufacturer's directions. Total RNA (1.5 µg) was reversed transcribed with random hexamers and MMLV-RT. Power SYBR Green PCR reactions were performed in triplicate for each sample and analyzed using the ABI Prism 7900HT sequence detection system. Data were normalized to TBP levels.

Gene Expression Analysis. Data from a human clinical cancer study was used (Jones et al. (2005). Clin Cancer Res 11, 5730-5739.). The Jones study included 49 RCC tumors, 20 non-RCC renal tumors, and 23 normal kidneys samples. The expression levels of all probe sets for GLUT1, GLUT2, GLUT3, and GLUT4 were extracted from the expression studies after robust multi-array normalization.

Affinity Columns. Affi-Gel 15 (BioRad) activated affinity media was coupled to analogs to generate immobilized affinity linkers. Cells were lysed in Ripa buffer and protein was quantified. One microgram of total cell extract was then incubated with one ml of immobilized analogs. These resins were washed and eluted with 9M urea and analyzed by Western blotting.

Molecular Modeling. The likely protonation state of the test compounds at pH 7.4 was predicted using Filter, followed by conformer generation using OMEGA (both from OpenEye Scientific Software, NW; www.eyespone.com). GOLD (Verdonk et al., Proteins, 52:609-623 (2003)) was then used to dock the lowest energy conformer into a 20 Å cavity that covered the internal channel of a GLUT1 homology model (PDB entry 1 SUK (Salas-Burgos et al., *Biophys, J* 87, 2990-2999 (2004)). The Goldscore function was used at maximum search efficiency with the cutoff of 20 poses separated by a minimum RMSD of 2 Å. All predicting binding poses were subsequently refined by energy minimization using SZYBKI with the MMFF94s forcefield and Poisson-Boltzmann implicit solvent model enabled. The ligand and all protein atoms with 8 Å of the ligand were allowed to move. The set of active compounds docked included STF-35, STF-38, STF-39, and STF-40, while inactive included STF-44, STF-45, and STF-46.

In Vivo Studies. All experiments were approved by Stanford's Administrative Panel on Laboratory Animal Care (APLAC) and in accordance with both institutional and national guidelines. Five million cells were implanted subcutaneously into the flanks of nude mice (4-6 weeks old) (Charles River Laboratories). Tumors were measured with calipers. Volume was calculated by the following formula: width$^2$×0.5 length. Once tumors reached an average size of >20 mm$^3$, mice were randomized into vehicle (DMSO diluted in 16% cremaphor EL/PBS) or treated groups. Mice were treated with STF-35 (11.6 mg/kg for the first 3 days, followed by 7.8 mg/kg for the 7-9 days). Five-micron sections were cut for immunohistochemistry. Sections were counterstained with hematoxylin and eosin. For 2-[$^{18}$F]-fluoro-2-deoxy-glucose-positron emission tomography imaging, mice bearing tumors were fasted overnight. The next day, the mice were anesthetized with 2% isoflurane and injected intraperitoneally with 250 µCi of FDG. Mice were imaged for 10 minutes at one hour post-injection, using a Rodent R4 microPET system (Concorde Microsystems). Data were reconstructed into three-dimensional volumes using an ordered subset expectation maximization algorithm and were calibrated into units of percent injected dose per gram.

Red Blood Cell Hemolysis. Blood was collected from mice and humans and centrifuged at 600×g (4° C. for 10 minutes). The plasma was aspirated off and cells were washed twice in PBS+10% FCS. Red blood cells were then resuspended in PBS and treated with STF-35 (2.5 µM or 5 µM) or Red Blood Cell Lysis solution (Sigma).

Statistical Analyses. Student's t test were used to determine significance. All error bars represent the standard error of the mean.

Analogs. Analog production chemistry is available upon request.

```
Primers
ARNT/HIF-1β
Forward:    5'-CTGCCAACCCCGAAATGACAT-3'
Reverse:    5'-GCCGCTTAATAGCCCTCTGG-3'

GLUT1/SLC2A1:
Forward:    5'-GGCCAAGAGTGTGCTAAAGAA-3'
Reverse:    5'-ACAGCGTTGATGCCAGACAG-3'

GLUT2/SLC2A2:
Forward:    5'-GTCACTGGGACCCTGGTTTTC-3'
Reverse:    5'-AGTTGTTGATAGCTTTTCGGTCA-3'

HK1:
Forward:    5'-TGGCCTATTACTTCACGGAGC-3'
Reverse:    5'-GGAATGGACCTTACGAATGTTGG-3'

H K2:
Forward:    5'-TTTGACCACATTGCCGAATGC-3'
Reverse:    5'-GGTCCATGAGACCAGGAAACT-3'

PAI-1/Serpine1:
Forward:    5'-CATCCCCCATCCTACGTGG-3'
Reverse:    5'-CCCCATAGGGTGAGAAAACCA-3'

PDK:
Forward:    5'-CTGTGATACGGATCAGAAACCG-3'
Reverse:    5'-TCCACCAAACAATAAAGAGTG CT-3'
```

-continued

```
PGK:
Forward:    5'-CCTGGGCGGAGCTAAAGTTG-3'
Reverse:    5'-TCTCAGCTTTGGACATTAGGTCT-3'

VEGF:
Forward:    5'-CAACATCACCATG CAGATTATG C-3'
Reverse:    5'-CCCACAGGGATTTTCTTGTCTT-3'
```

Other Relevant Sequences

```
>gi|166795299|ref|NP_006507.2|solute carrier family 2, facilitated glucose
transporter member 1 [Homo sapiens]
MEPSSKKLTGRLMLAVGGAVLGSLQFGYNTGVINAPQKVIEEFYNQTWVHRYGESILPTTLTTLWSLSVAIFSVGGMIGSFSVG
LFVNRFGRRNSMLMMNLLAFVSAVLMGFSKLGKSFEMLILGRFIIGVYCGLTTGFVPMYVGEVSPTALRGALGTLHQLGIVVGI
LIAQVFGLDSIMGNKDLWPLLLSIIFIPALLQCIVLPFCPESPRFLLINRNEENRAKSVLKKLRGTADVTHDLQEMKEESRQMM
REKKVTILELFRSPAYRQPILIAVVLQLSQQLSGINAVFYYSTSIFEKAGVQQPVYATIGSGIVNTAFTVVSLFVVERAGRRTL
HLIGLAGMAGCAILMTIALALLEQLPWMSYLSIVAIFGFVAFFEVGPGPIPWFIVAELFSQGPRPAAIAVAGFSNWTSNFIVGM
CFQYVEQLCGPYVFIIFTVLLVLFFIFTYFKVPETKGRTFDEIASGFRQGGASQSDKTPEELFHPLGADSQV >gi|115502394|sp|P11166.2|GTR1_HUMAN RecName: Full = Solute carrier family 2,
facilitated glucose transporter member 1; AltName: Full = Glucose transporter
type 1, erythrocyte/brain; Short = GLUT-1; AltName: Full = HepG2 glucose transporter
MEPSSKKLTGRLMLAVGGAVLGSLQFGYNTGVINAPQKVIEEFYNQTWVHRYGESILPTTLTTLWSLSVAIFSVGGMIGSFSVG
LFVNRFGRRNSMLMMNLLAFVSAVLMGFSKLGKSFEMLILGRFIIGVYCGLTTGFVPMYVGEVSPTALRGALGTLHQLGIVVGI
LIAQVFGLDSIMGNKDLWPLLLSIIFIPALLQCIVLPFCPESPRFLLINRNEENRAKSVLKKLRGTADVTHDLQEMKEESRQMM
REKKVTILELFRSPAYRQPILIAVVLQLSQQLSGINAVFYYSTSIFEKAGVQQPVYATIGSGIVNTAFTVVSLFVVERAGRRTL
HLIGLAGMAGCAILMTIALALLEQLPWMSYLSIVAIFGFVAFFEVGPGPIPWFIVAELFSQGPRPAAIAVAGFSNWTSNFIVGM
CFQYVEQLCGPYVFIIFTVLLVLFFIFTYFKVPETKGRTFDEIASGFRQGGASQSDKTPEELFHPLGADSQV
```

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The invention claimed is:

1. A method for inhibiting cell growth or proliferation of a cell that is HIF pathway proficient comprising contacting a cell wherein the cell is HIF pathway proficient with a therapeutic entity, wherein the therapeutic entity inhibits the activity of GLUT1 and wherein the therapeutic entity preferentially inhibits the growth or proliferation of neoplastic cells versus normal cells.

2. The method of claim 1, wherein the inhibiting of growth or proliferation of the neoplastic cells results in cell death.

3. The method of claim 1, wherein the therapeutic entity comprises a compound of Formula I, II, III, or IV:

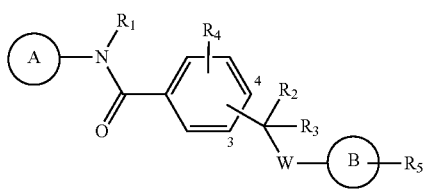

I wherein:

A is a nitrogen-containing heteroaryl ring chosen from pyridinyl, pyrimidinyl, pyrazinyl, quinolinyl, pyrazolyl, imidazolyl, and thiazolyl, each of which is optionally substituted;

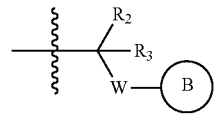

is attached to the phenyl ring at either the 3 or 4 position;

$R_1$, $R_2$, and $R_3$ are each independently chosen from hydrogen, optionally substituted alkyl, and optionally substituted alkenyl;

$R_4$ and $R_5$ are each independently chosen from hydrogen, hydroxy, optionally substituted alkyl, optionally substituted alkenyl, optionally substituted alkoxy, optionally substituted cycloalkyl, optionally substituted aryl, optionally substituted heterocycloalkyl, optionally substituted heteroaryl, halo, carboxy, nitro, sulfonyl, sulfinyl, and optionally substituted amino;

W is chosen from —NRSO$_2$—, —SO$_2$NR—, and —NRCO—, wherein each R is independently chosen from hydrogen, alkyl, alkenyl, alkynyl, cycloalkyl, aryl, heterocycloalkyl, and heteroaryl, each of which, except for hydrogen, is optionally substituted; and B is an aryl ring;

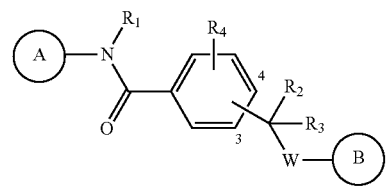

II wherein:

A is a nitrogen-containing heteroaryl ring chosen from pyridinyl, pyrimidinyl, pyrazinyl, quinolinyl, pyrazolyl, imidazolyl, and thiazolyl, each of which is optionally substituted;

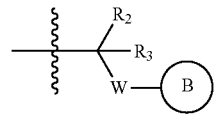

is attached to the phenyl ring at either the 3 or 4 position;

$R_1$, $R_2$, and $R_3$ are each independently chosen from hydrogen, optionally substituted alkyl, and optionally substituted alkenyl;

$R_4$ is chosen from hydrogen, hydroxy, optionally substituted alkyl, optionally substituted alkenyl, optionally substituted alkoxy, optionally substituted cycloalkyl, optionally substituted aryl, optionally substituted heterocycloalkyl, optionally substituted heteroaryl, halo, carboxy, nitro, sulfonyl, sulfinyl, and optionally substituted amino;

W is chosen from —NRSO$_2$—, —SO$_2$NR—, and —NRCO—, wherein each R is independently chosen from hydrogen, alkyl, alkenyl, alkynyl, cycloalkyl, aryl, heterocycloalkyl, and heteroaryl, each of which, except for hydrogen, is optionally substituted; and B is heteroaryl;

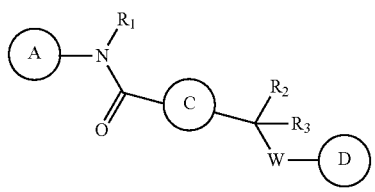

III wherein:

A is a nitrogen-containing heteroaryl ring chosen from pyridinyl, pyrimidinyl, pyrazinyl, quinolinyl, pyrazolyl, imidazolyl, and thiazolyl, each of which is optionally substituted;

$R_1$, $R_2$, and $R_3$ are each independently chosen from hydrogen, optionally substituted alkyl, and optionally substituted alkenyl;

W is chosen from —N(R)SO$_2$R$_X$—, —SO$_2$N(R)R$_X$—, and —N(R)COR$_X$—, wherein each R is independently chosen from hydrogen, alkyl, alkenyl, alkynyl, cycloalkyl, aryl, heterocycloalkyl, and heteroaryl, each of which, except for hydrogen, is optionally substituted; and R$_X$ is an bivalent C$_0$-C$_6$alkylene, bivalent C$_3$-C$_6$cycloalkyl, or phenyl, each of which is optionally substituted;

C is selected from C$_5$-C$_6$cycloalkyl, and phenyl, wherein C is optionally substituted hydrogen, hydroxy, optionally substituted alkyl, optionally substituted alkenyl, optionally substituted alkoxy, optionally substituted cycloalkyl, optionally substituted aryl, optionally substituted heterocycloalkyl, optionally substituted heteroaryl, halo, carboxy, nitro, sulfonyl, sulfinyl, and optionally substituted amino; and D is an optionally substituted heterocycle;

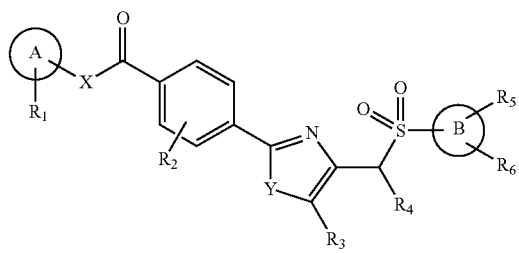

IV wherein

A is a nitrogen-containing heteroaryl ring chosen from pyridinyl, pyrazinyl, and imidazolyl, each of which is optionally substituted;

X is CH$_2$CH$_2$NR, CH$_2$NR, or NR wherein each R is independently chosen from hydrogen, alkyl, alkenyl, alkynyl, cycloalkyl, aryl, heterocycloalkyl, and heteroaryl, each of which, except for hydrogen, is optionally substituted;

$R_1$, $R_2$, $R_3$, and $R_4$ are each independently chosen from hydrogen, alkyl, alkenyl, alkynyl, cycloalkyl, aryl, heterocycloalkyl, and heteroaryl, each of which, except for hydrogen, is optionally substituted;

Y is chosen from O, S, NR; wherein each R is independently chosen from hydrogen, alkyl, alkenyl, alkynyl, cycloalkyl, aryl, heterocycloalkyl, and heteroaryl, each of which, except for hydrogen, is optionally substituted; and B is an optionally substituted aryl ring.

4. The method of claim 1, wherein the therapeutic entity comprises a compound of Formula IA, IIA, IIIA, or IVA:

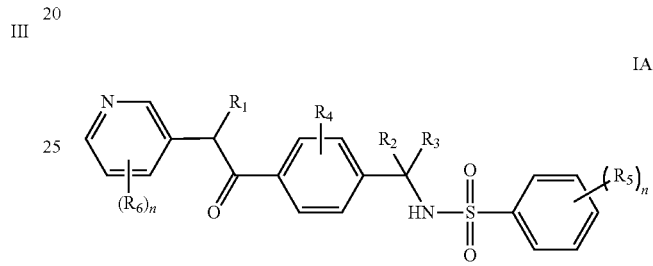

IA wherein:

$R_1$, $R_2$, and $R_3$ are each independently chosen from hydrogen, optionally substituted alkyl, and optionally substituted alkenyl; and each $R_4$ and $R_5$ is independently chosen from hydrogen, hydroxy, optionally substituted alkyl, optionally substituted alkenyl, optionally substituted alkoxy, optionally substituted cycloalkyl, optionally substituted aryl, optionally substituted heterocycloalkyl, optionally substituted heteroaryl, halo, carboxy, nitro, sulfonyl, sulfinyl, and optionally substituted amino; and for each occurrence, $R_6$ is independently chosen from alkyl optionally substituted with one or more halo, alkoxy, halo, nitro, heterocycloalkyl, and amino optionally substituted with C(O)R$_a$, wherein R$_a$ is chosen from alkyl and optionally substituted alkoxy; and each n is 0, 1, or;

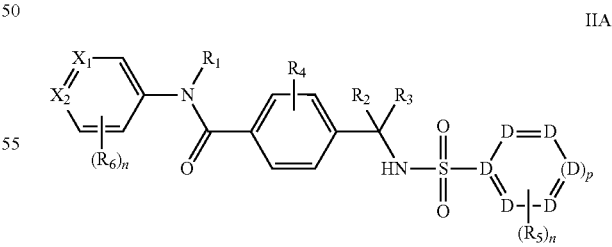

IIA wherein $X_1$ and $X_2$ are each independently chosen from N, NO, and CH, provided that at least one of $X_1$ and $X_2$ is not CH;

each D is individually taken from the group consisting of C, CH, NH, N, S and O, such that the resultant ring is selected from pyridyl, furanyl, imidazolyl, triazolyl, and thienyl;

R₁, R₂, and R₃ are each independently chosen from hydrogen, optionally substituted alkyl, and optionally substituted alkenyl;

R₄ and R₅ are independently chosen from hydrogen, hydroxy, optionally substituted alkyl, optionally substituted alkenyl, optionally substituted alkoxy, optionally substituted cycloalkyl, optionally substituted aryl, optionally substituted heterocycloalkyl, optionally substituted heteroaryl, halo, carboxy, nitro, sulfonyl, sulfinyl, and optionally substituted amino; and for each occurrence, R₆ is independently chosen from alkyl optionally substituted with one or more halo, alkoxy, halo, nitro, heterocycloalkyl, and amino optionally substituted with C(O)Rₐ, wherein Rₐ is chosen from alkyl and optionally substituted alkoxy;

each n is 0, 1 or 2; and
p is 0 or 1;

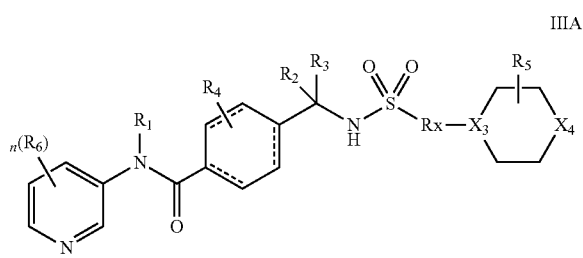

IIIA wherein:
X₃ is selected from CH or N;
X₄ is selected from O, NH, or NR₁;
R₁, R₂, and R₃ are each independently chosen from hydrogen, optionally substituted alkyl, and optionally substituted alkenyl;

R₄ and R₅ are independently chosen from hydrogen, hydroxy, optionally substituted alkyl, optionally substituted alkenyl, optionally substituted alkoxy, optionally substituted cycloalkyl, optionally substituted aryl, optionally substituted heterocycloalkyl, optionally substituted heteroaryl, halo, carboxy, nitro, sulfonyl, sulfinyl, and optionally substituted amino;

for each occurrence, R₆ is independently chosen from alkyl optionally substituted with one or more halo, alkoxy, halo, nitro, heterocycloalkyl, and amino optionally substituted with C(O)Rₐ, wherein Rₐ is chosen from alkyl and optionally substituted alkoxy;

Rₓ is an bivalent C₄alkylene, bivalent C₆cycloalkyl, or phenyl, each of which is optionally substituted; and n is 0, 1, or 2;

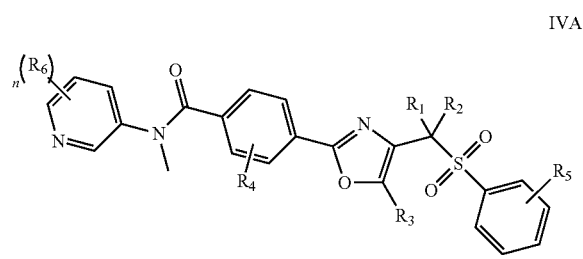

IVA wherein
R₁, R₂, and R₃ are each independently chosen from hydrogen, alkyl, alkenyl, alkynyl, cycloalkyl, aryl, heterocycloalkyl, and heteroaryl, each of which, except for hydrogen, is optionally substituted;

R₄ and R₅ are independently chosen from hydrogen, hydroxy, optionally substituted alkyl, optionally substituted alkenyl, optionally substituted alkoxy, optionally substituted cycloalkyl, optionally substituted aryl, optionally substituted heterocycloalkyl, optionally substituted heteroaryl, halo, carboxy, nitro, sulfonyl, sulfinyl, and optionally substituted amino;

for each occurrence, R₆ is independently chosen from alkyl optionally substituted with one or more halo, alkoxy, halo, nitro, heterocycloalkyl, and amino optionally substituted with C(O)Rₐ, wherein Rₐ is chosen from alkyl and optionally substituted alkoxy; and n is 0, 1, or 2.

5. The method of claim 1, wherein the therapeutic entity comprises a compound selected from the group consisting of 4-(Phenylsulfonamidomethyl)-N-(pyridin-2-yl)benzamide;
4-(Phenylsulfonamidomethyl)-N-(pyridin-3-yl)benzamide;
4-(Phenylsulfonamidomethyl)-N-(pyridin-4-yl)benzamide;
4-(Phenylsulfonamidomethyl)-N-(thiazol-2-yl)benzamide;
4-(Phenylsulfonamidomethyl)-N-(1H-pyrazol-3-yl)benzamide;
4-(Phenylsulfonamidomethyl)-N-(quinolin-3-yl)benzamide;
4-(Phenylsulfonamidomethyl)-N-(quinolin-5-yl)benzamide;
4-(Phenylsulfonamidomethyl)-N-(pyrazin-2-yl)benzamide;
4-(Phenylsulfonamidomethyl)-N-(pyrimidin-2-yl)benzamide;
4-((2-Methylphenylsulfonamido)methyl)-N-(pyridin-3-yl)benzamide;
4-((2-Fluorophenylsulfonamido)methyl)-N-(pyridin-3-yl)benzamide;
4-((2-Chlorophenylsulfonamido)methyl)-N-(pyridin-3-yl)benzamide;
4-((2-Bromophenylsulfonamido)methyl)-N-(pyridin-3-yl)benzamide;
Methyl 2-(N-(4-(Pyridin-3-ylcarbamoyl)benzyl)sulfamoyl)benzoate;
N-(Pyridin-3-yl)-4-((2-(trifluoromethyl)phenylsulfonamido)methyl)benzamide;
4-((2-Cyanophenylsulfonamido)methyl)-N-(pyridin-3-yl)benzamide;
4-((3-Aminophenylsulfonamido)methyl)-N-(pyridin-3-yl)benzamide;
4-((3-Methylphenylsulfonamido)methyl)-N-(pyridin-3-yl)benzamide;
4-((3-Fluorophenylsulfonamido)methyl)-N-(pyridin-3-yl)benzamide;
4-((3-Bromophenylsulfonamido)methyl)-N-(pyridin-3-yl)benzamide;
4-((3-Cyanophenylsulfonamido)methyl)-N-(pyridin-3-yl)benzamide;
4-((3-Nitrophenylsulfonamido)methyl)-N-(pyridin-3-yl)benzamide;
4-{[([1,1'-Biphenyl]-3-ylsulfonyl)amino]methyl}-N-(3-pyridinyl)benzamide;
4-[({[3-(2-Pyrimidinyl)phenyl]sulfonyl}amino)methyl]-N-(3-pyridinyl)benzamide;
4-[({[3-(1-Methyl-1H-pyrazol-3-yl)phenyl]sulfonyl}amino)methyl]-N-(3-pyridinyl)benzamide;

4-[({[3-(5-Methyl-1,3,4-oxadiazol-2-yl)phenyl] sulfonyl}amino)methyl]-N-(3-pyridinyl)benzamide;
4-[({[3-(5-Methyl-1,2,4-oxadiazol-3-yl)phenyl] sulfonyl}amino)methyl]-N-(3-pyridinyl)benzamide;
4-[({[3-(2-Methyl-1,3-thiazol-4-yl)phenyl] sulfonyl}amino)methyl]-N-(3-pyridinyl)benzamide;
4-((4-Aminophenylsulfonamido)methyl)-N-(pyridin-3-yl)benzamide;
4-((4-Butoxyphenylsulfonamido)methyl)-N-(pyridin-3-yl)benzamide;
4-((4-Phenoxyphenylsulfonamido)methyl)-N-(pyridin-3-yl)benzamide;
4-((4-Methylphenylsulfonamido)methyl)-N-(pyridin-3-yl)benzamide;
4-((4-Propylphenylsulfonamido)methyl)-N-(pyridin-3-yl)benzamide;
4-[({[4-(1-Adamantyl)phenyl]sulfonyl}amino)methyl]-N-(3-pyridinyl)benzamide;
4-[({[4-(3-Chloro-1-adamantyl)phenyl]sulfonyl}amino) methyl]-N-(3-pyridinyl)benzamide;
Methyl 3-{4-[({4-[(3Pyridinylamino)carbonyl] benzyl}amino)sulfonyl]phenyl}propanoate;
4-((4-Acetamidophenylsulfonamido)methyl)-N-(pyridin-3-yl)benzamide;
4-((4-Chlorophenylsulfonamido)methyl)-N-(pyridin-3-yl)benzamide;
4-((4-Bromophenylsulfonamido)methyl)-N-(pyridin-3-yl)benzamide;
N-(Pyridin-3-yl)-4-((4-(trifluoromethoxy)phenylsulfonamido)methyl)benzamide;
Methyl 4-(N-(4-(Pyridin-3-ylcarbamoyl)benzyl)sulfamoyl)benzoate;
N-(Pyridin-3-yl)-4-((4-(trifluoromethyl)phenylsulfonamido)methyl)benzamide;
4-((4-Cyanophenylsulfonamido)methyl)-N-(pyridin-3-yl) benzamide;
4-((4-Nitrophenylsulfonamido)methyl)-N-(pyridin-3-yl) benzamide;
4-((Biphenyl-4-ylsulfonamido)methyl)-N-(pyridin-3-yl) benzamide;
4-({[(4'-Methoxy[1,1'-biphenyl]-4-yl)sulfonyl] amino}methyl)-N-(3-pyridinyl)benzamide;
4-({[(4'-Methyl[1,1'-biphenyl]-4-yl)sulfonyl] amino}methyl)-N-(3-pyridinyl)benzamide;
4-({[(4'-Fluoro[1,1'-biphenyl]-4-yl)sulfonyl] amino}methyl)-N-(3-pyridinyl)benzamide;
4-({[(4'-Chloro[1,1'-biphenyl]-4-yl)sulfonyl] amino}methyl)-N-(3-pyridinyl)benzamide;
4-[({[4-(2-Pyrimidinyl)phenyl]sulfonyl}amino)methyl]-N-(3-pyridinyl)-benzamide;
4-[({[4-(1H-Pyrazol-1-yl)phenyl]sulfonyl}amino)methyl]-N-(3-pyridinyl)benzamide;
4-[({[4-(2-Methyl-1,3-thiazol-4-yl)phenyl] sulfonyl}amino)methyl]-N-(3-pyridinyl)benzamide;
[({[4-(1,3-Oxazol-5-yl)phenyl]sulfonyl}amino)methyl]-N-(3-pyridinyl)benzamide;
4-((3,4-Dimethoxyphenylsulfonamido)methyl)-N-(pyridin-3-yl)benzamide;
4-((3-tert-Butyl-4-methoxyphenylsulfonamido)methyl)-N-(pyridin-3-yl)benzamide;
4-((2,3,4,5,6-Pentamethylphenylsulfonamido)methyl)-N-(pyridin-3-yl)benzamide;
4-((2,4-Dimethylphenylsulfonamido)methyl)-N-(pyridin-3-yl)benzamide;
4-((3,4-Dimethylphenylsulfonamido)methyl)-N-(pyridin-3-yl)benzamide;
4-((3,5-Dimethylphenylsulfonamido)methyl)-N-(pyridin-3-yl)benzamide;
4-((3-Fluoro-4-methylphenylsulfonamido)methyl)-N-(pyridin-3-yl)benzamide;
4-((3-Chloro-2-methylphenylsulfonamido)methyl)-N-(pyridin-3-yl)benzamide;
4-((3-Chloro-4-methylphenylsulfonamido)methyl)-N-(pyridin-3-yl)benzamide;
4-((3,4-Dichlorophenylsulfonamido)methyl)-N-(pyridin-3-yl)benzamide;
4-((3-Cyano-4-fluorophenylsulfonamido)methyl)-N-(pyridin-3-yl)benzamide;
4-((Naphthalene-2-sulfonamido)methyl)-N-(pyridin-3-yl)benzamide;
4-((5-(Dimethylamino)naphthalene-1-sulfonamido)methyl)-N-(pyridin-3-yl)benzamide;
4-((2,3-Dihydro-1H-indene-5-sulfonamido)methyl)-N-(pyridin-3-yl)benzamide;
4-((2-(Dimethylamino)-2,3-dihydro-1H-indene-5-sulfonamido)methyl)-N-(pyridin-3-yl)benzamide;
4-((4-(4-Methylpiperazin-1-yl)phenylsulfonamido)methyl)-N-(pyridin-3-yl)benzamide;
4-[({4-[(Dimethylamino)methyl]phenyl}sulfonyl)amino] methyl-N-(3-pyridinyl)benzamide;
4-{[({4-[(Diethylamino)methyl]phenyl}sulfonyl)amino] methyl}-N-(3-pyridinyl)benzamide,
4-{[({4-[(Dipropylamino)methyl]phenyl}sulfonyl) amino]methyl}-N-(3-pyridinyl)benzamide;
4-[({[4-(1-Pyrrolidinylmethyl)phenyl]sulfonyl}amino) methyl]-N-(3-pyridinyl)-benzamide;
4-[({[4-(1-Piperidinylmethyl)phenyl]sulfonyl}amino) methyl]-N-(3-pyridinyl)benzamide;
4-[({[4-(1-Azepanylmethyl)phenyl]sulfonyl}amino)methyl]-N-(3-pyridinyl)benzamide;
4-[({[4-(4-Morpholinylmethyl)phenyl]sulfonyl}amino) methyl]-N-(3-pyridinyl)benzamide;
4-{[({4-[(4-Methoxy-1-piperidinyl)methyl] phenyl}sulfonyl)amino]methyl}-N-(3-pyridinyl)benzamide;
4-{[({4-[(4-Methyl-1-piperazinyl)methyl] phenyl}sulfonyl)amino]methyl}-N-(3-pyridinyl)benzamide;
4-tert-Butyl-N-(4-(pyridin-3-ylcarbamoyl)benzyl)benzamide;
4-((4-tert-Butylphenylsulfonamido)methyl)-N-methyl-N-(pyridin-3-yl)benzamide;
N-Methyl-4-(phenylsulfonamidomethyl)-N-(pyridin-3-yl)benzamide;
3-((4-tert-Butylphenylsulfonamido)methyl)-N-(pyridin-3-yl)benzamide;
3-(Phenylsulfonamidomethyl)-N-(pyridin-3-yl)benzamide;
3-(4-(Phenylsulfonamidomethyl)benzamido)pyridine 1-oxide;
4-((4-Iodophenylsulfonamido)methyl)-N-(pyridin-3-yl) benzamide;
4-((4-Ethynylphenylsulfonamido)methyl)-N-(pyridin-3-yl)benzamide;
4-((4-Bromophenylsulfonamido)methyl)-N-(pyridin-3-yl)benzamide;
4-((4-Fluorophenylsulfonamido)methyl)-N-(pyridin-3-yl)benzamide;
3,5-Dimethyl-N-(4-(pyridin-3-ylcarbamoyl)benzyl)benzamide;
3,4-Dimethoxy-N-(4-(pyridin-3-ylcarbamoyl)benzyl) benzamide;

4-{[({4-[3-(Methyloxy)-1-propynyl]phenyl}sulfonyl)amino]methyl}-N-(3-pyridinyl)benzamide;
4-[(4-Iodophenylsulfonamido)methyl]-N-methyl-N-(4-pyridinyl)benzamide;
4-[({4-(21-Amino-4,7,10,13,16,19-hexaoxahenicos-1-yn-1-yl)phenyl]sulfonyl}amino)methyl]-N-(3-pyridinyl)benzamide;
4-[({[4-(3-Methoxypropyl)phenyl]sulfonyl}amino)methyl]-N-(3-pyridinyl)benzamide;
4-[({[4-(1-benzyl-1H-1,2,3-triazol-4-yl)phenyl]sulfonyl}amino)methyl]-N-(3-pyridinyl)benzamide;
4-[({[4-(3-Hydroxy-1-propynyl)phenyl]sulfonyl}amino)methyl]-N-(3-pyridinyl)benzamide;
4-[({[4-(3-Hydroxypropyl)phenyl]sulfonyl}amino)methyl]-N-(3-pyridinyl)benzamide;
4-[({[4-(21-Amino-4,7,10,13,16,19-hexaoxahenicos-1-yn-1-yl)phenyl]sulfonyl}amino)methyl]-N-(4-pyridinyl)benzamide;
4-((4-tert-Butylphenylsulfonamido)methyl)-N-(pyridin-4-yl)benzamide;
4-({[(4-tert-Butylphenyl)sulfonyl]amino}methyl)-N-(5-methyl-3-pyridinyl)benzamide;
4-({[(4-tert-Butylphenyl)sulfonyl]amino}methyl)-N-(2-methyl-3-pyridinyl)benzamide;
4-({[(4-tert-Butylphenyl)sulfonyl]amino}methyl)-N-(6-methyl-3-pyridinyl)benzamide;
4-({[(4-tert-Butylphenyl)sulfonyl]amino}methyl)-N-(6-methoxy-3-pyridinyl)benzamide;
4-({[(4-tert-Butylphenyl)sulfonyl]amino}methyl)-N-(6-chloro-3-pyridinyl)benzamide;
4-({[(4-tert-Butylphenyl)sulfonyl]amino}methyl)-N-(4-chloro-3-pyridinyl)benzamide;
4-({[(4-tert-Butylphenyl)sulfonyl]amino}methyl)-N-(2-chloro-3-pyridinyl)benzamide;
4-({[(4-tert-Butylphenyl)sulfonyl]amino}methyl)-N-(4-methyl-3-pyridinyl)benzamide;
4-({[(4-tert-Butylphenyl)sulfonyl]amino}methyl)-N-(5-chloro-3-pyridinyl)benzamide;
4-({[(4-tert-Butylphenyl)sulfonyl]amino}methyl)-N-(2-nitro-3-pyridinyl)benzamide;
4-({[(4-tert-Butylphenyl)sulfonyl]amino}methyl)-N-[6-(4-morpholinyl)-3-pyridinyl]benzamide;
4-({[(4-tert-Butylphenyl)sulfonyl]amino}methyl)-N-[6-(trifluoromethyl)-3-pyridinyl]benzamide;
N-[6-(Acetylamino)-3-pyridinyl]-4-({[(4-tert-butylphenyl)sulfonyl]amino}methyl)benzamide;
4-({[(4-tert-Butylphenyl)sulfonyl]amino}methyl)-N-(6-fluoro-3-pyridinyl)benzamide;
4-({[(4-tert-Butylphenyl)sulfonyl]amino}methyl)-N-(5-fluoro-3-pyridinyl)benzamide;
4-({[(4-tert-Butylphenyl)sulfonyl]amino}methyl)-N-[4-(trifluoromethyl)-3-pyridinyl]benzamide;
4-({[(4-tert-Butylphenyl)sulfonyl]amino}methyl)-N-(2-fluoro-3-pyridinyl)benzamide;
4-({[(4-tert-Butylphenyl)sulfonyl]amino}methyl)-N-(4-methoxy-3-pyridinyl)benzamide;
N-(6-Bromo-3-pyridinyl)-4-({[(4-tert-butylphenyl)sulfonyl]amino}methyl)benzamide;
4-[({[3-(4-Morpholinyl)phenyl]sulfonyl}amino)methyl]-N-(3-pyridinyl)benzamide;
4-[({[4-(4-Morpholinyl)phenyl]sulfonyl}amino)methyl]-N-(3-pyridinyl)benzamide;
4-[({[4-(1-Piperidinyl)phenyl]sulfonyl}amino)methyl]-N-(3-pyridinyl)benzamide;
4-[({[4-(1-Piperidinyl)phenyl]sulfonyl}amino)methyl]-N-(3-pyridinyl)benzamide;
4-[({[4-(21-Amino-4,7,10,13,16,19-hexaoxahenicos-1-yl)phenyl]sulfonyl}amino) methyl]-N-(3-pyridinyl)benzamide;
4-({[(4-{[3-(4-Morpholinyl)propyl]amino}phenyl)sulfonyl]amino}methyl)-N-(3-pyridinyl)benzamide;
4-[({[3-(4-Methyl-1-piperazinyl)phenyl]sulfonyl}amino)methyl]-N-(3-pyridinyl)benzamide;
4-({[(4-{[2-(Dimethylamino)ethyl]amino}phenyl)sulfonyl]amino}methyl)-N-(3-pyridinyl)benzamide;
N-(3-Pyridinyl)-4-[({[3'-(trifluoromethyl)[1,1'-biphenyl]-4-yl]sulfonyl}amino)methyl]benzamide;
4-({[(4-Benzylphenyl)sulfonyl]amino}methyl)-N-(3-pyridinyl)benzamide;
4-{[({4-[3-(4-Morpholinyl)-1-propynyl]phenyl}sulfonyl)amino]methyl}-N-(3-pyridinyl)benzamide;
4-{[({4-[3-(Dimethylamino)-1-propynyl]phenyl}sulfonyl)amino]methyl}-N-(3-pyridinyl)benzamide;
4-{[[(4-tert-Butylphenyl)sulfonyl](methyl)amino]methyl}-N-(3-pyridinyl)benzamide;
4-{[[(4-tert-Butylphenyl)sulfonyl](ethyl)amino]methyl}-N-(3-pyridinyl)benzamide;
4-{[[(4-tert-Butylphenyl)sulfonyl](propyl)amino]methyl}-N-(3-pyridinyl)benzamide;
4-{[({4-[3-(4-Morpholinyl)propyl]phenyl}sulfonyl)amino]methyl}-N-(3-pyridinyl)benzamide;
4-{[({4-[3-(Dimethylamino)propyl]phenyl}sulfonyl)amino]methyl}-N-(3-pyridinyl)benzamide;
4-[({[3-(Propionylamino)phenyl]sulfonyl}amino)methyl]-N-(3-pyridinyl)benzamide;
4-[({[3-(Acryloylamino)phenyl]sulfonyl}amino)methyl]-N-(3-pyridinyl)benzamide;
4-({[(4-tert-Butylphenyl)sulfonyl]amino}methyl)-2-methyl-N-(3-pyridinyl)benzamide;
4-({[(4-tert-Butylphenyl)sulfonyl]amino}methyl)-2-fluoro-N-(3-pyridinyl)benzamide;
4-({[(4-tert-Butylphenyl)sulfonyl]amino}methyl)-3-methyl-N-(3-pyridinyl)benzamide;
4-({[(4-tert-Butylphenyl)sulfonyl]amino}methyl)-3-fluoro-N-(3-pyridinyl)benzamide;
4-(1-{[(4-tert-Butylphenyl)sulfonyl]amino}ethyl)-N-(3-pyridinyl)benzamide;
4-[(anilinosulfonyl)methyl]-N-(3-pyridinyl)benzamide;
4-{[(4-tert-butylanilino)sulfonyl]methyl}-N-(3-pyridinyl)benzamide;
4-{[(4-fluoroanilino)sulfonyl]methyl}-N-(3-pyridinyl)benzamide;
4-({[4-(4-methyl-1-piperazinyl)anilino]sulfonyl}methyl)-N-(3-pyridinyl)benzamide;
4-((4-(tert-butyl)phenylsulfonamido)methyl)-2-methyl-N-(pyridin-3-yl)benzamide;
4-((4-(tert-butyl)phenylsulfonamido)methyl)-3-methyl-N-(pyridin-3-yl)benzamide;
4-((4-(tert-butyl)phenylsulfonamido)methyl)-2-fluoro-N-(pyridin-3-yl)benzamide;
4-((4-(tert-butyl)phenylsulfonamido)methyl)-3-fluoro-N-(pyridin-3-yl)benzamide;
4-((4-(tert-butyl)phenylsulfonamido)methyl)-3-nitro-N-(pyridin-3-yl)benzamide;
4-(1-(4-(tert-butyl)phenylsulfonamido)ethyl)-N-(pyridin-3-yl)benzamide,
4-(N-phenylsulfamoylmethyl)-N-(pyridin-3-yl)benzamide;
4-((N-(4-fluorophenyl)sulfamoyl)methyl)-N-(pyridin-3-yl)benzamide;
4-((N-(4-tert-butylphenyl)sulfamoyl)methyl)-N-(pyridin-3-yl)benzamide;

4-((N-(4-(4-methylpiperazin-1-yl)phenyl)sulfamoyl)methyl)-N-(pyridin-3-yl)benzamide;
4-((3-Methoxyphenylsulfonamido)methyl)-N-(pyridin-3-yl)benzamide;
4-((3,4-dimethylphenylsulfonamido)methyl)-N-(pyridin-3-yl)benzamide;
3-((3,4-dimethylphenylsulfonamido)methyl)-N-(pyridin-3-yl)benzamide;
N-(pyridin-3-yl)-3((2,3,4-trifluorophenylsulfonamido) methyl)benzamide;
N-(pyridin-3-yl)-4-((2,3,4-trifluorophenylsulfonamido) methyl)benzamide;
N-(pyridin-3-yl)-3-((2,3,5,6-tetramethylphenylsulfonamido)methyl)benzamide;
N-(pyridin-3-yl)-4-((2,3,5,6-tetramethylphenylsulfonamido)methyl)benzamide;
3-((2,5-dimethylphenylsulfonamido)methyl)-N-(pyridin-3-yl)benzamide;
4-((2,5-dimethylphenylsulfonamido)methyl)-N-(pyridin-3-yl)benzamide;
4-((3-Chlorophenylsulfonamido)methyl)-N-(pyridin-3-yl)benzamide,
N-(Pyridin-3-yl)-4-((3-(trifluoromethyl)phenylsulfonamido)methyl)benzamide,
4-((4-Methoxyphenylsulfonamido)methyl)-N-(pyridin-3-yl)benzamide,
3-((4-tert-Butylphenylsulfonamido)methyl)-N-(pyridin-3-yl)benzamide,
4-((4-Fluorophenylsulfonamido)methyl)-N-(pyridin-3-yl)benzamide, and
4-((4-Acetylphenylsulfonamido)methyl)-N-(pyridin-3-yl)benzamide.
N-(3-Pyridinyl)-4-{[(3-pyridylsulfonyl)amino] methyl}benzamide;
4-({[(6-Chloro-3-pyridinyl)sulfonyl]amino}methyl)-N-(3-pyridinyl)benzamide;
4-({[(6-Phenoxy-3-pyridinyl)sulfonyl]amino}methyl)-N-(3-pyridinyl)benzamide;
N-(3-Pyridinyl)-4-{[(2-thienylsulfonyl)amino] methyl}benzamide;
N-(3-Pyridinyl)-4-{[(3-thienylsulfonyl)amino] methyl}benzamide;
4-({[(1,2-Dimethyl-1H-imidazol-5-yl)sulfonyl] amino}methyl)-N-(3-pyridinyl)benzamide;
N-(3-Pyridinyl)-4-{[(4H-1,2,4-triazol-3-ylsulfonyl) amino]methyl}benzamide;
N-(3-Pyridinyl)-4-{[(2-furanylsulfonyl)amino] methyl}benzamide;
4-((4-(4-methylpiperazin-1-yl)cyclohexanesulfonamido) methyl)-N-(pyridin-3-yl)benzamide; and
4-(5-Methyl-4-{[(4-methylphenyl)sulfonyl]methyl}-1,3-oxazol-2-yl)-N-(3-pyridinyl)benzamide;
4-(5-Methyl-4-{[(4-methylphenyl)sulfonyl]methyl}-1,3-oxazol-2-yl)-N-(4-pyridinyl)benzamide;
N-Methyl-4-(5-methyl-4-{[(4-methylphenyl)sulfonyl] methyl}-1,3-oxazol-2-yl)-N-(3-pyridinyl)benzamide;
4-(5-Methyl-4-{[(4-methylphenyl)sulfonyl]methyl}-1,3-oxazol-2-yl)-N-(2-pyridinylmethyl)benzamide;
4-(5-Methyl-4-{[(4-methylphenyl)sulfonyl]methyl}-1,3-oxazol-2-yl)-N-(3-pyridinylmethyl)benzamide;
4-(5-Methyl-4-{[(4-methylphenyl)sulfonyl]methyl}-1,3-oxazol-2-yl)-N-(4-pyridinylmethyl)benzamide;
N-Methyl-4-(5-methyl-4-{[(4-methylphenyl)sulfonyl] methyl}-1,3-oxazol-2-yl)-N-(3-pyridinylmethyl)benzamide;
4-(5-Methyl-4-{[(4-methylphenyl)sulfonyl]methyl}-1,3-oxazol-2-yl)-N-[2-(3-pyridinyl)ethyl]benzamide;
4-(5-Methyl-4-{[(4-methylphenyl)sulfonyl]methyl}-1,3-oxazol-2-yl)-N-(2-pyrazinylmethyl)benzamide;
N-[(1-Methyl-1H-imidazol-2-yl)methyl]-4-(5-methyl-4-{[(4-methylphenyl)sulfonyl]methyl}-1,3-oxazol-2-yl) benzamide;
N-[(1-Methyl-1H-imidazol-5-yl)methyl]-4-(5-methyl-4-{[(4-methylphenyl)sulfonyl]methyl}-1,3-oxazol-2-yl) benzamide;
4-{5-Methyl-4-[(phenylsulfonyl)methyl]-1,3-oxazol-2-yl}-N-(3-pyridinylmethyl)benzamide;
4-(4-{[(4-Chlorophenyl)sulfonyl]methyl}-5-methyl-1,3-oxazol-2-yl)-N-(3-pyridinylmethyl)benzamide;
4-(4-{[(4-tert-Butylphenyl)sulfonyl]methyl}-5-methyl-1,3-oxazol-2-yl)-N-(3-pyridinylmethyl)benzamide;
4-(4-{[(3,5-Dimethylphenyl)sulfonyl]methyl}-5-methyl-1,3-oxazol-2-yl)-N-(3-pyridinylmethyl)benzamide;
4-(4-{[(4-Bromophenyl)sulfonyl]methyl}-5-methyl-1,3-oxazol-2-yl)-N-(3-pyridinylmethyl)benzamide;
4-(5-Methyl-4-{[(3-methylphenyl)sulfonyl]methyl}-1,3-oxazol-2-yl)-N-(3-pyridinylmethyl)benzamide;
4-(4-{[(4-Methoxyphenyl)sulfonyl]methyl}-5-methyl-1,3-oxazol-2-yl)-N-(3-pyridinylmethyl)benzamide;
4-(5-Methyl-4-{[(3-methoxyphenyl)sulfonyl]methyl}-1,3-oxazol-2-yl)-N-(3-pyridinylmethyl)benzamide;
4-(4-{[(3,4-Dimethoxyphenyl)sulfonyl]methyl}-5-methyl-1,3-oxazol-2-yl)-N-(3-pyridinylmethyl)benzamide;
4-(5-Methyl-4-{[(2,4-dimethylphenyl)sulfonyl]methyl}-1,3-oxazol-2-yl)-N-(3-pyridinylmethyl)benzamide;
4-(4-{[(4-Fluorophenyl)sulfonyl]methyl}-5-methyl-1,3-oxazol-2-yl)-N-(3-pyridinylmethyl)benzamide;
4-[5-Methyl-4-({[4-(4-methyl-1-piperazinyl)phenyl] sulfonyl}methyl)-1,3-oxazol-2-yl]-N-(3-pyridinylmethyl)benzamide;
4-[5-Methyl-4-({[4-(4-morpholinyl)phenyl] sulfonyl}methyl)-1,3-oxazol-2-yl]-N-(3-pyridinylmethyl)benzamide;
4-(4-{[(4-Methylphenyl)sulfonyl]methyl}-1,3-thiazol-2-yl)-N-(3-pyridinylmethyl)benzamide;
4-(5-methyl-4-(phenylsulfonylmethyl)oxazol-2-yl)-N-(pyridin-3-ylmethyl)benzamide; and
4-(5-methyl-4-(tosylmethyl)oxazol-2-yl)-N-(pyridin-3-ylmethyl)benzamide.

6. The method of claim 1, wherein the therapeutic entity inhibits the activity of GLUT1 via binding to a synthetic targeting region of GLUT1.

7. The method of claim 1, wherein the therapeutic entity inhibits the activity of GLUT1 via binding to a transmembrane region of GLUT1 selected from the group consisting of TMS2 (aa64-86), TMS4 (aa120-141), TMS5 (aa157-178), TMS7 (aa267-291), TMS8 (aa305-325), TMS11(aa401-421) and a combination thereof.

8. The method of claim 1, wherein the therapeutic entity inhibits the activity of GLUT1 via binding to a region about 19 angstroms in length along the axis perpendicular to a cell membrane or a region marked by GLY286C of GLUT1 at a first end and THR137C of GLUT1 at a second end.

9. The method of claim 1, wherein the therapeutic entity inhibits the activity of GLUT1 via binding to a region defined by residues ILE168, GLN72, THR310, ILE311, GLY314, SER313, GLY282, GLY286, and ILE287 of GLUT1.

10. The method of claim 1, wherein the therapeutic entity inhibits the activity of GLUT1 via binding to a region defined by residues GLN282, GLN283, ILE287, PHE416, TRP412, ILE164, ILE168, ASN34, GLY31, THR30, and GLY27 of GLUT1, or at least PHE416, TRP412, ILE168 and ILE287, GLU380 of GLUT1, or at least GLN283 and ASN34 of GLUT1.

11. The method of claim 1, wherein the therapeutic entity inhibits the activity of GLUT1 via binding to a region defined by residues TRP412, THR30. CYS133. SER73, GLY76 and GLY134 of GLUT1.

12. The method of claim 1, wherein the therapeutic entity inhibits the activity of GLUT1 via binding to a region defined by residues ASN23, TRP388, HIS160, THR136, THR137, LEU159, LEU162, GLY163, SER23, ILE164, and TRP412 of GLUT1.

13. The method of claim 1, wherein the HIF pathway is defined by at least two genes selected from the group consisting of VHL, HIF, PDK1, PDH, GLUT1, MXI1, MYC, Ras, and PTEN.

14. The method of claim 1, wherein the cell is glycolysis dependent.

15. The method of claim 1, wherein the cell has a genetic condition selected from the group consisting of a VHL mutation, a Ras signaling pathway mutation, a SRC mutation, a PTEN mutation, somatic gene amplification of GLUT1, somatic Akt gene amplification, and a p53 mutation.

16. The method of claim 1, wherein the cell has HIF stabilization.

17. The method of claim 1, wherein the cell has reduced mitochondria function.

18. The method of claim 1, wherein the cell has aerobic glycolysis.

19. The method of claim 1, wherein the cell has pyruvate dehydrogenase kinase 1 (PDK1) up-regulation.

20. The method of claim 1, wherein the cell has pyruvate dehydrogenase (PDH) down-regulation.

21. The method of claim 1, wherein the cell has MXI1 up-regulation or MYC down-regulation.

22. The method of claim 1, wherein the neoplastic cells are cells are from cancer or tumor.

23. The method of claim 1, wherein the cell is from a hemaetologic cancer, reproductive cancer, brain cancer, spinal cancer, nerve cancer, liver cancer, lung cancer, skin cancer, urogenital cancer, excretory cancer, endocrine cancer and epithelial cancer or a combination thereof or a combination thereof.

24. The method of claim 1, wherein the cell is from clear cell renal cell cancer, AML, CLL or a combination thereof.

25. A method for inhibiting cell growth or proliferation comprising contacting a cell with a therapeutic entity, wherein the therapeutic entity inhibits the activity of GLUT1 and affects the activity of a gene in HIF pathway, and wherein the therapeutic entity preferentially inhibits the growth or proliferation of neoplastic cells versus normal cells.

26. A method for treating neoplasia comprising administering to a subject determined to be HIF pathway proficient with a therapeutic entity, wherein the therapeutic entity inhibits the activity of GLUT1 and wherein the therapeutic entity preferentially inhibits the growth or proliferation of neoplastic cells versus normal cells in the subject.

27. The method of claim 26, wherein the inhibiting of growth or proliferation of the neoplastic cells results in cell death.

28. A method for treating neoplasia comprising
determining whether a subject is HIF pathway proficient, and
administering to a subject that is determined HIF pathway proficient a therapeutic entity,
wherein the therapeutic entity inhibits the activity of GLUT1.

29. A method for monitoring the effectiveness of a treatment comprising monitoring the utilization of glucose by neoplastic cells versus normal cells upon administering a therapeutic entity to a subject determined to be HIF pathway proficient, wherein the therapeutic entity inhibits the activity of GLUT1.

* * * * *